United States Patent
Kuroki et al.

(10) Patent No.: US 10,032,826 B2
(45) Date of Patent: Jul. 24, 2018

(54) LIGHT EXTRACTION SUBSTRATE, METHOD FOR MANUFACTURING LIGHT EXTRACTION SUBSTRATE, ORGANIC ELECTROLUMINESCENT ELEMENT, AND METHOD FOR MANUFACTURING ORGANIC ELECTROLUMINESCENT ELEMENT

(71) Applicant: KONICA MINOLTA, INC., Tokyo (JP)

(72) Inventors: Takaaki Kuroki, Hachioji (JP); Yasunobu Kobayashi, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 15/517,103

(22) PCT Filed: Oct. 20, 2015

(86) PCT No.: PCT/JP2015/079576
§ 371 (c)(1),
(2) Date: Apr. 5, 2017

(87) PCT Pub. No.: WO2016/063869
PCT Pub. Date: Apr. 28, 2016

(65) Prior Publication Data
US 2017/0309677 A1    Oct. 26, 2017

(30) Foreign Application Priority Data
Oct. 22, 2014    (JP) .................................. 2014-215627

(51) Int. Cl.
*H01L 27/15* (2006.01)
*H01L 51/00* (2006.01)
(Continued)

(52) U.S. Cl.
CPC ............ *H01L 27/15* (2013.01); *C23C 16/453* (2013.01); *H01L 51/0072* (2013.01);
(Continued)

(58) Field of Classification Search
CPC . H01L 51/50; H01L 51/5032; H01L 51/5068; H01L 51/5268; H01L 25/048;
(Continued)

(56) References Cited

U.S. PATENT DOCUMENTS 5,686,360 A * 11/1997 Harvey, III ......... H01L 51/0097
438/126
2001/0050532 A1* 12/2001 Eida .................... H01L 51/5237
313/504
(Continued)

FOREIGN PATENT DOCUMENTS

JP        4186688 A     11/2004
JP     2011251460 A     12/2011
(Continued)

OTHER PUBLICATIONS

International Search Report dated Jan. 19, 2016 for PCT/JP2015/079576 and English translation.

*Primary Examiner* — Yosef Gebreyesus
(74) *Attorney, Agent, or Firm* — Lucas & Mercanti, LLP

(57) ABSTRACT

Provided is a light extraction substrate capable of achieving both light extraction efficiency and preservability. Before forming a cap layer, a step of reducing in-membrane water content such that the in-membrane water content of a layer formed between a gas barrier layer and the cap layer is less than $1.0 \times 10^{15}$/mg is performed. The in-membrane water content of less than $1.0 \times 10^{15}$/mg is maintained until at least a step of forming the cap layer after the step of reducing the in-membrane water content, and the cap layer is then formed through a dry process.

11 Claims, 7 Drawing Sheets

(51) Int. Cl.
   *C23C 16/453*   (2006.01)
   *H01L 29/49*    (2006.01)
   *C07D 403/14*   (2006.01)
   *C07D 209/82*   (2006.01)

(52) U.S. Cl.
   CPC ......... *C07D 209/82* (2013.01); *C07D 403/14* (2013.01); *H01L 29/4925* (2013.01)

(58) Field of Classification Search
   CPC . H01L 29/7869; C07D 209/82; C07D 403/14; C23C 16/453
   See application file for complete search history.

(56) References Cited

U.S. PATENT DOCUMENTS

| | | | | |
|---|---|---|---|---|
| 2008/0176041 | A1* | 7/2008 | Sato | H01L 51/0097 428/161 |
| 2008/0241471 | A1* | 10/2008 | Itai | H05B 33/04 428/138 |
| 2011/0024779 | A1* | 2/2011 | Nakamura | B82Y 20/00 257/98 |

FOREIGN PATENT DOCUMENTS

| | | |
|---|---|---|
| JP | 2012024933 A | 2/2012 |
| JP | 2012109255 A | 6/2012 |
| JP | 2014510373 A | 4/2014 |
| JP | 2015088322 A | 5/2015 |
| WO | 01/58221 A1 | 9/2001 |
| WO | 2015141242 A1 | 9/2015 |

\* cited by examiner

LIGHT EXTRACTION SUBSTRATE, METHOD FOR MANUFACTURING LIGHT EXTRACTION SUBSTRATE, ORGANIC ELECTROLUMINESCENT ELEMENT, AND METHOD FOR MANUFACTURING ORGANIC ELECTROLUMINESCENT ELEMENT

CROSS REFERENCE TO RELATED APPLICATION

This Application is a 371 of PCT/JP2015/079576 filed on Oct. 20, 2015 which, in turn, claimed the priority of Japanese Patent Application No. 2014-215627 filed on Oct. 22, 2014, both applications are incorporated herein by reference.

TECHNICAL FIELD

The present invention relates to a light extraction substrate, a method for manufacturing the light extraction substrate, an organic electroluminescence element, and a method for manufacturing the organic electroluminescence element.

BACKGROUND ART

In recent years, in the fields of electronic devices, long-term reliability, high degree of freedom in shape, and the capability of a curved surface display have been added to the demands for larger and lighter electronic devices. A resin base material such as transparent plastics has begun to be adopted instead of a glass substrate that is heavy, fragile, and that has difficulty in upsizing.

However, there is a problem that a resin base material such as transparent plastics has inferior gas barrier properties to a glass substrate. It is known that the use of a substrate having inferior gas barrier properties allows permeation of water vapor and oxygen, and thus deteriorates the function of, for example, an electronic device.

Accordingly, it has been generally known that there is used a gas barrier film obtained by formation of a film having gas barrier properties (gas barrier layer) on a resin base material. There is proposed the formation of a gas barrier layer including an organic layer arranged between, for example, an inorganic layer and an inorganic layer, on the resin base material (refer to, for example, Patent Literature 1).

Furthermore, in the organic electroluminescent (EL) element that is one of the electronic devices, it has been known that a configuration of providing a light extraction layer including a light scattering layer is effective in order to enhance the light emission efficiency.

However, when the gas barrier layer and a scattering layer are formed on a resin base material, the surface has unevenness, and when an organic functional layer having a light-emitting layer is formed thereon, the obtained element has problems that preservability under a high temperature and humidity is deteriorated, and short circuit (electric short-circuiting) becomes easily generated.

Furthermore, when the light extraction layer is formed on the resin base material, impurities remaining on the light extraction layer and the gas barrier layer produce bad influences on the organic functional layer. It has been primarily known that the organic EL element has high sensitivity to a slight amount of water/oxygen/other organic substances (remaining solvent, and the like), and thus there is also proposed a configuration of having a gas barrier layer just below the organic functional layer (refer to, for example, Patent Literature 2).

CITATION LIST

Patent Literature

PTL 1: Japanese Unexamined Patent Application Publication No. 2014-510373
PTL 2: Japanese Patent No. 4186688

SUMMARY OF INVENTION

Technical Problem

As described, it is difficult for the above described organic EL element to achieve both light extraction efficiency and preservability. The present invention can provide a light extraction substrate and an organic electroluminescence element capable of achieving both light extraction efficiency and preservability.

Solution to Problem

According to the method for manufacturing a light extraction substrate of the present invention, at least a gas barrier layer, a light scattering layer and a cap layer are provided on a resin base material. In addition, the method includes a step of reducing an in-membrane water content in which the in-membrane water content of a layer formed between a gas barrier layer and the cap layer is made to be less than $1.0 \times 10^{15}$/mg, before forming the cap layer. Furthermore, the method includes a step of: maintaining the in-membrane water content of less than $1.0 \times 10^{15}$/mg at least until the step of forming the cap layer, after the step of reducing the in-membrane water content; and forming the cap layer through a dry process.

Moreover, a method for manufacturing an organic EL element of the present invention includes a step of forming electrodes and a light-emitting unit on the above light extraction substrate.

The light extraction substrate of the present invention includes: a gas barrier layer provided on the resin base material; a light scattering layer provided on the gas barrier layer; and a cap layer formed on the light scattering layer by a dry process, wherein an in-membrane water content of a layer formed between a gas barrier layer and the cap layer is less than $1.0 \times 10^{15}$/mg.

Furthermore, the organic EL element of the present invention includes a light-emitting unit provided on the light extraction substrate and composed of an organic functional layer that is sandwiched by a pair of electrodes.

Advantageous Effects of Invention

According to the present invention, a light extraction substrate and an organic electroluminescence element which are capable of achieving both light extraction efficiency and preservability can be provided.

DESCRIPTION OF EMBODIMENTS

Figure 1:
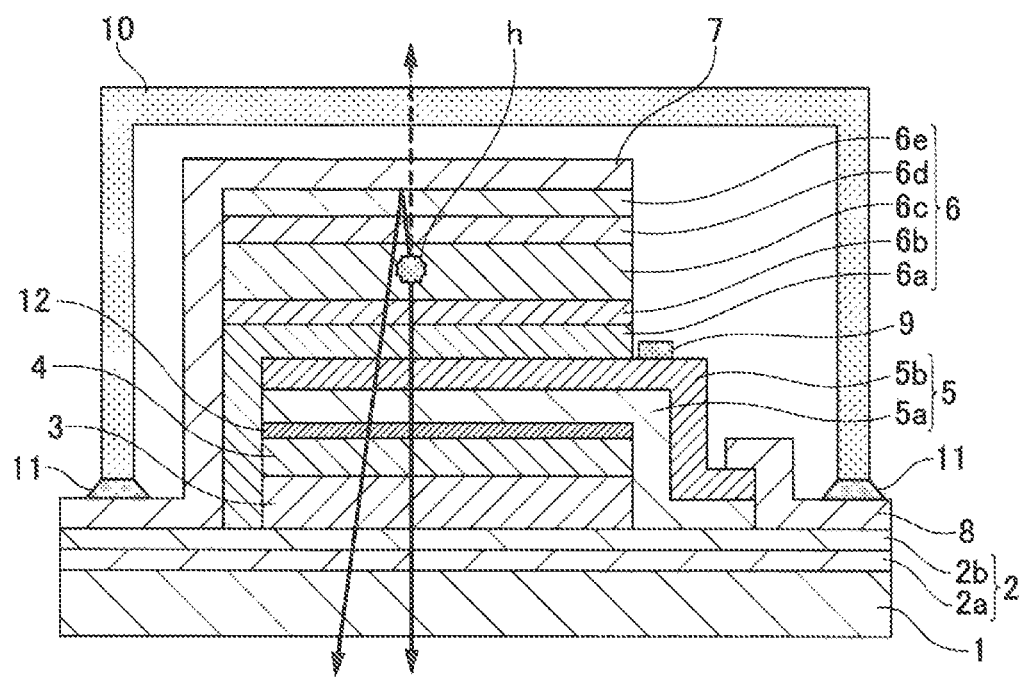
FIG. 1 is a cross-sectional view showing a schematic configuration of a light extraction substrate and an organic EL element.

Hereinafter, the embodiments for carrying out the present invention will be explained, but the present invention is not limited to the following examples.

Note that the explanation will be made in the following order.
1. Embodiment of light extraction substrate and organic electroluminescence element
2. Method for manufacturing light extraction substrate and organic electroluminescence element <1. Embodiment of Light Extraction Substrate and Organic Electroluminescence Element>

Hereinafter, specific embodiments of the light extraction substrate and the organic electroluminescence element will be explained.

[Summary of Light Extraction Substrate and Organic EL Element]

The light extraction substrate includes at least a resin base material and a gas barrier layer provided on the resin base material, and a cap layer formed through a dry process. Furthermore, at least a light scattering layer is provided between the gas barrier layer and the cap layer.

In addition, in the light extraction substrate, an in-membrane water content (hereinafter, referred to as simply in-membrane water content) of a layer formed between a gas barrier layer and the cap layer is less than $1.0\times10^{15}$/mg. Preferably, the above in-membrane water content is less than $1.0\times10^{14}$/mg.

The in-membrane water content is the number of water molecules contained in a membrane, and for example, is defined by counting of the number of water molecules, using a thermal desorption spectroscopy (TDS). The in-membrane water content is defined by a value with respect to a sample whose moisture is previously regulated, which has a known thickness, and which has an exact amount to be measured.

The organic EL element includes: the above light extraction substrate; a pair of electrodes composed of a transparent electrode provided on the light extraction substrate and a counter electrode; and a light-emitting unit provided between the electrodes and composed of an organic functional layer. In addition, even after the organic EL element is formed, the in-membrane water content (hereinafter, referred to as simply in-membrane water content) of the layer formed between the gas barrier layer and the cap layer in the light extraction substrate is less than $1.0\times10^{15}$/mg.

In order to achieve the in-membrane water content of less than $1.0\times10^{15}$/mg in the light extraction substrate and the organic EL element, the layer formed on the gas barrier layer is subjected to the treatment for reducing an in-membrane water content before forming the cap layer. The treatment for reducing an in-membrane water content can be carried out by a vacuum drying, a drying treatment under a non-oxygen atmosphere in an inert oven, and the like.

Furthermore, there is formed, as the cap layer, a film having gas barrier property by the use of a dry process. For example, it is preferable to form a cap layer containing a silicon nitride as a principal component. Note that the principal component means a component in which a proportion thereof in the whole components is highest.

Since the cap layer is formed through a dry process, there is no influence on the increase of the above in-membrane water content. Furthermore, by the formation of the cap layer through a dry process, it is possible to suppress penetration of water to the layer formed between the gas barrier layer and the cap layer. Namely, it is considered that there is almost no increase in the in-membrane water content of the layer formed between the gas barrier layer and the cap layer, after formation of the cap layer.

Furthermore, since, by the gas barrier layer and the cap layer, the penetration of water to the layer formed therebetween can be inhibited, even when electronic devices such as the organic EL element are formed on the light extraction substrate, the above in-membrane water content of the light extraction substrate can be maintained at a level of less than $1.0\times10^{15}$/mg.

Accordingly, after the above described treatment for reducing an in-membrane water content, by maintaining the in-membrane water content at a level of less than $1.0\times10^{15}$/mg until the formation of the cap layer, the final in-membrane water content after the completion of the light extraction substrate can be made to be at a level of less than $1.0\times10^{15}$/mg.

As a result, it is possible to reduce water contained in the layer formed between the gas barrier layer and the cap layer which is the reason of discharged gases from the light extraction substrate and affects adverse effect to electronic devices such as the organic EL element. Therefore, when the in-membrane water content is made to be at a level of less than $1.0\times10^{15}$/mg, particularly less than $1.0\times10^{14}$/mg, the discharged gases from the light extraction substrate are not almost generated, it is possible to reduce the adverse effect to the organic EL element due to the gases discharged from the light extraction substrate. Thereby, it is possible to enhance the light extraction efficiency by the light extraction substrate, and preservability and reliability of the organic EL element.

[Configurations of Light Extraction Substrate, Organic EL Element]

FIG. 1 shows the configurations of the light extraction substrate and the organic EL element according to the embodiment.

The light extraction substrate is constituted of a resin base material 1, a gas barrier layer 2 (first gas barrier layer 2a, second gas barrier layer 2b), a light scattering layer 3, a smoothing layer 4, and a cap layer 12. Furthermore, the organic EL element is constituted by provision of a light-emitting unit having an organic functional layer sandwiched by a transparent electrode 5 (underlayer 5a, conductive layer 5b) and a counter electrode 7, on the light extraction substrate.

In the organic EL element, an in-membrane water content of a layer formed between the gas barrier layer 2 and the cap layer 12 of the light extraction substrate is less than $1.0\times10^{15}$/mg. In the present embodiment, examples of the layer formed between the gas barrier layer 2 and the cap layer 12 are the light scattering layer 3 and the smoothing layer 4. The layer formed between the gas barrier layer 2 and the cap layer 12 may have at least the light scattering layer 3, the layer structure may be optionally changed. For example, it is possible to employ the configuration in which the smoothing layer 4 is formed on the light scattering layer 3 as in the present embodiment, or a configuration in which only the light scattering layer 3 is formed, or a configuration in which the light scattering layer 3 and the other layer are included.

In the light extraction substrate, the gas barrier layer 2 is formed all over the resin base material 1. And the light scattering layer 3, the smoothing layer 4, and the cap layer 12 are pattern-formed on the gas barrier layer 2 corresponding to the positions where the transparent electrode 5, the light-emitting unit 6, and the counter electrode 7 of the organic EL element are formed.

At the end of the transparent electrode 5 (conductive layer 5b), an extraction electrode 8 is provided. The transparent electrode 5 and an external electrode (not shown) are electrically connected via the extraction electrode. Furthermore, in order to make the electric resistance of the transparent electrode 5, an auxiliary electrode 9 is provided in contact with the conductive layer 5b of the transparent electrode 5.

Furthermore, the organic EL element having the configuration mentioned above is sealed by a sealing member 10 described below on the resin base material 1 in order to prevent the light-emitting unit 6 composed of the organic material or the like from degradation. The sealing member 10 is fixed to the resin base material 1 side via an adhesive 11. However, the terminals of the transparent electrode 5 (extraction electrode 8) and the counter electrode 7 are exposed from the sealing member 10 on the resin base material 1 so as to be electrically insulated by the light-emitting unit 6 to each other.

Note that the layer structure of the organic EL element is not limited, and may be a general layer structure. Here, the transparent electrode 5 acts as an anode (positive electrode), and the counter electrode 7 acts as a cathode (negative electrode). In this case, the light-emitting unit 6 has an exemplified configuration in which a positive hole injection layer 6a/a positive hole transport layer 6b/a light-emitting layer 6c/an electron transport layer 6d/an electron injection layer 6e are laminated in this order from the transparent electrode 5 side of the anode. Among them, it is necessary to have the light-emitting layer 6c configured using at least organic material. The positive hole injection layer 6a and the positive hole transport layer 6b may be provided as a positive hole transport-injection layer. The electron transport layer 6d and the electron injection layer 6e may be provided as an electron transport-injection layer. In addition, among these light-emitting units 6, for example, the electron injection layer 6e may be constituted of an inorganic material.

In the organic EL element, the part where only the light-emitting unit 6 is sandwiched by the transparent electrode 5 and the counter electrode 7 is the light-emitting region. In addition, the organic EL element is so configured as the bottom emission type where a generated light (hereinafter, referred to as emitted light h) is extracted at least from the side of the resin base material 1. In the present invention, the transparency (light transmittance) means that a light transmittance at 550 nm is 50% or more.

Here, the "light-emitting unit" is a light-emitting body (unit) which contains at least various organic compounds and is constituted of organic functional layers such as the light-emitting layer 6c, the positive hole transport layer 6b, and the electron transport layer 6d, and the like as main elements. The light-emitting body is sandwiched by a pair of electrodes composed of the anode and the cathode, and a positive hole (hole) supplied from the anode and an electron supplied from the cathode are recombined to emit a light in the light-emitting body. Note that the organic EL element may include a plurality of the light-emitting units corresponding to the desired colors of light.

Furthermore, in the light-emitting unit 6, layers such as a positive hole-blocking layer or an electron-blocking layer other than those layers may be laminated at necessary places. Moreover, the light-emitting layer 6c may have a configuration in which each light-emitting layer of each color which emits each light of each wavelength is included, and the light-emitting layer of each color is laminated via a non-luminescent auxiliary layer. The auxiliary layer may be act as the positive hole-blocking layer or the electron-blocking layer. Furthermore, the counter electrode 7 of the cathode may also have corresponding laminated structures. In the configuration, only the part where the light-emitting unit 6 is sandwiched by the transparent electrode 5 and the counter electrode 7 is the light-emitting region in the organic EL element.

The organic EL element may be an element of so-called Tandem where in which a plurality of the light-emitting unit 6 including at least one light-emitting layer is laminated. A representative element configuration having a tandem structure is as follows.

Anode/first light-emitting unit/intermediate connector layer/second light-emitting unit/intermediate connector layer/third light-emitting unit/cathode Here, the above first light-emitting unit, second light-emitting unit, and third light-emitting unit may be the same or different. In addition, two light-emitting units may be the same and the remaining one may be different.

Two or more the light-emitting units 6 may be directly laminated or may be laminated via the intermediate connector layer.

Generally, the intermediate connector layer is also referred to as an intermediate electrode, an intermediate conductive layer, a charge generating layer, an electron extraction layer, a connecting layer, or an intermediate insulation layer, and a known material configuration can be used for the intermediate connector layer as long as the layer has a function of supplying an electron to an adjacent layer on the anode side, and of supplying a positive hole to an adjacent layer on the cathode side. Examples of materials used in the intermediate layer include an electrically conductive inorganic compound such as ITO (indium tin oxide), IZO (indium zinc oxide), $ZnO_2$, TiN, ZrN, HfN, $TiO_x$, $VO_x$, CuI, InN, GaN, $CuAlO_2$, $CuGaO_2$, $SrCu_2O_2$, $LaB_6$, $RuO_2$, or Al, a two-layered film such as $Au/Bi_2O_3$, a multi-layered film such as $SnO_2/Ag/SnO_2$, $ZnO/Ag/ZnO$, $Bi_2O_3/Au/Bi_2O_3$, $TiO_2/TiN/TiO_2$, or $TiO_2/ZrN/TiO_2$, a fullerene such as $C_{60}$, and an electrically conductive organic layer such as oligothiophene, metal phthalocyanine, metal-free phthalocyanine, metal porphyrin, or metal-free porphyrin, and the like, but is not limited thereto.

Preferred configuration of the light-emitting unit 6 is, for example, one in which the anode and the cathode are omitted from the representative element configuration, and the like, and is not limited thereto.

Examples of the tandem type organic EL element include elemental configurations and constituent materials described in U.S. Pat. No. 6,337,492, U.S. Pat. No. 7,420,203, U.S. Pat. No. 7,473,923, U.S. Pat. No. 6,872,472, U.S. Pat. No. 6,107,734, U.S. Pat. No. 6,337,492, WO 2005/009087, Japanese Patent Laid-Open No. 2006-228712, Japanese Patent Laid-Open No. 2006-24791, Japanese Patent Laid-Open No. 2006-49393, Japanese Patent Laid-Open No. 2006-49394, Japanese Patent Laid-Open No. 2006-49396, Japanese Patent Laid-Open No. 2011-96679, Japanese Patent Laid-Open No. 2005-340187, JP Patent No. 4711424, JP Patent No. 3496681, JP Patent No. 3884564, JP Patent No. 4213169, Japanese Patent Laid-Open No. 2010-192719, Japanese Patent Laid-Open No. 2009-076929, Japanese Patent Laid-Open No. 2008-078414, Japanese Patent Laid-Open No. 2007-059848, Japanese Patent Laid-Open No. 2003-272860, Japanese Patent Laid-Open No. 2003-045676, WO 2005/094130, and the like, but are not limited thereto.

Hereinafter, the main configuration and the manufacturing method of the light extraction substrate and the organic EL element will be explained.

[Resin base Material]

The resin base material 1 of the light extraction substrate can include, for example, a resin film, and the like, but is not limited thereto. A preferable resin base material 1 can include a transparent resin film, and the like.

Examples of the resin film include polyesters such as polyethylene terephthalate (PET) and polyethylene naphthalate (PEN), polyethylene, polypropylene, cellulose esters or derivative thereof such as cellophane, cellulose diacetate, cellulose triacetate (TAC), cellulose acetate butylate, cellulose acetate propionate (CAP), cellulose acetate phthalate and cellulose nitrate, polyvinylidene chloride, polyvinyl alcohol, polyethylene vinyl alcohol, syndiotactic polystyrene, polycarbonate, norbornen resin, polymethylpenten, polyether ketone, polyimide, polyether sulphone (PES), polyphenylene sulfide, polysluphones, polyether imide, polyether ketone imide, polyamide, fluoro resin, Nylon, polymethyl methacrylate, acryl or polyallylates, cycloolefins-based resins such as Alton (commercial name of JSR) or APEL (commercial name of Mitsui Chemicals), and the like.

[Gas Barrier Layer]

It is preferable that the gas barrier layer 2 is constituted of a first gas barrier layer 2a and a second gas barrier layer 2b which have different compositions or distributions of constituent elements from each other. When the gas barrier layer 2 is constituted by at least two gas barrier layers which have different compositions or distributions of constituent elements, it is possible to efficiently prevent the permeation of oxygen and water vapor. Note that the gas barrier layer 2 may be formed in mono-layer form as long as the layer can efficiently prevent the permeation of oxygen and water vapor.

The gas barrier layer 2 is preferably a gas barrier film (also referred to as gas barrier membrane, etc.) having a water vapor permeability (25±0.5° C., relative humidity 90±2% RH) measured by the method in accordance with JIS-K-7129-1992 of 0.01 g/(m²·24 h) or less. Furthermore, the film preferably has an oxygen permeability measured by the method in accordance with JIS-K-7126-1987 of $1\times10^{-3}$ ml/(m²·24 h·atm) or less, and a water vapor permeability of $1\times10^{-5}$ g/(m²·24 h) or less.

In a case where the gas barrier layer 2 is composed of two or more layers, at least one gas barrier layer preferably contains silicon dioxide which is a reaction product of an inorganic silicon compound. Furthermore, at least one gas barrier layers preferably contains a reaction product of an organosilicon compound. Namely, at least one gas barrier layer preferably contains an element derived from the organosilicon compound, for example, oxygen, silicon, carbon, and the like, as a constituent element.

The composition and distribution state within the gas barrier layer 2 of the elements constituting the gas barrier layer 2 may be uniform, or different in the direction of layer thickness. As a method for making the composition and distribution state of the constituent elements different from each other, it is preferable to make the formation method and the formation material of the gas barrier layer 2 different from each other, as described later.

In addition, a water vapor permeability Wg of the gas barrier layer 2, a water vapor permeability Ws of the light scattering layer 3 and a water vapor permeability Wf of the cap layer 12 preferably satisfy the following equation.

$$Wg \leq Wf < Ws$$

[First Gas Barrier Layer]

The elements which compose the first gas barrier layer 2a may at least contain the elements compose a compound which prevents the permeation of oxygen and water vapor, and have a different constitution ratio of elements from the second gas barrier layer 2b described below.

For example, the first gas barrier layer 2a may be provided as a layer which contains silicon, oxygen, and carbon on one surface of the resin base material 1. In this case, in the distribution curves of these elements obtained through element distribution measurement for the first gas barrier layer 2a in the depth direction by the use of X-ray photoelectron spectroscopy, it is preferable to satisfy all of the requirements (i) to (iv) described below, from the viewpoint of enhancement of gas barrier property.

(i) The atomic percentage of silicon, the atomic percentage of oxygen, and the atomic percentage of carbon have the relationship indicated below in an area covering 90% or more of the distance from the surface across the thickness of the first gas barrier layer 2a:

(atomic percentage of carbon)<(atomic percentage of silicon)<(atomic percentage of oxygen).

(ii) The carbon distribution curve has at least two local extremum points.

(iii) The absolute value of the difference between the greatest value and the smallest value of the atomic percentage of carbon in the carbon distribution curve is 5 at % or more.

(iv) In the oxygen distribution curve, the value of the maximum point of the oxygen distribution curve closest to the surface of the first gas barrier layer 2a at the resin base material 1 side is the largest of the values of the maximum points of the oxygen distribution curve of the first gas barrier layer 2a.

The first gas barrier layer 2a is preferably a thin film formed on the resin base material 1 through plasma enhanced chemical vapor deposition (plasma CVD) method in which by the use of a strip of a flexible resin base material 1, the resin base material 1 is conveyed between and in contact with a pair of deposition rollers and is exposed to plasma discharge while a deposition gas is supplied between the deposition rollers.

Note that the above described local extremum point refers to a maximum point or a minimum point of the atomic percentage of each element in a certain distance from the surface of the first gas barrier layer 2a in the thickness direction of the first gas barrier layer 2a.

(Definition of Maximum Point and Minimum Point)

The maximum point means a point at which the atomic percentage of the element changes from an increase to a decrease when the distance from the surface of the first gas barrier layer 2a varies, and also means a point from which the atomic percentage of the element becomes smaller by 3 at % or more, than the value of the atomic percentage of the element at that point, when the distance from the surface of the first gas barrier layer 2a in the thickness direction of the first gas barrier layer 2a varies by 20 nm.

Furthermore, the minimum point means a point at which the atomic percentage of the element changes from a decrease to an increase when the distance from the surface of the first gas barrier layer 2a varies, and also means a point from which the atomic percentage of the element becomes larger by 3 at % or more, than the value of the atomic percentage of the element at that point, when the distance from the surface of the first gas barrier layer 2a in the thickness direction of the first gas barrier layer 2a varies by 20 nm.

(Relationship Among Average, Greatest Value, and Smallest Value of Atomic Percentage of Carbon)

The average atomic percentage of carbon in the entire first gas barrier layer 2a is preferably within the range of 8 to 20 at % in view of flexure resistance, more preferably 10 to 20 at %. When the atomic percentage of carbon is within the above range, it is possible to provide the first gas barrier layer 2a having enough gas barrier properties and flexure resistance.

Furthermore, the absolute value of the difference between the greatest value and the smallest value of the atomic percentage of carbon on the carbon distribution curve of such a first gas barrier layer 2a is preferably 5 at % or more. In addition, in such a first gas barrier layer 2a, the absolute value of the difference between the greatest value and the smallest value of the atomic percentage of carbon is more preferably 6 at % or more, particularly preferably 7 at % or more. When the absolute value is 3 at % or more, the barrier properties are satisfactory at the bending the first barrier layer 2a.

(Positions of Local Extremum Points and Relationship Between Greatest Value and Smallest Value of Atomic Percentage of Oxygen)

In order to prevent the permeation of water molecules from the resin base material 1 side, in the oxygen distribution curve of the first gas barrier layer 2a, it is preferable that the value of the maximum point of the oxygen distribution curve closest to the surface of the first gas barrier layer 2a at the resin base material 1 side is the largest of the values of the maximum points of the oxygen distribution curve of the first gas barrier layer 2a.

Figure 2:
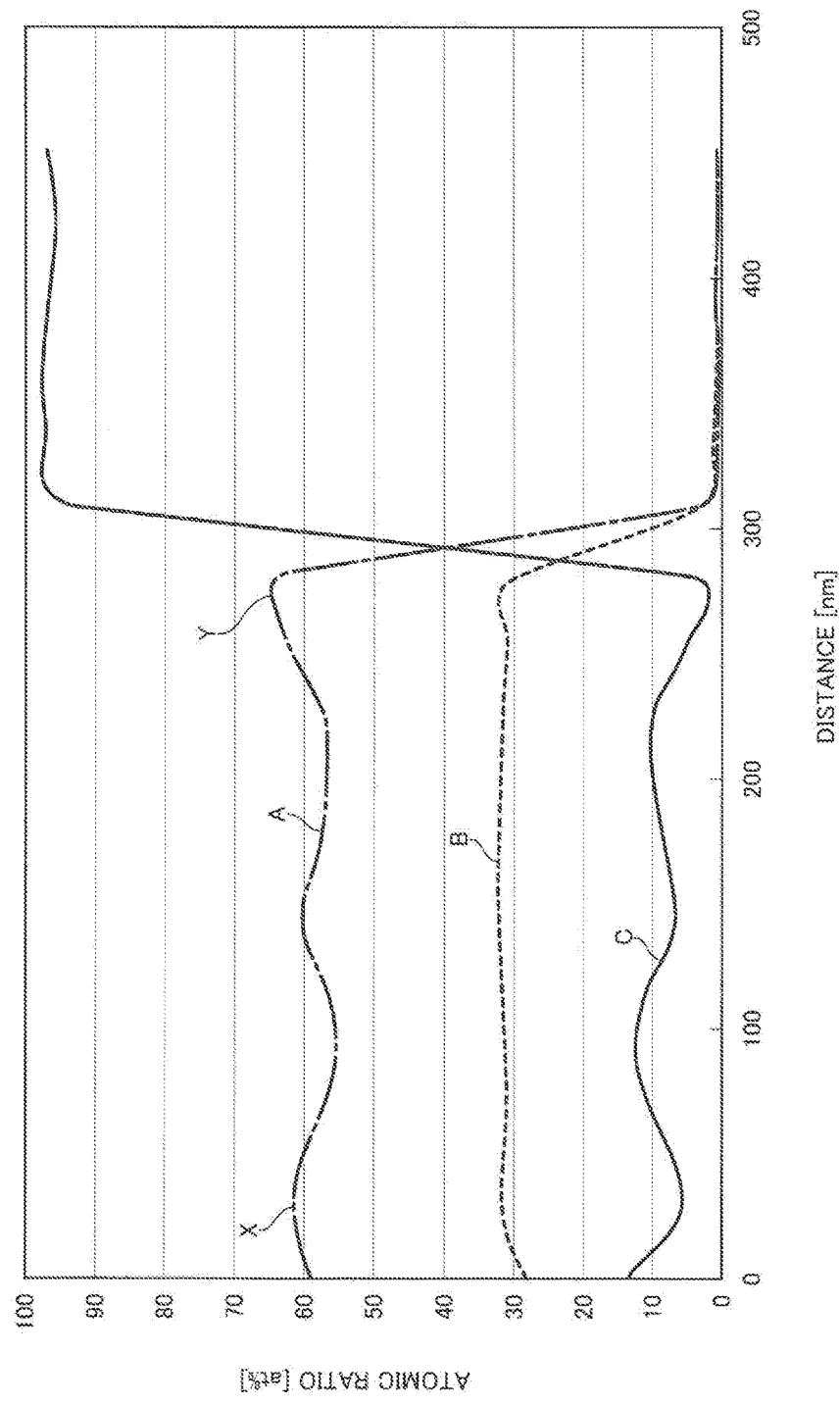
FIG. 2 is a graph showing each element profile of a gas barrier layer in the thickness direction due to composition analysis in the depth direction by the use of the XPS.

FIG. 2 is a graph illustrating depth profiles of elements in the thickness direction of the first gas barrier layer 2a according to the XPS depth profile (distribution of depth direction).

In FIG. 2, the oxygen distribution curve is designated by A, the silicon distribution curve is designated by B, and the carbon distribution curve is designated by C.

The atomic percentage of each element continuously vary between the interface of the first gas barrier layer 2a at the light-emitting unit 6 side (distance being 0 nm, herein after, referred to as "surface") and the interface of the resin base material 1 side of the first barrier layer (distance being about 300 nm, herein after, referred to as "back surface"), and in order to prevent the permeation of water molecules from the resin base material 1, the value of the atomic percentage of oxygen should be Y>X, where X is the atomic percentage of oxygen at a maximum point closest to the surface of the first gas barrier layer 2a on the oxygen distribution curve A, and Y is the atomic percentage of oxygen at a maximum point closest to the back surface of the first barrier layer 2a.

The atomic percentage Y of oxygen at the maximum point of the oxygen distribution curve closest to the back surface of the first gas barrier layer 2a is preferably 1.05 times or more the atomic percentage X of oxygen at the maximum point of the oxygen distribution curve closest to the surface of the first gas barrier layer 2a. Namely, it is preferred that $1.05 \leq Y/X$. The upper limit may not be particularly limited, and the upper limit is preferably within the range of $1.05 \leq Y/X \leq 1.30$, more preferably within the range of $1.05 \leq Y/X \leq 1.20$. When being within the range, the permeation of water molecules can be prevented without degradation of the gas barrier properties under high temperature and high humidity, and also it is preferable from the points of productivity and cost.

In the oxygen distribution curve of the first gas barrier layer 2a, the absolute value of the difference of the greatest value and the smallest value of the atomic percentage of oxygen is preferably 5 at % or more preferably 6 at % or more, particularly preferably 7 at % or more.

(Relationship Between Greatest Value and Smallest Value of Atomic Percentage of Silicon)

The absolute value of the difference between the greatest value and the smallest value of the atomic percentage of silicon on the silicon distribution curve of the first gas barrier layer 2a is preferably less than 5 at %, more preferably less than 4 at %, particularly preferably less than 3 at %. When the absolute value is within the above range, the obtained first gas barrier layer 2a has an enough gas barrier property and the gas barrier layer 2 has an enough mechanical strength.

(Analysis of Composition in the Depth Direction of Gas Barrier Layer by XPS)

The carbon distribution curve, the oxygen distribution curve, and the silicon distribution curve in the direction of thickness (depth) of the gas barrier layer 2 can be prepared through the so-called XPS depth profiling (distribution in the depth direction) in which the interior of the specimen is exposed in sequence for analysis of the surface composition through a combination of X-ray photoelectron spectroscopy and ion-beam sputtering using a noble gas such as argon. The distribution curve obtained by the XPS depth profiling has, for example, a vertical axis representing the atomic percentage (unit: at %) of the element and a horizontal axis representing the etching time (sputtering time).

Note that, in the distribution curve of the element versus the etching time of the horizontal axis, the etching time correlates significantly with the distance from the surface of the gas barrier layer 2 in the thickness direction. Therefore, "the distance from the surface of the gas barrier layer in the thickness direction of the gas barrier layer" can be the distance from the surface of the gas barrier layer 2 calculated on the basis of the relationship between the etching rate and etching time used in the XPS depth profiling.

In addition, as the method of spattering at the XPS depth profiling, it is preferable to employ an ion-beam sputtering with a noble gas such as argon (Art) as the ionic specie and an etching speed (etching rate) is set to 0.05 nm/sec (equivalent to a value for a thermally-oxidized $SiO_2$ film).

Furthermore, in view of forming a gas barrier layer having a uniform surface and superior gas barrier properties all over the surface of the first barrier layer 2a, it is preferable that the first gas barrier layer 2a is substantially uniform in the surface direction (the direction parallel to the surface of the first gas barrier layer 2a).

The first gas barrier layer 2a being substantially uniform in the surface direction means that, when the distribution curve of oxygen and the distribution curve of carbon are plotted as to any two points on the surface of the first gas barrier layer 2a obtained by the XPS depth profiling, the carbon distribution curves for the two points contain the same number of local extremum points, and that the absolute values of the differences between the greatest value and the smallest value of the atomic percentage of carbon of the carbon distribution curves are identical or have a difference within 5 at % or less.

The gas barrier layer 2 preferably includes at least one first gas barrier layer 2a that satisfies all of conditions (i) to (iv) described above, and may include two or more layers that satisfy the conditions.

Furthermore, in a case where two or more first gas barrier layers 2a are provided, the plurality of first gas barrier layers 2a may be composed of an identical material or different materials. Moreover, the first gas barrier layer 2a may be disposed on one of the sides of the resin base material 1 or on both sides of the resin base material 1.

In addition, in the distribution curve of silicon, the distribution curve of oxygen, and the distribution curve of carbon, if the atomic percentage of silicon, the atomic percentage of oxygen, and the atomic percentage of carbon satisfy the condition represented by the condition (i) in the region corresponding to 90% or more of the thickness of the first gas barrier layer 2a, the atomic percentage of silicon in the first gas barrier layer 2a is preferably within the range of 25 to 45 at %, more preferably within the range of 30 to 40 at %.

Furthermore, the atomic percentage of oxygen in the first gas barrier layer 2a is preferably within the range of 33 to 67 at %, more preferably within the range of 45 to 67 at %.

Moreover, the atomic percentage of carbon in the first gas barrier layer 2a is preferably within the range of 3 to 33 at %, more preferably within the range of 3 to 25 at %.

(Thickness of First Gas Barrier Layer)

The thickness of the first gas barrier layer 2a is preferably within the range of 5 to 3000 nm, more preferably within the range of 10 to 2000 nm, more preferably within the range of 100 to 1000 nm, particularly preferably within the range of 300 to 1000 nm. When the thickness of the first gas barrier layer 2a is within the above range, the first gas barrier layer has the excellent gas barrier properties such as the oxygen gas barrier property and the water vapor barrier property, and does not lower the gas barrier properties even after bending.

(Method for Forming First Gas Barrier Layer)

The first gas barrier layer 2a is preferably a layer formed by the plasma enhanced chemical vapor deposition (plasma CVD method). More specifically, the first gas barrier layer 2a formed by the plasma CVD method is formed by the plasma CVD method in which the resin base material 1 is conveyed in contact with a pair of deposition rollers and is exposed to plasma discharge while deposition gas is supplied between the deposition rollers.

In addition, during the discharge between the pair of deposition rollers like this, it is preferable that the polarity of the pair of deposition rollers is alternately inverted. The deposition gas used in the plasma CVD method preferably includes an organosilicon compound and oxygen. The content of the oxygen in the deposition gas to be supplied is preferably equal to or less than a theoretical quantity required for the complete oxidation of the entire quantity of the organosilicon compound in the deposition gas. The first gas barrier layer 2a is preferably a layer formed on the resin base material 1 by a continuous deposition process. The plasma CVD may be the plasma CVD of the Penning discharge plasma system.

In order to form a layer having an atomic percentage of carbon that has a concentration gradient and continuously varies in the layer like the first gas barrier layer 2a, it is preferable to generate the plasma discharge in the space between a plurality of the deposition rollers when generating the plasma in the plasma CVD, and it is preferable to use the pair of the deposition rollers and to generate plasma by an electric discharge in the space between the pair of the deposition rollers which are conveying the strip of the resin base material 1 while in contact with each of the pair of the deposition rollers.

When using the pair of the deposition rollers and generating plasma by an electric discharge in the space between the pair of the deposition rollers which are conveying the strip of the resin base material 1 while in contact with each of the pair of the deposition rollers, since the distance between the resin base material 1 and the position of the plasma discharge between the deposition rollers is changed, it is possible to form the first gas barrier layer 2a having an atomic percentage of carbon that has a concentration gradient and continuously varies within the layer.

Furthermore, since it is possible, at the film formation, to film-forming on the surface of the resin base material 1 which is carried on one deposition roller, and at the same time, to film-forming on the surface of the resin base material 1 which is carried on another deposition roller, the film formation can be achieved efficiently, and thus a film-forming rate can be increased twice, and furthermore, since it is possible to form the film having the same configuration, the local extremum points in the carbon distribution curves can at least be doubled, and the first gas barrier layer 2a that satisfies all of the conditions (i) to (iv) can be efficiently formed.

In addition, it is preferable to produce the gas barrier film by forming the gas barrier layer 2 on the surface of the resin base material 1 according to the roll-to-roll system from the viewpoint of productivity.

Figure 3:
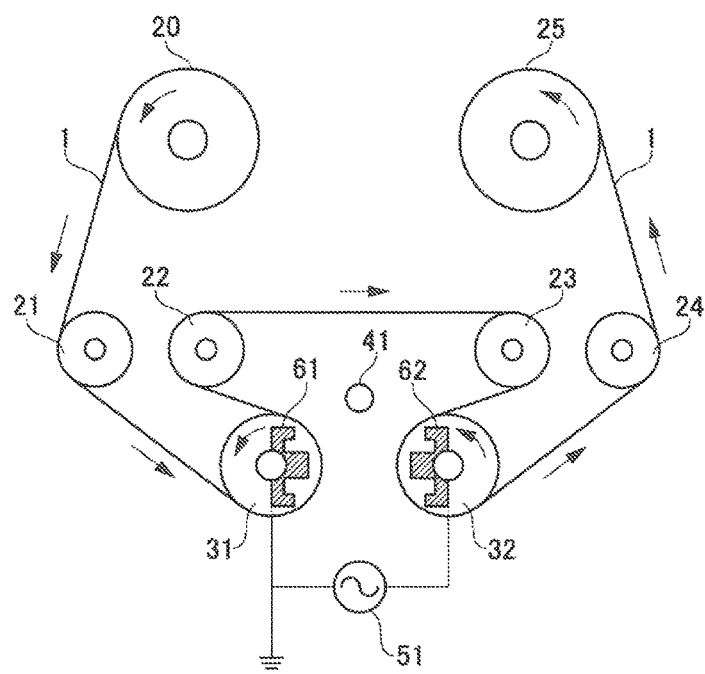
FIG. 3 is a schematic view showing one example of manufacturing apparatuses of the gas barrier film.

Any apparatus can be used for the production of the gas barrier film by the plasma CVD method, it is preferable that the apparatus includes at least a pair of deposition rollers and a plasma power source, and is capable of discharging in the space between the pair of the deposition rollers, and, for example, by employing the manufacturing apparatus illustrated in FIG. 3, the gas barrier film can be formed by the plasma CVD method in the roll-to-roll process system.

Hereinafter, a method for forming the first gas barrier layer 2a will be explained in detail by referring to FIG. 3. FIG. 3 is a schematic view showing one preferred example of the apparatus which is suitable to form the first gas barrier layer 2a on the resin base material 1.

The manufacturing apparatus shown in FIG. 3 includes a delivery roller 20, conveyer rollers 21, 22, 23, and 24, deposition rollers 31 and 32, a gas inlet 41, a power source 51 for plasma generation, magnetic-field generators 61 and 62 disposed inside the deposition rollers 31 and 32, and a reeling roller 25.

In addition, the manufacturing apparatus includes a vacuum chamber (not shown) that accommodates at least the deposition rollers 31 and 32, the gas inlet 41, the power source 51 for plasma generation, and the magnetic-field generators 61 and 62 made of permanent magnets. Furthermore, in the manufacturing apparatus, the vacuum chamber is connected to a vacuum pump (not shown), and the vacuum pump can appropriately adjust the pressure in the vacuum chamber.

In the manufacturing apparatus, in order that the pair of the deposition rollers (deposition roller 31 and deposition roller 32) can function as a pair of counter electrodes, each of the deposition rollers is connected to the power source 51 for plasma generation. Thereby, in the manufacturing apparatus, electric power can be supplied from the power source 51 for plasma generation and discharged in the space between the deposition roller 31 and the deposition roller 32, and this can generate plasma in the space between the deposition roller 31 and the deposition roller 32.

Note that, when the deposition roller 31 and the deposition roller 32 are utilized as electrodes, the material and design thereof may be appropriately selected so as to be suitable to electrodes. In addition, in the manufacturing apparatus, the pair of the deposition rollers (deposition rollers 31 and 32) are preferably disposed such that the central axes of the rollers are substantially parallel to each other on a single plane. Such arrangement of the pair of the deposition rollers (deposition rollers 31 and 32) can double the deposition rate and at least double the number of local extremum points in the carbon distribution curve because film with an identical structure can be formed.

In addition, in the deposition roller 31 and the deposition roller 32, magnetic-field generators 61 and 62 are provided so as to be fixed without rotating even when the deposition rollers.

The deposition roller 31 and the deposition roller 32 may be any appropriate known roller. From the viewpoint that a thin film ca be formed efficiently, it is preferable that the deposition rollers 31 and 32 having the same diameter are used. The diameter of the deposition rollers 31 and 32 is preferably within the range of 300 to 1000 mmφ, more preferably within the range of 300 to 700 mmφ, in view of the discharge conditions and the space in the chamber, and the like. When the diameter is 300 mmφ or more, since the plasma discharge space would not be decreased, the productivity is not so lowered, and furthermore, since the total heat due to the plasma discharge is prevented from being applied to the film in a short time, it is possible to reduce damage to the resin base material 1, and it is preferable. On the other hand, when the diameter is 1000 mmφ or less, it is possible to maintain the practical property in the mechanical design including uniformity of the plasma discharge space, and it is preferable.

In addition, the delivery roller 20 and the conveyer rollers 21, 22, 23 and 24 to be used in the manufacturing apparatus may be any appropriate known rollers. Furthermore, the reeling roller 25 is not particularly limited, even if the resin base material 1 (gas barrier film) where the first gas barrier layer 2a is formed can be reeled, and may also be any appropriate known roller.

The gas inlet 41 may be any appropriate inlet that can supply or discharge a raw material gas at a predetermined rate.

The power source 51 for plasma generation may be any appropriate power source for a known plasma generator. The power source 51 for plasma generation supplies power to the deposition roller 31 and the deposition roller 32 which are connected thereto, and thus they can be used as the counter electrodes for electric discharge.

The power source 51 for plasma generation like this is preferably a source (AC source, etc.) that can alternatively invert the polarities of the pair of the deposition rollers so as to efficiently perform plasma CVD method. In addition, it is preferable to be an applied power within the range of 100 W to 10 kW and an AC frequency within the range of 50 Hz to 500 kHz.

The magnetic-field generators 61 and 62 may be any appropriate known magnetic-field generator.

By the use of the manufacturing apparatus shown in FIG. 3 like this, the first gas barrier layer 2a can be manufactured in which the appropriate adjustments such as, for example, the type of raw material gas, the electric power of the electrode drum in the plasma generator, the pressure in the vacuum chamber, the diameter of the deposition rollers, and the conveying rate of the resin base material 1.

Namely, by the use of the manufacturing apparatus shown in FIG. 3, the first gas barrier layers 2a can be formed by the plasma CVD method on the surface of the resin base material 1 on the deposition roller 31 and the surface of the resin base material 1 on the deposition roller 32 by, while supplying a deposition gas (raw material gas, etc.) into the vacuum chamber, generating the plasma discharge between the pair of the deposition rollers (deposition rollers 31, 32) so as to decompose the deposition gas (raw material gas, etc.) by the plasma.

Note that, in such a deposition process, the resin base material 1 is conveyed by the delivery roller 20 and the deposition roller 31, and the like, and the first gas barrier layer 2a is formed on the surface of the resin base material 1 through the continuous deposition process of the roll-to-roll system.

The first gas barrier layer 2a is preferably that the value of the maximum point of the oxygen distribution curve closest to the surface of the first gas barrier layer 2a at the resin base material 1 side is the largest of the values of the maximum points of the oxygen distribution curve of the first gas barrier layer 2a in the distribution curve of oxygen (iv).

In addition, it is preferable, as the atomic percentage of oxygen, that the atomic percentage of oxygen at the maximum point of the oxygen distribution curve closest to the surface of the first gas barrier layer 2a at the resin base material 1 side is preferably 1.05 times or more the atomic percentage of oxygen at the maximum point of the oxygen distribution curve closest to the surface of the first gas barrier layer 2a of the second bas barrier layer 2b side.

In this way, the method for forming the first gas barrier layer 2a having a predetermined distribution of atomic percentage of oxygen is not particularly limited, and may be a method for varying the concentration of the deposition gas during deposition, a method for changing the position of the gas inlet 41, a method for supplying the gas to multiple inlets, a method for controlling the flow of the gas with a baffle (shielding) plate, or the like near the gas inlet 41, a method for performing plasma CVD multiple times at different concentrations of the deposition gas, and the like, and, a method for performing plasma CVD by changing the position of the gas inlet 41 near either of the deposition roller 31 or the deposition roller 32 is preferable, because of easiness and good reproducibility.

Figure 4:
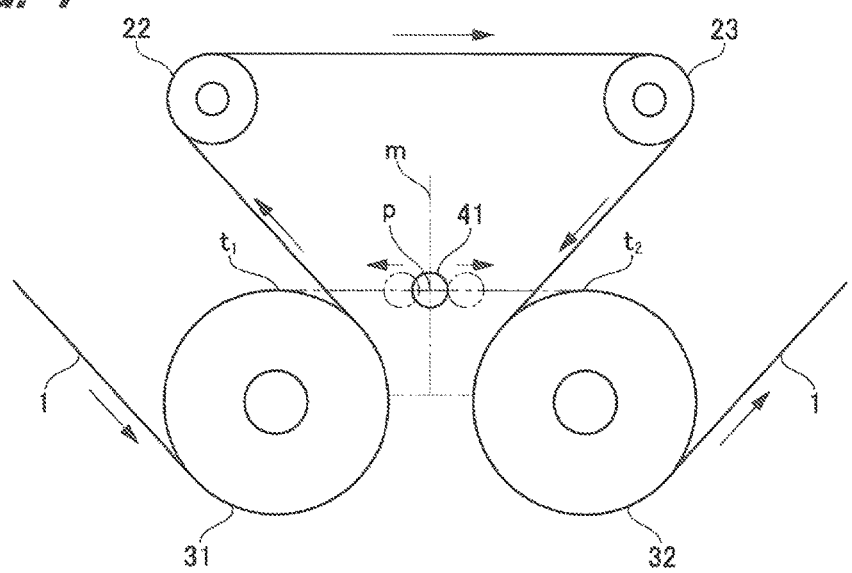
FIG. 4 is a schematic view showing position setting of the gas inlet.

FIG. 4 is a schematic view explaining the movement of the position of the gas inlet 41 in the CVD apparatus.

When assuming the distance between the gas inlet 41 and the deposition roller 31 or the deposition roller 32 to be 100%, the gas inlet 41 can be closed toward the deposition roller 31 or 32 within the range of 5 to 20% from the perpendicular bisector m of the line segment connecting the deposition rollers 31 and 32 so as to control the values of the local extremum points of the oxygen distribution curve to satisfy the condition of the local extremum point.

Namely, it means that, when assuming that the distance $(t_1-p)$ or the distance $(t_2-p)$ to be 100%, where the distance is from the point p on the perpendicular bisector m of the line segment connecting the deposition rollers 31 and 32 to the point $t_1$ or point $t_2$, the gas inlet 41 is closed parallel toward the deposition rollers within the range of 5 to 20% from point p.

In this case, the value of the local extremum point of the oxygen distribution curve can be controlled by the distance of the movement of the gas inlet 41. For example, in order to increase the value of local extremum point of the oxygen distribution curve of the surface of the first gas barrier layer 2a which is the closest to the resin base material 1 side, the gas inlet 41 can be closed toward the deposition roller 31 or 32 within the moving distance of near 20%.

The moving range of the gas inlet 41 is preferably within the range of 5 to 20%, more preferably 5 to 15%, and when the movement is within the above range, there is not yielded unevenness in the oxygen distribution curve and other element distribution curves in the surface, and it is possible to reproduce well the predetermined distribution uniformly.

FIG. 2 shows the profile of each element in the thickness direction obtained by the XPS depth profile of the layer which is formed by moving the gas inlet 41 toward the deposition roller 31 by 5%, in the first gas barrier layer 2a.

Figure 5:
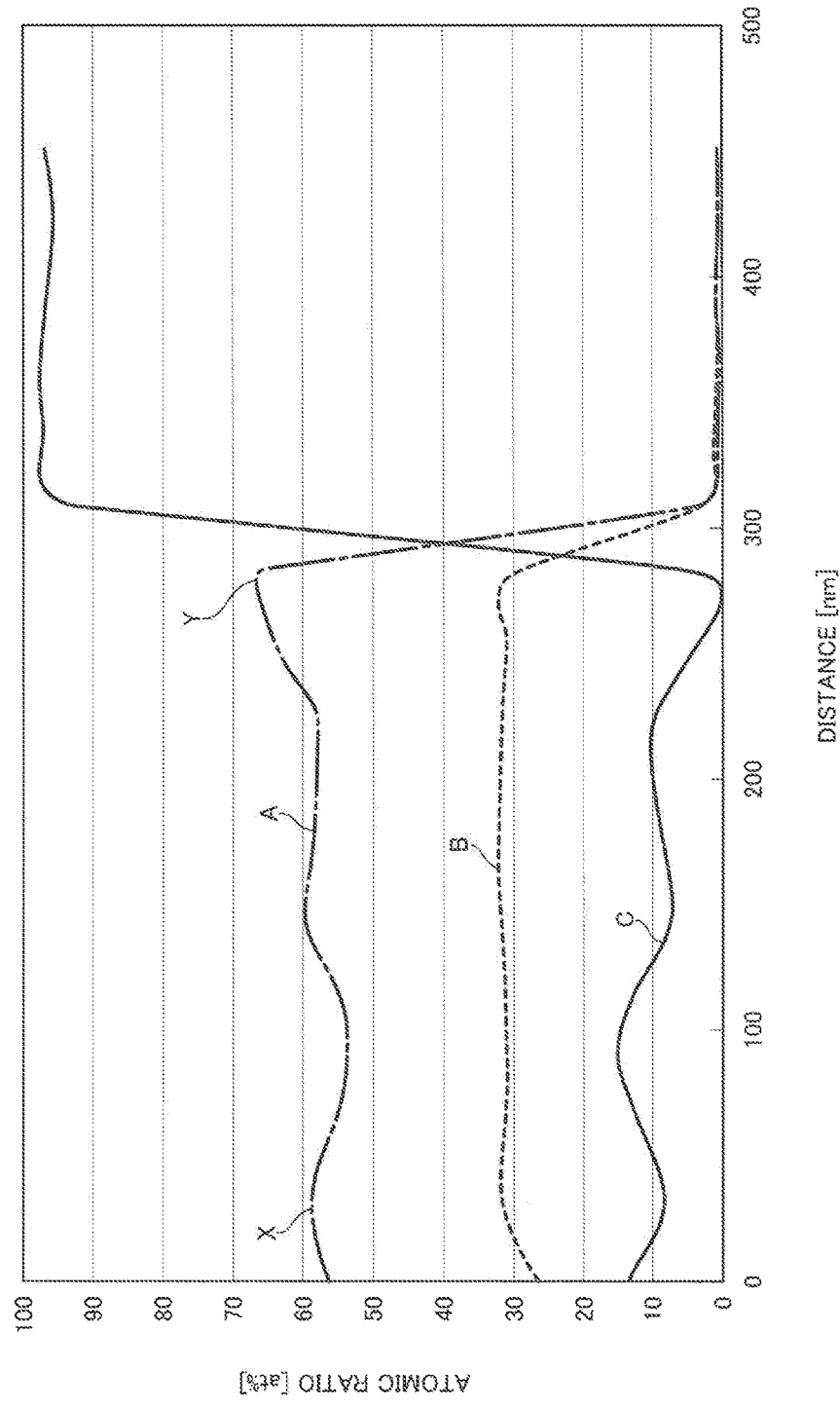
FIG. 5 is a graph showing each element profile of the gas barrier layer in the thickness direction due to composition analysis in the depth direction by the use of the XPS.

Furthermore, FIG. 5 shows the profile of each element in the thickness direction obtained by the XPS depth profile of the layer which is formed by moving the gas inlet 41 toward the deposition roller 32 by 10%.

In both FIG. 2 and FIG. 5, when X is the atomic percentage of oxygen at a maximum point closest to the surface of the first gas barrier layer 2a on the oxygen distribution curve A, and Y is the atomic percentage of oxygen at a maximum point closest to the back surface of the first barrier layer 2a, the relation of Y>X is satisfied.

Figure 6:
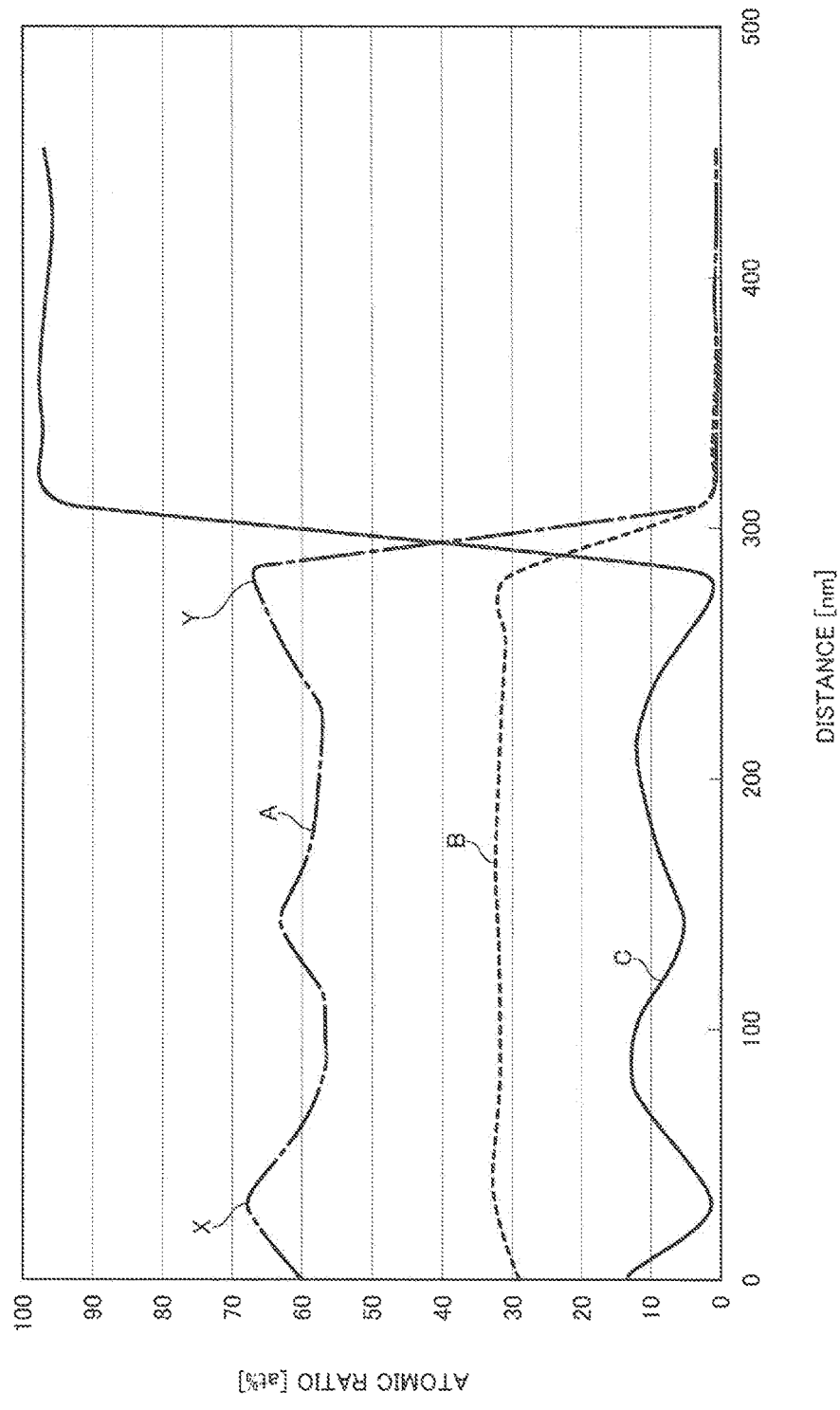
FIG. 6 is a graph showing each element profile of the gas barrier layer in the thickness direction due to composition analysis in the depth direction by the use of the XPS.

In addition, FIG. 6 shows the profile of each element obtained by the XPS depth profile of the gas barrier layer in the thickness direction. The gas barrier layer is formed by fixing the gas inlet 41 on the perpendicular bisector m of the line segment connecting the deposition rollers 31 and 32, the atomic percentage of oxygen at a maximum point on the oxygen distribution curve closest to the back surface of the first gas barrier layer 2a is almost the same as the atomic percentage of oxygen at a maximum point on the oxygen distribution curve closest to the surface of the first gas barrier layer 2a, and thus, it is found that the atomic percentage of oxygen at a maximum point on the oxygen distribution curve closest to the back surface of the first gas barrier layer 2a is not the greatest value.

(Raw Material Gas)

The raw material gas in the deposition gas used for forming the first gas barrier layer 2a can be appropriately selected for the use depending on the material of the gas barrier layer to be formed. For example, organosilicon compounds containing silicon is preferably used as the raw material gas.

Examples of the organosilicon compounds include hexamethyldisiloxane, 1,1,3,3-tetramethyldisiloxane, vinyltrimethylsilane, methyltrimethylsilane, hexamethyldisilane, methylsilane, dimethylsilane, trimethylsilane, diethylsilane, propylsilane, phenylsilane, vinyltriethoxysilane, vinyltrimethoxysilane, tetramethoxysilane, tetraethoxysilane, phenyltrimethoxysilane, methyltriethoxysilane, octamethylcyclotetrasiloxane, and the like.

Among these organosilicon compounds, hexamethyldisiloxane and 1,1,3,3-tetramethyldisiloxane are preferable from the viewpoint of ease of handling during deposition and the gas barrier properties of the resulting first gas barrier layer 2a. In addition, these organosilicon compounds can be used alone or in combination of two or more kinds.

Furthermore, a reactive gas may be simultaneously used as the deposition gas in addition to the raw material gas. The reactive gas can be appropriately selected for use from gases that produce inorganic compounds such as oxides and nitrides by reacting with the raw material gas.

The reactive gas for the production of the oxides which can be used includes, for example, oxygen and ozone. In addition, the reactive gas for the production of the nitrides which can be used includes, for example, nitrogen and ammonia.

The reactive gas can be used alone or in combination of two or more kinds, and in a case of forming, for example, an oxide nitride compound, the reactive gas for the formation of the oxides can be combined with the reactive gas for the formation of the nitrides.

The deposition gas may contain a carrier gas, as necessary, for supplying the raw material gas to the vacuum chamber. Furthermore, the deposition gas may contain a discharge gas, as necessary, for generating the plasma discharge. Any appropriate known gas may be used as the carrier gas and the discharge gas, and examples include a noble gas such as helium, argon, neon, xenon, or the like.

When the deposition gas like this contains the raw material gas and the reactive gas, it is preferable to include the reactive gas at a percentage not much higher than the theoretical percentage of the reactive gas required for complete reaction of the raw material gas and the reactive gas. When the percentage of the reactive gas is too high, the first gas barrier layer 2a cannot be prepared. In order to obtain the gas barrier film having predetermined properties, it is preferable that, for example, when the deposition gas contains the organosilicon gas and oxygen, the percentage of oxygen equal to or less than a theoretical percentage of oxygen required for complete oxidation of all organosilicon compounds in the deposition gas.

Hereinafter, explanation will be made by the use of, as the representative example, hexamethyldisiloxane (organosilicon compound: HMDSO, $(CH_3)_6Si_2O$) as the gas material and oxygen ($O_2$) as the reactive gas.

In a case where a silicon-oxygen thin film is fabricated by reacting the deposition gas containing hexamethyldisiloxane (HMDSO: $(CH_3)_6Si_2O$) as the raw material gas and oxygen ($O_2$) as the reactive gas by the plasma CVD method, silicon dioxide is yielded according to the reaction shown in the following reaction scheme (1):

$$(CH_3)_6Si_2O+12O_2 \rightarrow 6CO_2+9H_2O+2SiO_2 \qquad (1)$$

In the reaction like this, 12 moles of oxygen is required for complete oxidation of 1 mole of hexamethyldisiloxane. Thus, the complete reaction of the deposition gas containing 12 moles or more oxygen for each mole of hexamethyldisiloxane generates a uniform silicon dioxide layer, and thus, the flow ratio of the raw material gas is adjusted to a ratio equal to or less than the theoretical ratio for complete reaction so as to maintain an incomplete reaction. Namely, the amount of oxygen should be less than 12 moles which is the stoichiometric ratio relative to 1 mole of hexamethyldisiloxane.

Note that, in the actual plasma CVD chamber, hexamethyldisiloxane of the raw material gas and oxygen of the reactive gas are supplied from the gas inlets to the deposition region, and thus, even if the molar amount (flow rate) of oxygen of the reactive gas is 12 times molar amount (flow rate) larger than the molar amount (flow rate) of hexamethyldisiloxane of the gas material, the reaction actually cannot be completely accomplished, and the complete reaction is presumed to be accomplished only when oxygen is supplied in a significantly excess amount to the stoichiometric ratio. For example, there is a case that the molar amount (flow rate) of oxygen may be set to at least about 20 times larger than the molar amount (flow rate) of hexamethyldisiloxane of the gas material in order to complete the oxidizing reaction to obtain silicon oxide by the CVD method. Thus, the mole amount (flow rate) of oxygen of the reaction gas relative to the molar amount (flow rate) of hexamethyldisiloxane of the gas material is preferably 12 times or less, which is the stoichiometric ratio, more preferably 10 times or less.

When containing hexamethyldisiloxane and oxygen in such amounts, the carbon atoms and hydrogen atoms in the hexamethyldisiloxane that are not completely oxidized are taken into the first gas barrier layer 2a to form the desired first gas barrier layer 2a, and the resulting gas barrier film has an excellent gas barrier property and bending resistance.

In addition, the lower limit of the molar amount (flow rate) of oxygen relative to the molar amount (flow rate) of hexamethyldisiloxane in the deposition gas is preferably more than 0.1 times of the molar amount (flow rate) of hexamethyldisiloxane, more preferably more than 0.5 times.
(Vacuum Level)

The pressure (vacuum level) in the vacuum chamber can be appropriately adjusted depending on the kind of raw material gas and is preferably within the range of 0.5 to 100 Pa.
(Roller Deposition)

In such a plasma CVD method, in order to perform discharge between the deposition rollers 31 and 32, the electric power to be applied to electrode drums connected to the power source 51 for plasma generation (in the present embodiment, disposed on the deposition rollers 31 and 32) can be appropriately adjusted depending on the kind of the raw material gas and the pressure in the vacuum chamber, for example, the electric power is preferably within the range of 0.1 to 10 kW.

When the electric power applied within the above range would not generate particles, and the heat generated during deposition is controllable, and thus there are no heat damage in the resin base material 1, and wrinkle generation during deposition in the resin base material 1, due to the increase in temperature at the surface of the resin base material 1 during deposition. Furthermore, there is small possibility that the deposition rollers are damaged because of the melting of the resin base material 1 due to heat, and because of discharge of a large current between the naked deposition rollers.

The conveying rate (line speed) of the resin base material 1 can be appropriately adjusted depending on the kind of the raw material gas and the pressure in the vacuum chamber, and the like, and is preferably within the range of 0.25 to 100 m/min, more preferably within the range of 0.5 to 20 m/min. When the line rate is within the above range, wrinkles in the resin base material 1 due to heat are not readily formed, and the thickness of the first gas barrier layer 2a to be formed can be sufficiently controlled.
[Second Gas Barrier Layer]

There is preferably provided the second gas barrier layer 2b, on the first gas barrier layer 2a, formed by provision of the coating film of a polysilazane-containing solution of the coating system and by modification of the coating film through irradiation with vacuum ultraviolet rays (VUV rays) having a wavelength of 200 nm or less. When the second gas barrier layer 2b is provided on the first gas barrier layer 2a deposited by the CVD method, it is possible to cover minute defects remaining on the first gas barrier layer 2a with the polysilazane gas barrier component, and, as the result, it is preferable to enhance the gas barrier property and bending resistance more.

The second gas barrier layer 2b preferably has a thickness within the range of 1 to 500 nm, more preferably within the range of 10 to 300 nm. When the thickness is more than 1 nm, the gas barrier property can be exhibited, and when the thickness is within the range of 500 nm or less, cracks are not readily yielded in the dense silicon oxide film.
(Polysilazane)

In the second gas barrier layer 2b, the polysilazane represented by the following general formula (A) can be used.

[Chemical formula 1]

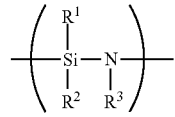

(1) General formula (A)

Wherein $R^1$, $R^2$ and $R^3$ each represent hydrogen atom, an alkyl group, an alkenyl group, a cycloalkyl group, an aryl group, an alkylsilyl group, an alkylamino group, or an alkoxy group.

The polysilazane where $R^1$, $R^2$ and $R^3$ in the above general formula (A) are all hydrogen atoms, i.e. perhydropolysilazane is particularly preferable in view of the density of the resulting second gas barrier layer 2b.

The perhydropolysilazane is presumed to have a linear chain structure and a cyclic structure of mainly 6- and 8-membered rings, and a number average molecular weight (Mn) thereof is about 600 to 2000 (polystyrene equivalent by gel permeation chromatography), and is in the form of liquid or solid.

The polysilazane is commercially available in the form of a solution in an organic solvent, and the commercially available product can be used as it is as the polysilazane-containing coating solution. Examples of the commercially available polysilazane solution include NN120-20, NAX120-20, NL120-20, and the like manufactured by AZ Electronic Materials Co., Ltd.

The second gas barrier layer 2b can be formed by applying the coating solution containing polysilazane to the first gas barrier layer 2a manufactured by the CVD method, drying the applied solution, and then performing irradiation with the vacuum ultraviolet.

It is preferable that an organic solvent used for the preparation of a polysilazane coating solution does not contain a lower alcohol or water, which readily reacts with polysilazane. Examples include hydrocarbon solvents such as an aliphatic hydrocarbon, an alicyclic hydrocarbon, and an aromatic hydrocarbon; halogenated hydrocarbon solvents; and ethers such as an aliphatic ether and an alicyclic ether. Specific examples include hydrocarbons such as pentane, hexane, cyclohexane, toluene, xylene, Solvesso, and turpentine; halogenated hydrocarbons such as methylene chloride and trichloroethane; ethers such as dibutyl ether, dioxane, and tetrahydrofuran, and the like. These organic solvents may be selected in view of the solubility of polysilazane and vapor deposition rate of the solvent, and may also be used in combination of a plurality of the organic solvents.

The concentration of polysilazane in the coating solution containing polysilazane is varied depending on the thickness of the second gas barrier layer 2b and the pot life of the coating solution, and is preferably about 0.2 to 35% by mass.

In order to promote the modification to the silicon oxide nitride, an amine catalyst or a metal catalyst such as a Pt compound such as Pt acetylacetonate, a Pd compound such as propionic acid Pd, or an Rh compound such as Rh acetylacetonate may be added to the coating solution. Especially, the amine catalyst is particularly preferable. Examples of the specific amine catalyst include N,N-diethylethanolamine, N,N-dimethylethanolamine, triethanolamine, triethylamine, 3-morpholinopropylamine, N,N,N',N'-tetramethyl-1,3-diaminopropane, N,N,N',N'-tetramethyl-1,6-diaminohexane, and the like.

The amount to be added to polysilazane is preferably within the range of 0.1 to 10% by mass, more preferably within the range of 0.2 to 5% by mass, furthermore preferably within the range of 0.5 to 2% by mass relative to the total amount of the solution. When the amount to be added of the catalyst is within the above range, it is possible to prevent the formation of excess silanol groups due to a rapid reaction, a decrease in the film density, and an increase in film defects.

The coating solution containing polysilazane can be applied by any appropriate procedure, for example, by roll coating, flow coating, inkjet printing, spray coating, printing, dip coating, casting, bar coating, or gravure printing, and the like.

The thickness of the coating film can be appropriately determined depending on the intended use of the coating film. For example, the thickness of the coating film is preferably within the range of 50 nm to 2 μm, more preferably within the range of 70 nm to 1.5 μm, further preferably within the range of 100 nm to 1 μm.

(Excimer Treatment)

In the process of irradiating the layer containing the polysilazane with the vacuum ultraviolet ray, in the second gas barrier layer 2b, at least a part of the polysilazane is modified to silicon oxide nitride.

Here, the presumed mechanism that the coating film containing the polysilazane during the vacuum ultraviolet ray irradiation is modified into the specific composition $SiO_xN_y$ will be exemplified by perhydropolysilazane.

Perhydropolysilazane can be represented by the composition $[—(SiH_2—NH)_n—]$. When represented by $SiO_xN_y$, $x=0$ and $y=1$. An external oxygen source is necessary to achieve $x>0$, and the oxygen sources include (i) oxygen and water contained in the polysilazane coating solution; (ii) oxygen and water absorbed in the coating film from the atmosphere during application and drying; (iii) oxygen, water, ozone, and singlet oxygen absorbed in the coating film from the atmosphere during the vacuum ultraviolet irradiation; (iv) oxygen and water outgassed from the substrate and migrated into the coating film due to heat and other factors applied during the vacuum ultraviolet irradiation; (v) oxygen and water absorbed by the coating film from an oxidizing atmosphere when the film is moved from a non-oxidizing atmosphere, where vacuum ultraviolet irradiation is performed, to the oxidizing atmosphere.

On the other hand, the upper limit of y is basically 1, because the nitridation of Si atoms is seemed to be very rare compared with the oxidation thereof.

Furthermore, x and y are basically within the range defined by $2x+3y \leq 4$ on the basis of the number of valence electrons in Si, O, and N atoms. When the state of $y=0$ after completing the oxidation, the coating film contains silanol groups, and there is the case where the range is $2<x<2.5$.

The presumed mechanism of the reaction that generates silicon oxide nitride and furthermore silicon oxide from the perhydropolysilazane during the vacuum ultraviolet irradiation step will be explained below.

(1) Dehydrogenation and the Accompanying Formation of Si—N Bond

It is considered that the Si—H bond and the N—H bond in the perhydropolysilazane are relatively easy to be cleaved due to the excitation induced by the vacuum ultraviolet irradiation, and are recombined to the Si—N bond under an inert atmosphere (there is a case that a dangling bond of Si may also be formed). Namely, the film is cured in the composition of $SiN_y$ without oxidation. The cleavage of the Si—H bond and the N—H bond is accelerated by a catalyst and heat. The thus cleaved hydrogen is released in the form of $H_2$ from the film to the exterior.

(2) Formation of Si—O—Si Bond Due to Hydrolysis and Dehydration Condensation

The Si—N bond in the perhydropolysilazane is hydrolyzed to cleave the polymer main chain and to produce a Si—OH. Two Si—OHs are condensed by dehydration into a Si—O—Si bond to be cured. Although such a reaction also occurs in the atmosphere, the main water source during the vacuum ultraviolet irradiation under an inert atmosphere is probably water vapor outgassed from the substrate due to the heat generated during the irradiation. Excess water causes some Si—OHs to remain without dehydration, and thus, a cured film having a composition $SiO_{2.1}$ to $_{2.3}$ has a poor gas barrier property.

(3) Formation of Si—O—Si Bond Involving Direct Oxidation by Singlet Oxygen

An appropriate amount of oxygen in the atmosphere during the vacuum ultraviolet irradiation forms highly oxidative singlet oxygen. The H and N atoms in the perhydropolysilazane are replaced with O atom to form Si—O—Si bond to cure the film. It is presumed that there is a case where the cleavage of the polymer main chain may also cause recombination of the bonds.

(4) Oxidation Accompanying Cleavage of Si—N Bond Due to Vacuum Ultraviolet Irradiation and Excitation It is presumed that since the energy of the vacuum ultraviolet rays is higher than the energy of the Si—N bond in the perhydropolysilazane, the Si—N bond is cleaved, and when there is an oxygen source such as oxygen, ozone or water in the environment, is oxidized to form a Si—O—Si bond or a Si—O—N bond. It is also presumed that there is a case where the recombination of the bonds may be yielded by the cleavage of the polymer main chain.

The composition of silicon oxide nitride of the layer obtained by vacuum ultraviolet irradiation to the layer containing the polysilazane can be adjusted by controlling the oxidized level through an appropriate combination of the oxidation mechanisms (1) to (4).

In the step of the vacuum ultraviolet irradiation process, the illuminance of the vacuum ultraviolet ray on the coating surface of the polysilazane-containing coating film is preferably within the range of 30 to 200 mW/cm$^2$, more preferably within the range of 50 to 160 mW/cm$^2$. When 30 mW/cm$^2$ or more, enough modification efficiency can be maintained, and when 200 mW/cm$^2$ or less, ablation of the coating film is not yielded and damage to the resin base material 1 can be avoided.

The irradiation energy of the vacuum ultraviolet ray on the surface of the polysilazane-containing coating film is preferably within the range of 200 to 10000 mJ/cm$^2$, more preferably within the range of 500 to 5000 mJ/cm$^2$. When the irradiation energy is 200 mJ/cm$^2$ or more, sufficient modification can be performed when the irradiation energy is 10000 mJ/cm$^2$ or less, excessive modification does not result, and thus cracking and thermal deformation of the substrate are not caused.

A noble gas excimer lamp described below is preferably used as the vacuum ultraviolet light source.

It is known that the excimer emission can be obtained by the use of dielectric-barrier discharge. The dielectric-barrier discharge is a significantly narrow micro-discharge, similar to thunder, that is generated in a gas space in response to the application of a high-frequency high-voltage of several tens of kilohertz to electrodes, the gas space being disposed between the electrodes through dielectric substance, such as transparent quartz. When the micro-discharge streamer reaches the tube wall (dielectric material), the electric charges are stored on the surface of the dielectric, and thus, the micro-discharge disappears. The dielectric-barrier discharge is a discharge where the micro-discharges are spread over the entire tube wall, and the cycles of generation and disappearance are repeated. Thus, the flickering of light can be visually confirmed. In addition, since streamers of an extremely high temperature directly reach local points of the tube wall, there is a possibility that degradation of the tube wall is accelerated.

Other than the dielectric-barrier discharge, an electrodeless field discharge is also means for generating the excimer emission efficiently. The electrodeless field discharge occurs as a result of capacitive coupling and is also referred to as RF discharge. The lamp, the electrodes, and their arrangement are basically the same as those for the dielectric-barrier discharge. The high frequency applied to the electrodes illuminates the lamp at several MHz. Such spatially or temporally uniform discharge achieved through electrodeless field discharge provides a lamp having a long life without flickering.

Since, in the dielectric-barrier discharge, the micro-discharge is generated only between the electrodes, in order to discharge over the entire discharge space, it is necessary to cover the entire external surface with an external electrode, and the electrode should transmit the light for taking out the light to the outside.

Thus, a mesh of thin metal wires is used as the electrode. Since an electrode is composed of very thin wires that do not block light, the electrode is easy to be damaged in an oxygen atmosphere by ozone generated by the vacuum ultraviolet rays. This can only be avoided by providing an inert gas atmosphere such as a nitrogen atmosphere, around the lamp inside the irradiation apparatus and radiating the light through a window of synthetic quartz. However, the window of synthetic quartz is not only an expensive consumable but gives a loss of light.

The outer diameter of the double cylinder lamp is about 25 mm, and the difference between the distance from just below the lamp axis to the irradiated surface and the distance from the side of the lamp to the irradiated surface cannot be eliminated from consideration, and a significant difference in illuminance is caused. Therefore, a uniform illuminance distribution cannot be obtained even though the alignment of multiple lamps in close contact with each other. An irradiation apparatus having a window of synthetic quartz can establish a uniform distance and a uniform illuminance distribution in an oxygen atmosphere.

When using the electrodeless field discharge, it is not necessary that the external electrode is made of the mesh electrode. When disposing an external electrode only on a part of the external surface of the lamp, the glow discharge spreads throughout the entire discharge space. The external electrode is typically composed of an aluminum block that also functions as a light reflector and is disposed on the back of the lamp. However, since the outer diameter of the lamp is large similarly to that in the dielectric-barrier discharge, the synthetic quartz is required for a uniform illuminance distribution.

The greatest advantage of a fine tube excimer lamp is a simple structure. A gas used for the excimer emission is sealed inside a quartz tube with closed ends.

The outer diameter of the tube of the fine tube lamp is about 6 to 12 mm, and a large diameter requires a high start-up voltage.

The form of discharge may be either dielectric-barrier discharge or electrodeless field discharge. Each electrode may have a flat contact surface in contact with the lamp. Alternatively, each electrode may have a curved contact surface that conforms with the surface of the lamp. In this way, the electrode firmly secures the lamp and tightly adheres to the lamp to stabilize the discharge. The curved surface may be composed of an aluminum mirror that functions as a light reflector.

A Xe excimer lamp radiates an ultraviolet ray having a single wavelength of a short wavelength of 172 nm, and thus has a high light emission efficiency. Since the light from such a Xe excimer lamp which has a large absorption coefficient to oxygen, radical oxygen species and ozone can be generated in a high concentration from a slight amount of oxygen.

In addition, it is known that that the energy of the light having a short wavelength of 172 nm has high capability of disassociating bonds of an organic substance. The high energy of the active oxygen, ozone, and the ultraviolet rays can achieve modification of the polysilazane layer in a short time.

Therefore, in comparison with the low-pressure mercury lamp and the plasma cleaning device that generate light having wavelengths of 185 nm and 254 nm, a reduction in process time along with high throughput, a reduction in the installation area, and irradiation of an organic material, plastic substrate or the like which is easily damaged by heating are made possible.

Since the excimer lamp can emit lights at a high efficiency, the lamp can be driven with a low electric power. Furthermore, since the excimer lamp radiates an energy having a short wavelength in the ultraviolet region without generating light having a long wavelength which causes elevation of temperature, there is a feature that prevents the elevation of temperature at the surface of the target to be irradiated. Accordingly, the excimer lamp is suitable for use on flexible film material such as PET, which is easy to be affected by heat.

Although oxygen is required for the reaction in the ultraviolet irradiation process, since oxygen absorbs the vacuum ultraviolet rays, the irradiation with vacuum ultraviolet rays should be carried out in an atmosphere with an oxygen concentration as low as possible to maintain the efficiency of ultraviolet irradiation. Therefore, the oxygen concentration at the vacuum ultraviolet irradiation is preferably within the range of 10 to 10000 ppm, more preferably within the range of 50 to 5000 ppm, further preferably within the range of 1000 to 4500 ppm.

The gas filling the irradiation atmosphere at the vacuum ultraviolet irradiation is preferable a dry inert gas, and more preferably a dry nitrogen gas in view of cost advantage. The oxygen concentration can be controlled by measuring the flow rates of the oxygen gas and the inert gas fed into the irradiation chamber and varying the ratio of the flow rates.

[Cap Layer]

The cap layer 12 is a layer formed through a dry process. In addition, the cap layer 12 is preferably made of a silicon (Si) nitride as a principal component. Furthermore, it is preferable that a film made of a silicon (Si) nitride as a principal component is formed by a multi-deposition method.

When the cap layer 12 is made of a silicon (Si) nitride as a principal component formed through a dry process, it is possible to efficiently prevent permeation of gases discharged from the light scattering layer 3 and the smoothing layer 4 described below, water in the atmosphere, and the like. Furthermore, it is possible to prevent a harmful influence such as degradation of preservability or electric short circuit under a high temperature and high humidity atmosphere due to unevenness of the surface of the gas barrier layer 2 or the light scattering layer 3.

Here, the principal component means a component having the highest percentage among the components constituting the cap layer 12.

Moreover, the cap layer 12 preferably has a water vapor permeability of less than 0.1 g/(m²·24 h). The water vapor permeability of the cap layer 12 is a value measured by the method in accordance with JIS-K-7129-1992. The cap layer 12 has a water vapor permeability (25±0.5° C., relative humidity 90±2% RH) of less than 0.1 g/(m²·24 h), preferably 0.01 g/(m²·24 h) or less, and more preferably 0.001 g/(m²·24 h) or less.

The cap layer 12 preferably has a refractive index within the range of 1.7 to 3.0, more preferably within the range of 1.8 to 2.5, and particularly preferably within the range of 1.8 to 2.2. The refractive index is a value measured at a wavelength of 633 nm at 25° C. by the use of an ellipsometer, as a representative value.

When the cap layer 12 is composed of a material having a low refractive index (refractive index of less than 1.7), the thickness thereof is preferably smaller, and is more preferably less than 100 nm. However, the cap layer 12 preferably has a certain gas barrier property, and thus, in that respect, the lower limit of the thickness is a thickness at which a continuous film is formed. From this point of view, the thickness thereof is necessary 5 nm or more, preferably 10 nm or more, and particularly preferably 50 nm or more.

In contrast, when the cap layer 12 is composed of a material having a high refractive index (refractive index of 1.7 or more), the upper limit of the thickness thereof is not limited, and for example, in consideration of the gas barrier property, the thickness thereof is preferably 100 nm or more preferably 200 nm or more. The upper limit of the thickness is preferably 1000 nm or less.

When the thickness is within the above range, it is possible to obtain sufficiently the gas barrier properties required to the cap layer 12 such as an oxygen gas barrier property and a moisture barrier property. However, when the film of the cap layer 12 has a visual light absorption, the thickness is preferably smaller, and the optimum thickness may be selected from the viewpoints of the required gas barrier property and the extraction efficiency.

Furthermore, the cap layer 12 preferably has a refractive index larger than that of the smoothing layer 4 which is an underlayer of the cap layer 12. The emitted light h from the light-emitting unit 6 enters to the cap layer 12, and the light passes through the cap layer 12 passes through the smoothing layer 4 or the like, and then taken out from the resin base material 1 side. In general, the resin base material 1 is composed of a material having a lower refractive index than that of the light-emitting unit 6. Therefore, when the refractive index of the layer at the resin base material 1 side is relatively smaller than the refractive index of the layer near the light-emitting unit 6, since the reflection of the light at each interface can be inhibited, the extraction efficiency can be enhanced.

Specifically, since an organic material having a high refractive index is usually used for the light-emitting unit 6, an average refractive index nc of the cap layer 12 is preferably a value near the refractive index of the organic functional layer included in the light-emitting unit 6. The cap layer 12, at the shortest light-emitting maximum wavelength among the light-emitting maximum wavelengths of the emitted light h from the light-emitting unit 6, preferably has a high refractive index layer having the average refractive index nc of 1.5 or more, particularly preferably within the range of 1.8 or more and 2.5 or less. When the average refractive index nc is 1.8 or more and 2.5 or less, the cap layer may be formed by the use of a single material, or by combining two or more compounds. Furthermore, in this case, if the average refractive index nc of the mixed layers may be within the range of 1.8 or more and 2.5 or less, the refractive index of each material may be 1.8 or less or 2.5 or more.

Here, the "average refractive index nc" means, when formed by a single material, the refractive index of the single material, and when formed by mixed system, the calculation refractive index calculated by summing values obtained by multiplying the mixing ratio in each of the specific refractive index which is inherent to the material, and usually is a value calculated on the basis of volume ratio. Note that the measurement of the refractive index is conducted in an atmosphere of 25° C. by irradiating the shortest light-emitting maximum wavelength among the light-emitting maximum wavelengths of the emitted light h from the light-emitting unit 6, and measuring Abbe refractometer (DR-M2 manufactured by ATAGO Co., Ltd.).

Furthermore, it is preferable that an absorption (a value obtained by dividing the sum of T % R % in the spectroscopic wavelength measurement with an integrating sphere) over the whole visual region of the layer per 100 nm of a unit thickness is small, preferably less than 10%, more preferably less than 5%, furthermore preferably less than 3%, most preferably less than 1%.

Furthermore, it is important that the cap layer 12 has a smooth surface to form the transparent electrode 5 thereon well, and the smoothness is preferably, as an arithmetic mean roughness Ra, within the range of 0 to 50 nm, more preferably 30 nm or less, particularly preferably 10 nm or less, the most preferably 3 nm or less. Furthermore, the cap layer 12 preferably has an arithmetic mean roughness Ra smaller than that of the smoothing layer 4 which is an underlayer of the cap layer 12.

When the arithmetic mean roughness Ra is made to be small, it is possible to inhibit the defects such as short circuit of the organic EL element to be laminated. Particularly, when the cap layer 12 is formed, since the arithmetic mean roughness Ra can be smaller than the smoothing layer 4 to enhance the smoothness of surface where the transparent electrode 5 is formed, it is possible to inhibit the generation of the defects of the organic EL element. Note that, although the arithmetic mean roughness Ra is preferably 0 nm, a practical lower value is, for example, 0.5 nm.

Here, the arithmetic mean roughness Ra of the surface represents an arithmetic mean roughness according to JIS B 0601-2001. Note that the surface roughness (arithmetic mean roughness Ra) is measured by the use of an atomic force microscope (Atomic Force Microscope: AFM) manufactured by Digital Instruments Co., Ltd., and calculated from a sectional curve of unevenness continuously measured with a detection device having a sensing pin with a tiny tip radius. The measurement was conducted three times within a zone of 10 μm in the measuring direction with the sensing pin with a tiny tip radius, and a value was calculated from average roughness relating to amplitude of fine unevenness.
(Deposition Through Dry Process)

Hereinafter, a method for forming a silicon nitride as the cap layer 12 by the use of a dry process will be explained.

The silicon nitride contained in the cap layer 12 is, for example, a reaction product of an inorganic silicon compound or an organosilicon compound.

Examples of the reaction products of the inorganic silicon compound include silicon oxide nitride, silicon nitride, silicon carbide nitride, and the like.

Examples of the organosilicon compounds include hexamethyldisiloxane, 1,1,3,3-tetramethyldisiloxane, vinyltrimethylsilane, methyltrimethylsilane, hexamethyldisilane, methylsilane, dimethylsilane, trimethylsilane, diethylsilane, propylsilane, phenylsilane, vinyltriethoxysilane, vinyltrimethoxysilane, tetramethoxysilane, tetraethoxysilane, phenyltrimethoxysilane, methyltriethoxysilane, octamethylcyclotetrasiloxane, and the like.

Among them, hexamethyldisiloxane and 1,1,3,3-tetramethyldisiloxane are preferable from the viewpoint of handling during deposition and gas barrier properties of the resulting cap layer 12. Furthermore, these organosilicon compounds may be used alone or in combination of two or more kinds.

For example, in a case of depositing the cap layer 12 which contains the reaction product of hexamethyldisiloxane by the use of the plasma CVD method, the mole amount (flow rate) of oxygen of the reaction gas relative to the molar amount (flow rate) of hexamethyldisiloxane of the raw material gas is preferably 12 times or less, which is the chemically stoichiometric ratio (more preferably 10 times or less).

When hexamethyldisiloxane and oxygen are contained in such amounts, the carbon atoms and hydrogen atoms in the hexamethyldisiloxane not having been completely oxidized are taken into the cap layer 12 to thereby make it possible to form the desired cap layer 12, with the result that the obtained first gas barrier film can exhibit an excellent barrier property and bending resistance.

Furthermore, the lower limit of the molar amount (flow rate) of oxygen relative to the molar amount (flow rate) of hexamethyldisiloxane in the deposition gas is preferably more than 0.1 times of the molar amount (flow rate) of hexamethyldisiloxane, more preferably more than 0.5 times.

Moreover, as the deposition apparatus, there is a magnetron spattering apparatus that includes an RF magnetron plasma generating part, and a silicon target for spattering by the yielded plasma, and these parts are connected to a vacuum treating chamber through an introducing part. In the deposition apparatus, the RF magnetron spattering source is constituted by the RF magnetron plasma generating part and the target. The deposition can be achieved by generating a plasma of argon gas in the RF magnetron plasma generating part, applying an RF to a disk-like target to spatter the silicon atom of the target (RF magnetron spattering), and depositing them on the surface of the smoothing layer 4 which is positioned at the downstream.

In the deposition through the dry process, it is a rear case that the formulation is stoichiometric ratio, because of a slight amount of gases other than the injected gases. Specifically, though the representative stoichiometric formulation is $Si_3N_4$, since the practical film has a variation chemical formulation ratio to some extent, the formula is represented by SiN which includes the above case.

The above atomic ratio can be determined by a conventionally known method, and for example, can be measured by an analytical apparatus where X-ray Photoelectron Spectroscopy (XPS) is utilized.

Examples of the dry process include a vapor deposition method (resistance heating, EB method, and the like), a plasma CVD method, a sputtering method, anion plating method, and the like, and, if a dense film having a small moisture permeability and a low film stress can be formed, any method may be employed. In addition, the plasma CVD method used for the formation of the above first gas barrier layer 2a is also applicable.

As mentioned above, the cap layer 12 is formed through the dry process, and a very preferable embodiment id to use a composite film or a laminated film where the same or different materials are multi-deposited. The composite film or the laminated film can endow the cap layer 12 with its function and action as the whole.

Furthermore, since considering the above viewpoints and achievement, in the dry process, particularly preferable is silicon oxide nitride or silicon nitride.

[Layer Formed Between Gas Barrier Layer and Cap Layer]

The light extraction substrate includes a light extraction layer having at least a light scattering layer between the gas barrier layer 2 and the cap layer 12 in order to enhance the light extraction efficiency. With respect to the light extraction substrate shown in FIG. 1, the light scattering layer 3 and the smoothing layer 4 are provided as the light scattering layer formed between the gas barrier layer 2 and the cap layer 12 formed on the light scattering layer 3.

In the light extraction substrate, an in-membrane water content (hereinafter, referred to as simply in-membrane water content) of the layer formed between the gas barrier layer 2 and the cap layer 12 is less than $1.0 \times 10^{15}$/mg. Therefore, in the light extraction substrate shown in FIG. 1, the in-membrane water content of the light scattering layer 3 and the smoothing layer 4 may be less than $1.0 \times 10^{15}$/mg.

In order to make the above in-membrane water content being less than $1.0 \times 10^{15}$/mg, after forming all layers formed between the gas barrier layer 2 and the cap layer 12, the treatment for reducing an in-membrane water content is carried out before forming the cap layer 12. Furthermore, after the treatment for reducing the in-membrane water content, it is necessary to maintain the in-membrane water content at a level of less than $1.0 \times 10^{15}$/mg until the formation of the cap layer 12. The treatment for reducing an in-membrane water content is explained after.

The layer formed between the gas barrier layer 2 and the cap layer 12 is not limited to the light scattering layer 3 and the smoothing layer 4, and may include other layers. For example, any layers made of materials such as an organic material or inorganic material, and may also be a layer which does not directly relate to the light extraction function. Even if any layers are included, the in-membrane water content of all layers formed between the gas barrier layer 2 formed at the resin base material 1 side and the cap layer 12 formed at the electrode of the organic EL element side satisfies the request of less than $1.0 \times 10^{15}$/mg.

[Light Scattering Layer]

In the organic EL element shown in FIG. 1, since the emitted light h enters from the light-emitting unit 6 to the light scattering layer 3 through the smoothing layer 4, it is preferable that the average refractive index ns of the light scattering layer 3 is as close as possible to the refractive index of the smoothing layer 4. The light scattering layer 3, at the shortest light-emitting maximum wavelength among the light-emitting maximum wavelengths of the emitted light h from the light-emitting unit 6, preferably is a high refractive index layer having the average refractive index ns within the range of 1.6 or more and less than 2.5, more preferably within the range of 1.7 or more and less than 2.3, particularly preferably within the range of 1.8 or more and less than 2.1. In this case, the light scattering layer 3 may be formed by the use of a single material having the average refractive index ns of 1.6 or more and less than 2.5, or by combining two or more compounds to make the average refractive index ns of 1.6 or more and less than 2.5. Furthermore, in this case, if the average refractive index ns of the mixed layers may be within the range of 1.6 or more and less than 2.5, the refractive index of each material may be less than 1.6 or 2.5 or more.

Here, the "average refractive index ns" means, when formed by a single material, the refractive index of the single material, and when formed by mixed system, the calculation refractive index calculated by summing values obtained by multiplying the mixing ratio in each of the specific refractive index which is inherent to the material.

In addition, the light scattering layer 3 is preferably a scattering film which is composed of a mixture of a binder having a low refractive index which is a layer medium and the light scattering particles having a high refractive index which is contained in the layer medium, where the refractive index difference therebetween is utilized.

The binder having a low refractive index has a refractive index nb of less than 1.9, particularly preferably less than 1.6.

Here, the refractive index nb of the binder means, when formed by a single material, the refractive index of the single material, and when formed by mixed system, the calculation refractive index calculated by summing values obtained by multiplying the mixing ratio in each of the specific refractive index which is inherent to the material.

In addition, the light scattering particle having a high refractive index has a refractive index np of 1.5 or more, preferably 1.8 or more, particularly preferably 2.0 or more.

Here, the refractive index np of the light scattering particle means, when formed by a single material, the refractive index of the single material, and when formed by mixed system, the calculation refractive index calculated by summing values obtained by multiplying the mixing ratio in each of the specific refractive index which is inherent to the material.

Furthermore, the light scattering particle having a high refractive index of the light scattering layer 3 has a role of function to scatter guided lights, and thus, it is necessary to enhance the light scattering property. In order to enhance the light scattering property, there are considered a configuration in which the refractive index difference between the light scattering particles and the binder is increased, a configuration in which the thickness of the layer is made to be thick, and a configuration in which the density of the particle is large. Among those configurations, one having less trade-off to the other properties is the configuration in which the refractive index difference between the inorganic particles and the binder is increased, because the influence on the other properties is small.

The difference |nb−np| of the refractive indexes between the refractive index nb of the resin base material (binder) as the layer medium and the refractive index np of the light scattering particles contained having a high refractive index contained therein is preferably 0.2 or more, particularly preferably 0.3 or more. When the difference |nb−np| of the refractive indexes between the layer medium and the light scattering particles is 0.03 or more, the scattering occurs on the interface between the layer medium and the light scattering particles. When the difference |nb−np| of the refractive indexes becomes large, since the refraction on the interface becomes large, the scattering effect is preferably enhanced.

Specifically, since the it is preferable that the light scattering layer 3 is a layer having a high refractive index hand has the average refractive index ns within the range of 1.6 or more and less than 2.5, it is preferable, for example, that the refractive index nb of the binder is less than 1.6 and the refractive index np of the light scattering particles having a high refractive index is more than 1.8.

Note that the measurement of the refractive index is conducted, as in the cap layer 12, in an atmosphere of 25° C. by irradiating the shortest light-emitting maximum wavelength among the light-emitting maximum wavelengths of the emitted light h from the light-emitting unit 6, and measuring Abbe refractometer (DR-M2 manufactured by ATAGO Co., Ltd.).

As described above, the light scattering layer 3 can be formed as the layer for diffusing the light due to the difference of the refractive indexes between the layer medium and the light scattering particles. Therefore, it is required for the light scattering particles to be contained to scatter the emitted light h from the light-emitting unit 6 without adversely affecting on other layers.

Here, the scattering means that the haze value (the ratio of the scattering transmittance to total light transmittance) of the single film of the light scattering layer 3 is 30% or more preferably 45% or more, particularly preferably 60% or more. When the haze value is 30% or more, it is possible to enhance the light emission efficiency.

The Haze value is a physical value calculated by receiving (i) the influence of the difference of the refractive index of the composition in the layer, and (ii) the influence of the surface shape. Namely, when measuring the haze value by controlling the surface roughness below a certain level, it is possible to measure the haze value without the influence (ii). Specifically, a haze meter (NDH-5000 manufactured by Nippon Denshoku Industries Co., Ltd., etc.) can be used for the measurement.

For example, it is possible to enhance the scattering property, and inhibit defects such as electric short circuit by adjusting the particle diameter. Specifically, it is preferable to use transparent particles having a particle size larger than the region where the Mie scattering in the visible light region occurs. Therefore, the average particle size is preferably 0.2 μm or more.

On the other hand, as the upper limit of the average particle size, when the particle size is larger, since it is necessary to increase also the thickness of the adjacent cap layer 12 or the smoothing layer 4 which is provided for smoothing the roughness of the light scattering layer 3 containing the light scattering particles, it is disadvantageous from the viewpoints of heavy process steps and absorption of the layer, and therefore, the average particle size is preferably less than 1 μm.

Furthermore, when using a plurality of kinds of particles in the light scattering layer 3, the other particles other than the light scattering particles preferably contains at least one kind of particles having the average particle size within the range of 100 nm to 3 μm, and does not contain the particle having the average particle size of 3 μm or more, and particularly, it is preferable to contain at least one kind of particles having the average particle size within the range of 200 nm to 1 µm, and not contain the particle having the average particle size of 1 µm or more.

Here, the average particle size of the particles can be measured, for example, by the use of the machine which utilizes the dynamic light scattering method such as Nanotrac UPA-EX150 manufactured by Nikkiso Co., Ltd., or by image processing of the electron micrographs.

The light scattering particle is not particularly limited and can be appropriately selected depending on the purpose, and may be an organic fine particle or an inorganic fine particle. Particularly preferable is an inorganic fine particle having a high refractive index.

Examples of the organic fine particle having a high refractive index include polymethyl methacrylate beads, acryl-styrene copolymer beads, melamine beads, polycarbonate beads, styrene beads, cross-linked polystyrene beads, polyvinyl chloride beads and benzoguanamine-melamine formaldehyde beads, and the like.

Examples of the inorganic fine particle having a high refractive index include an inorganic oxide particle composed of at least one oxide of a metal selected from zirconium, titanium, aluminum, indium, zinc, tin, antimony, and the like. Specific examples of the inorganic oxide particle include $ZrO_2$, $TiO_2$, $BaTiO_3$, $Al_2O_3$, $In_2O_3$, ZnO, $SnO_2$, $Sb_2O_3$, ITO, $SiO_2$, $ZrSiO_2$, zeolite, and the like, and among them, preferable is $TiO_2$, $BaTiO_3$, $ZrO_2$, ZnO, $SnO_2$, most preferable is $TiO_2$. In addition, among the $TiO_2$, the rutile type is more preferable than the anatase type among the $TiO_2$, since the weather resistance of the light scattering layer 3 and the adjacent layers is enhanced due to low catalytic activity, and furthermore, since the refractive index is high.

In addition, in order to introduce these particles into the light scattering layer 3 having a high refractive index, it may be selected which one is used, a surface-treated one or a not surface-treated one, from the viewpoint of enhancement of dispersibility and stability when preparing a dispersion described below.

When carrying out the surface treatment, examples of the specific surface treating material include a different kind inorganic oxide such as silicon oxide or zirconium oxide, a metal hydroxide such as aluminum hydroxide, an organic acid such as organosiloxane or stearic acid, and the like. These surface treating materials may be used alone or in combination of two or more kinds. Among them, in view of stability of dispersion, the surface treating material is preferably the different kind inorganic oxide and/or the metal hydroxide, more preferably the metal hydroxide.

When the inorganic oxide particle is surface-treated and coated with the surface treating material, a coating amount is preferably within the range of 0.01 to 99% by mass. The coating amount is represented by a mass proportion of the surface treating material to be used for the surface treatment relative to the mass of the particle. When being within the above range, enough effect of enhancement of dispersibility and stability can be obtained by the surface treatment, and it is possible to enhance the light extraction efficiency by the high refractive index of the light scattering layer 3.

In addition, as the materials having a high refractive index, for example, a quantum dot described in WO 2009/014707 or U.S. Pat. No. 6,608,439 can be used suitably.

The light scattering particles having a high refractive index is preferably so disposed that the light scattering particles are in contact with or near the interface of the cap layer 12 or the smoothing layer 4 adjacent to the light scattering layer 3. Thereby, when the total reflection is generated in the cap layer 12 or the smoothing layer 4, the evanescent light oozed out to the light scattering layer 3 can be scattered by the particle to enhance the light extraction efficiency.

The content of the particle having a high refractive index in the light scattering layer 3 is preferably, as a volume package ratio, within the range of 1.0 to 70%, and more preferably within the range of 5.0 to 50%. Accordingly, it is possible to make the refractive index distribution in the interface between the light scattering layer 3 and the adjacent cap layer 12 or the smoothing layer 4, to increase the amount of light scattering which can enhance the light extraction efficiency.

The light scattering layer 3 can be formed by, for example, when the medium of the layer is a resin base material, dispersing the above light scattering particles are dispersed in a solution containing the resin base material (polymer) as the medium and a solution medium which cannot dissolve the particle, and applying on the resin base material 1 or the gas barrier layer 2.

Since the light scattering particle a is really a polydispersible particle and is difficult to arrange regularly, though there is diffraction effect in a local part, almost of the light changes its direction by scattering to enhance the light extraction efficiency.

(Binder)

The binder of the light scattering layer 3 may be the same resin as of the smoothing layer 4 described below.

Furthermore, as the light scattering layer 3, it is particularly suitable to use a compound which is capable of preparing a metal oxide, a metal nitride or a metal oxide nitride by ultraviolet irradiation under the specified atmosphere. Such a compound that may be easily subjected to modification at a relatively low temperature described in Japanese Patent Laid-Open No. 08-112879 are preferable as the compound.

Specifically, examples include a polysiloxane (including polysilsesquioxane) having a Si—O—Si bond, a polysilazane having a Si—N—Si bond, and a polysiloxazane having the both Si—O—Si bond and Si—N—Si bond, and the like. These can be used by mixing two or more kinds. In addition, it is possible to employ a configuration of laminating the different compounds sequentially or a configuration of laminating the different compounds simultaneously.

It is necessary that the thickness of the light scattering layer 3 is thick to some extent in order to ensure the light pass where scattering is generated, and on the other hand, is thin to some extent in order to save the energy loss by absorption. Specifically, the thickness is preferably within the range of 0.1 to 2 µm, more preferably within the range of 0.2 to 1 µm.

(Polysiloxane)

The polysiloxane used in the light scattering layer 3 can include, as the general structure units, $R_3SiO_{1/2}$, $R_2SiO$, $RSiO_{3/2}$ and $SiO_2$. Here, R is selected independently from the group consisting of hydrogen atom, an alkyl group having 1 to 20 carbon atoms (for example, methyl, ethyl, propyl, or the like), an aryl group (for example, phenyl, or the like), and an unsaturated alkyl group (for example, vinyl, or the like). Examples of the specific polysiloxane group include $PhSiO_{3/2}$, $MeSiO_{3/2}$, $HSiO_{3/2}$, $MePhSiO$, $Ph_2SiO$, $PhViSiO$, $ViSiO_{3/2}$, $MeHSiO$, $MeViSiO$, $Me_2SiO$, $Me_3SiO_{1/2}$, and the like. In addition, mixtures and copolymers of polysiloxane can also be used. Note that Vi represents vinyl group.

(Polysilsesquioxane)

In the light scattering layer 3, it is preferable to use a polysilsesquioxane among the above described polysiloxanes. The polysilsesquioxane is a compound containing a silsesquioxane as the structural unit. The "silsesquioxane" is a compound represented by $RSiO_{3/2}$, and is usually $RSiX_3$ (R is hydrogen atom, an alkyl group, an alkenyl group, an aryl group, aralkyl group (also referred to as aralkyl group), and X is a halogen, an alkoxy group, etc).

There are known, as the typical shape of the molecular arrangement of the polysilsesquioxane, an amorphous structure, a ladder-like structure, a cage-type structure, and a partial cleavage structure thereof (structure in which one silicon atom is removed from the cage-type structure, or the silicon-oxygen bond in the cage-type structure is partially cleaved), and the like.

It is preferable to use a so-called hydrogen silsesquioxane polymer among these polysilsesquioxanes. Examples of the hydrogen silsesquioxane polymer is a hydridosiloxane polymer represented by $HSi(OH)_x(OR)_yO_{z/2}$. Each R is an organic group or a substituted organic group, and when bonded to silicon via the oxygen atom, a hydrolyzable substituent is formed. x=0 to 2, y=0 to 2, z=1 to 3, and x+y+z=3 are established. Examples of R include an alkyl group (for example, methyl group, ethyl group, propyl group, butyl group, etc.), an aryl group (for example, phenyl group), an alkenyl group (for example, allyl group, vinyl group, etc.). These resins may be completely condensed $(HSiO_{3/2})_n$, or only partially hydrolyzed (i.e., including a part of Si—OR), and/or partially condensed (i.e., including a part of Si—OH).

(Polysilazane)

The polysilazane used in the light scattering layer 3 is a polymer having a silicon-nitrogen bond, and an inorganic precursor polymer of $SiO_2$, $Si_3N_4$ and an intermediate solid solution $SiO_xN_y$ (x=0.1 to 1.9, y=0.1 to 1.3) of both the $SiO_2$ and $Si_3N_4$, which are composed of Si—N, Si—H, N—H, or the like.

The preferred polysilazane to be used in the light scattering layer 3 is the polysilazane represented by the general formula (A).

From the viewpoint of denseness of the obtained light scattering layer 3, the perhydropolysilazane (PHPS) which is a compound in which $R_1$, $R^2$ and $R^3$ in the general formula (A) are all hydrogen atoms is particularly preferable.

An ionizing radiation curable resin composition can be used as the binder, and the ionizing radiation curable resin composition can be cured by a usual method for curing the ionizing radiation curable resin composition, that is, by irradiating an electron beam or an ultraviolet ray.

For example, in case of the electron radiation curing, an electron beam emitted from an electron beam accelerator such as cock Krumlov Walton type, Van de Graaff type, resonance transformer type, insulated core transformer type, linear type, Dynamitron type, or high frequency type having an energy within the range of 10 to 1000 keV, preferably within the range of 30 to 300 keV are used, and in case of the ultraviolet ray curing, there may be used an ultraviolet ray emitted from an ultra-high pressure mercury lamp, a high pressure mercury lamp, a low pressure mercury lamp, a carbon arc, a xenon arc, a metal halide lamp, or the like.

(Vacuum Ultraviolet Ray Irradiation Apparatus Having Excimer Lamp)

Example of the vacuum ultraviolet ray irradiation apparatus is a noble gas excimer lamp which emits a vacuum ultraviolet ray having a wavelength within the range of 100 to 230 nm.

The noble gas is also referred to as an inert gas since the atoms of noble gas such as xenon (Xe), krypton (Kr), argon (Ar) and neon (Ne), do not form molecules by chemical bonding. However, the atom of the noble gas energized by electric discharge (excited atom) can bond with other atoms to produce a molecule.

For example, in a case where the noble gas is Xe (xenon), as shown in the following reaction scheme, the excited excimer molecule $Xe_2^*$ performing transition to the ground state emits 172 nm excimer light.

$$e + Xe \rightarrow Xe^*$$

$$Xe^* + 2Xe \rightarrow Xe_2^* + Xe$$

$$Xe_2^* \rightarrow Xe + Xe + h\nu \text{ (172 nm)}$$

The feature of the excimer lamp is a high efficiency due to the radiation of light having a single wavelength and substantially no radiation of light with other wavelengths. The temperature of the target can be maintained at a relatively low level, because undesired lights are not emitted. Furthermore, the lamp can be instantaneously turned on/off since the lamp can be started or restarted in a short time.

A dielectric-barrier discharge lamp is suitable as a light source to emit the excimer light efficiently.

The dielectric-barrier discharge lamp may be generally constituted by disposing at least one electrode at a discharge reservoir made of a dielectric material and an exterior thereof in order to generate the electric discharge between the electrodes via the dielectric material. For example, there is a configuration in which an electric discharge reservoir of double cylinder type which is constituted by a big tube and a fine tube made of quartz glass, and is charged with a noble gas such as xenon gas, and a mesh first electrode is attached on the outside of the discharge reservoir and the other electrode is attached inside of the inner tube. In the dielectric-barrier discharge lamp, a dielectric-barrier discharge is generated in the discharge reservoir by applying a high-frequency voltage between the electrodes, and, at the time when the excimer molecule such as xenon produced by the discharge is disassociated, the excimer light is generated.

Since the excimer lamp emits light at a high efficiency, the lamp can be driven with a low electric power. Furthermore, since the excimer lamp radiates an energy having a single wavelength in the ultraviolet region without generating light having a long wavelength which becomes a factor of increasing temperature, there is a feature that prevents the increase of temperature by the irradiation light itself at the surface of the target to be irradiated.

Note that, in order to introduce the light introduced into the adjacent cap layer 12 or the smoothing layer 4, into the light scattering layer 3, it is preferable that a difference of the refractive indexes between the binder of the light scattering layer 3 and the adjacent cap layer 12 or the smoothing layer 4 is small. Specifically, it is preferable that the difference of the refractive indexes between the binder of the light scattering layer 3 and the adjacent cap layer 12 or the smoothing layer 4 is 0.1 or less. In addition, it is preferable that the binder contained in the adjacent smoothing layer 4 is made of the same material of the binder contained in the light scattering layer 3.

Furthermore, when regulating the thickness of the cap layer 12 and the smoothing layer 4 in addition to the light scattering layer 3, it is possible to inhibit the circuit defects due to the penetration of water and the difference of the edges at the patterning, which results in enhancement of light scattering. Specifically, the thickness of the cap layer 12 and the smoothing layer 4 in addition to the light scattering layer 3 is preferably within the range of 100 nm to 3 μm, particularly preferably within the range of 300 nm to 2 μm.

[Smoothing Layer]

The smoothing layer 4 is provided for preventing from defects such as degradation of preservability and electric short circuit under a high temperature and high humidity atmosphere due to unevenness of the surface of the light scattering layer 3, when providing the light-emitting unit 6 on the light scattering layer 3 as a main object, and is provided between the light scattering layer 3 and the cap layer 12.

It is important that the smoothing layer 4 has a smooth surface to form the transparent electrode 5 thereon well, and the smoothness is preferably, as an arithmetic mean roughness Ra, within the range of 0.5 to 50 nm, more preferably 30 nm or less, particularly preferably 10 nm or less, the most preferably 5 nm or less. When the arithmetic mean roughness Ra is made to be within the range of 0.5 to 50 nm, it is possible to inhibit the defects such as short circuit of the organic EL element to be laminated. Note that, although the arithmetic mean roughness Ra is preferably 0 nm, a practical lower value is 0.5 nm.

To the smoothing layer 4, the light transmitted through the cap layer 12 is entered. Therefore, it is preferable that an average refractive index nf of the smoothing layer 4 is the same as or slightly lower than the refractive index of the cap layer 12. Specifically, when the average refractive index nc of the cap layer 12 is 1.8 or more and 2.5 or less as described above, the average refractive index nf of the smoothing layer 4 is, at the shortest light-emitting maximum wavelength among the light-emitting maximum wavelengths of the emitted light h from the light-emitting unit 6, preferably 1.5 or more, particularly preferably within the range of more than 1.65 and less than 2.5. When the average refractive index nf is more than 1.65 and less than 2.5, the cap layer may be formed by the use of a single material, or by combining two or more compounds. When formed by such a mixed system, as the average refractive index nf of the smoothing layer 4, the calculation refractive index calculated by summing values obtained by multiplying the mixing ratio in each of the specific refractive index which is inherent to the material. Furthermore, in this case, if the average refractive index nf of the mixed layers may be within the range of more than 1.65 and less than 2.5, the refractive index of each material may be 1.65 or less or 2.5 or more. The smoothing layer 4 can be preferably prepared by the use of a known high refractive index coating agent, a high refractive index hard coating agent, and the like.

A well-known resins can be used as the binder in the smoothing layer 4 without limit, and examples include acrylic acid esters, methacrylic acid esters, polyethylene terephthalate (PET), polybutylene terephthalate, polyethylene naphthalate (PEN), polycarbonate (PC), polyarylate, polyvinyl chloride (PVC), polyethylene (PE), polypropylene (PP), polystyrene (PS), nylon (Ny), aromatic polyamide, polyether ether ketone, polysulfone, polyether sulfone, polyimide, polyether imide, silsesquioxane, the polysiloxane, the polysilazane, the polysiloxazane, etc. having an organic and inorganic hybrid structure, perfluoroalkyl group-containing silane compounds (for example, (heptadecafluoro-1,1,2,2-tetradecyl)triethoxysilan), a fluorine-containing copolymer having recurring units of a fluorine-containing monomer and a monomer for introducing a cross-linkable group, and the like. These resins may be used in admixture of two or more. Among them, the (meth) acrylic acid esters-based compounds, the resins having the organic inorganic hybrid structure are preferable.

In addition, it is also possible to use the following hydrophilic resin. Examples of the hydrophilic resin include a water-soluble resin, a water-dispersible resin, a colloidal dispersion resin or a mixture thereof. Examples of the hydrophilic resin are polymer such as an acrylic-based resin, a polyester-based resin, a polyamide-based resin, a polyurethane-based resin and a fluorine-containing resin, and examples include polyvinyl alcohol, gelatin, polyethylene oxide, polyvinyl pyrrolidone, casein, starch, agar, carrageenan, polyacrylic acid, polymethacrylic acid, polyacrylamide, polymethacryl amide, polystyrene sulfonic acid, cellulose, hydroxyl ethyl cellulose, carboxyl methyl cellulose, hydroxyl ethyl cellulose, dextran, dextrin, pullulan or a water-soluble polyvinyl butyral, and among them, polyvinyl alcohol is preferred.

The resin used as the binder may be used alone, or in combination of two or more kinds as necessary.

Additionally, a known resin particle (emulsion), and the like may also be suitably used as the binder.

Furthermore, as the binder, a resin mainly curable by ultraviolet ray or electron beam, namely a mixed resin where a thermoplastic resin and a solvent are blended in an ionizing radiation curable resin, or a thermosetting resin may be suitably used.

Preferable of such a binder resin is a polymer having a saturated hydrocarbon or polyether as a main chain, more preferably a polymer having a saturated hydrocarbon as a main chain.

Furthermore, it is preferable that the above binder is cross-linked. A polymer having a saturated hydrocarbon as a main chain is preferably obtained by polymerization of ethylenically unsaturated monomers. In order to obtain a crosslinked binder, it is preferable to use a monomer having two or more ethylenically unsaturated groups.

Examples of the nanoparticles having a high refractive index which are contained in the binder used in the smoothing layer 4 are as follows.

Examples of the nanoparticles having a high refractive index include an inorganic oxide particle composed of at least one oxide of a metal selected from zirconium, titanium, aluminum, indium, zinc, tin, antimony, and the like. Specific examples of the inorganic oxide particle include $ZrO_2$, $TiO_2$, $BaTiO_3$, $Al_2O_3$, $In_2O_3$, $ZnO$, $SnO_2$, $Sb_2O_3$, ITO, $SiO_2$, $ZrSiO_4$, zeolite, and the like, and among them, preferable is $TiO_2$, $BaTiO_3$, $ZrO_2$, $ZnO$, $SnO_2$, most preferable is $TiO_2$. In addition, the rutile type is more preferable than the anatase type among the $TiO_2$, since the weather resistance of the smoothing layer 4 and the adjacent layers is enhanced due to low catalytic activity, and furthermore, since the refractive index is high.

The nanoparticle preferably has a refractive index within the range of 1.7 to 3.0 and is deposited by admixing in the binder as a medium. When the refractive index of the nanoparticle is 1.7 or more, the objects and effects can be sufficiently accomplished. When the refractive index of the nanoparticle is 3.0 or less, the multi-scattering in the layer can be inhibited, and thus the transparency cannot be lowered.

Note that the nanoparticle is so defined as a fine particle (colloidal particle) having a particle size of nano meter order when dispersed in a dispersing medium. The particles include a particle where each particle is disconnected one by one (primary particle), and a particle where particles are agglomerated (secondary particle), and here, the definition of the nanoparticle includes the secondary particle.

The lower limit of the particle size of the nanoparticle is preferably 5 nm or more in usual, more preferably 10 nm or more, further preferably 15 nm or more. In addition, the upper limit of the particle size of the nanoparticle is preferably 70 nm or less, more preferably 60 nm or less, further preferably 50 nm or less. When the particle size of the nanoparticle is within the range of 5 to 60 nm, it is preferable to obtain a high transparency. The particle size distribution is not limited unless the effects of the present invention becomes worse, the distribution may be wide or narrow, or have plural distributions.

Preparation method of the titanium dioxide sol used in the present invention may be referred to, for example, Japanese Patent Laid-Open No. 63-17221, Japanese Patent Laid-Open No. 07-819, Japanese Patent Laid-Open No. 09-165218, Japanese Patent Laid-Open No. 11-43327, and the like.

In order to damp the surface roughness of the light scattering layer 3, the smoothing layer 4 is better to be thick to an extent, and, on the other hand, in order to save the energy loss due to absorption, it is necessary to be thin.

As the process for forming the smoothing layer 4, the smoothing layer 4 is fabricated by, for example, forming the light scattering layer 3, preparing a preparation solution for the smoothing layer by mixing a dispersing solution where the nano $TiO_2$ particles are dispersed and a resin solution and filtrate by a filter, applying the preparation solution for the smoothing layer to the light scattering layer 3, drying, and radiating an ultraviolet ray.

[Electrode]

The organic EL element includes the light-emitting unit 6 having an organic functional layer which is sandwiched by a pair of electrodes composed of the anode and the cathode described below. Hereinafter, the electrodes will be explained in detail.

[Anode (Transparent Electrode)]

The anode (transparent electrode 5) in the organic EL element is prepared by an electrode material with a high work function (4 eV or more) such as a metal, an alloy, an electrically conductive compound, or a mixture thereof. Examples of the electrode material include a metal such as Au or Ag, an electrically conductive transparent material such as CuI, indium tin oxide (ITO), $SnO_2$ or ZnO. In addition, a material capable of forming an amorphous transparent conductive film such as IDIXO ($In_2O_3$—ZnO) may also be used.

The anode may be formed by a process that includes forming a thin film of any of these electrode materials by vapor deposition, sputtering, or other methods and pattering the thin film into a desired shape by photolithography, or, if high patterning accuracy is not necessary (about 100 μm or more), the electrode material may be vapor-deposited or deposited by sputtering through a mask with the desired shape to form a certain pattern.

Alternatively, in a case where a material capable of being coated such as an electrically conductive organic compound is used, a wet film forming method such as a printing method or a coating method may also be used. In order to taking out the emitted light from the anode, it is desirable that the transmittance is increased more than 10%, and a sheet resistance of the anode is preferably hundreds of Ω/sq. or less. The thickness is selected depending to the materials, usually within the range of 10 to 1000 nm, preferably within the range of 10 to 200 nm.

In the organic EL element, it is preferable to use the transparent electrode 5 shown in FIG. 1 as the anode.

As shown in FIG. 1, the transparent electrode 5 has two-layered where in which an underlayer 5a and a conductive layer 5b deposited thereon are laminated from the resin base material 1 side in this order. Among them, the conductive layer 5b is a layer composed of silver or an alloy containing silver as a principal component, and the underlayer 5a is a layer composed of a compound which, for example, contains nitrogen atom.

(1) Underlayer

The underlayer 5a is a layer provided on the conductive layer 5b at the resin base material 1 side. The material to compose the underlayer 5a is not particularly limited, and may be a material which can inhibit the agglomeration of silver at the time when the conductive layer 5b composed of silver or an alloy containing silver as a principal component is deposited, and, for example a compound which contains nitrogen atom or sulfur atom, and the like.

In a case where the underlayer 5a is composed of a material having a low refractive index (refractive index of less than 1.7), the upper limit of the thickness is required to be less than 50 nm, preferably less than 30 nm, further preferably less than 10 nm, and particularly preferably less than 5 nm. When the thickness is less than 50 nm, the optical loss is minimized. On the other hand, the lower limit of the thickness is required to be 0.05 nm or more, preferably 0.1 nm or more, and particularly preferably 0.3 nm or more. When the thickness is 0.05 nm or more, it is possible to achieve uniform deposition of the underlayer and to uniformly achieve the effect (suppression of aggregation of silver).

In a case where the underlayer 5a is composed of a material having a high refractive index (refractive index of 1.7 or more), the upper limit is not particularly limited, and the lower limit of the thickness is the same as the case of the above material having a low refractive index.

However, it is sufficient that the underlayer 5a is formed having a necessary thickness that gives uniform deposition, simply as its function.

The nitrogen-containing compound constituting the underlayer 5a is not particularly limited as long as the compound contains a nitrogen atom within the molecule, and is preferably a compound having a heterocyclic ring containing a nitrogen atom as the hetero atom. Examples of the heterocyclic rings containing a nitrogen atom as the hetero atom include aziridine, azirine, azetidine, azete, azolidine, azoles, ajinan, pyridine, azepane, azepine, imidazole, pyrazole, oxazole, thiazole, imidazoline, pyrazine, morpholine, thiazine, indole, isoindole, benzimidazole, purine, quinoline, isoquinoline, quinoxaline, cinnoline, pteridine, acridine, carbazole, benzo-C-cinnoline, porphyrins, chlorins, choline, and the like.

Examples of the methods for deposition of the underlayer 5a include: a method using a wet process such as an application method, an inkjet method, a coating method, or a dipping method; a method using a dry process such as a vapor deposition method (resistance heating, EB method, and the like), a sputtering method, a CVD method; and the like. Among them, the vapor deposition method is preferably employed.

(2) Conductive Layer

The conductive layer 5b is a layer composed of silver or an alloy containing silver as a principal component, and is deposited on the underlayer 5a. Here, the principal component means a component which has the highest percentage among the components which compose the conductive layer 5b.

Examples of the alloy which composes the conductive layer 5b and contains silver (Ag) as a principal component are silver magnesium (AgMg), silver copper (AgCu), silver palladium (AgPd), silver palladium copper (AgPdCu), silver indium (AgIn), and the like.

The above conductive layer 5b may be a configuration of laminated layers where the layers of silver or the alloy containing silver as a principal component are laminated dividedly in the form of a plurality of layers, as necessary.

Furthermore, the thickness of the conductive layer 5b is preferably within the range of 2 to 15 nm, more preferably within the range of 3 to 12 nm, particularly preferably within the range of 4 to 9 nm. When the thickness is less than 15 nm, since the absorbing components or the reflective components are small, the transmittance of the conductive layer 5b becomes large. When the thickness is more than 2 nm, it is possible to ensure the conductivity of the layer.

Note that, as to the above transparent electrode 5 composed of the underlayer 5a and the conductive layer 5b deposited thereon, the upper surface of the conductive layer 5b may be covered by a protective layer, or laminated by the other electrically conductive layer. In this case, it is preferable that the protective layer and the electrically conductive layer are optically permeable because the transparent electrode 5 does not lose its optical permeability.

There may be employed, as the method for depositing the conductive layer 5b like this, a wet process such as an applying method, an inkjet method, a coating method or a dipping method, or a dry process such as a vapor deposition method (resistance heating, EB method, and the like), a sputtering method, a CVD method. Among them, the vapor deposition method is preferably employed.

Furthermore, although the conductive layer 5b is characterized in that, by depositing on the underlayer 5a, enough conductivity can be obtained even without a high temperature annealing treatment after the deposition of the conductive layer 5b, as necessary, it may be subjected to the high temperature annealing treatment after the deposition.

As explained above, the transparent electrode 5 has, for example, a configuration in which the conductive layer 5b composed of silver or an alloy containing silver as a principal component is provided on the underlayer 5a which composed of a compound containing nitrogen atom. Therefore, when depositing the conductive layer 5b over the underlayer 5a, the silver atom which composes the conductive layer 5b acts interactively with the nitrogen-containing compound composing the underlayer 5a, and then the diffusing distance on the underlayer 5a is decreased to inhibit the agglomeration of the silver.

Here, in general, in the formation of the conductive layer 5b which is composed of silver as a principal component, by the film-growth in the island-growth type (Volmer-Weber: VW-type), the silver particle is easy to be stood alone, and when the thickness is small, it is difficult to obtain electric conductivity to increase a sheet resistance. Therefore, in order to ensure the conductivity of the electrode, although it is necessary to make the electrode thick to a certain degree, the light transmittance is lowered at the thick layer, which results in failure as the transparent electrode.

However, according to the transparent electrode 5, as mentioned above, since the agglomeration of silver by the underlayer 5a, in the deposition of the conductive layer 5b composed of silver or an alloy containing silver as a principal component, the film is formed by the mono-layer growth type (Frank-van der Merwe: FM type).

Furthermore, here, the transparency of the transparent electrode 5 means that a light transmittance at 550 nm is 50% or more, and the above materials to be used as the underlayer 5a are films having a sufficiently good light transmittance in comparison with the conductive layer 5b composed of silver or the alloy containing silver as a principal component. On the other hand, the conductivity of the transparent electrode 5 is ensured mainly by the conductive layer 5b. Accordingly, when the conductive layer 5b composed of silver or the alloy containing silver as a principal component ensures the conductivity at a smaller thickness, it is possible to achieve both the enhancement of the conductivity and the light transmittance of the transparent electrode 5.

[Cathode]

The cathode (counter electrode 7) is an electrode film which acts as a cathode which supplies electrons to the light-emitting unit 6. As the cathode, there are preferably used the electrode materials with a low work function (4 eV or less) such as a metal (referred to as an electron injecting metal), an alloy, an electrically conductive compound, or a mixture thereof.

Examples of the electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, a rare earth metal, and the like.

Among them, in view of electron injection property and durability against oxidation, preferred examples are a mixture of the electron injecting metal and a secondary metal that has a work function higher than that of the electron injecting metal and is more stable, such as a magnesium/silver mixture, a magnesium/aluminum mixture, a magnesium/indium mixture, an aluminum/aluminum oxide ($Al_2O_3$) mixture, a lithium/aluminum mixture, aluminum, and the like.

The sheet resistance as the cathode is preferably several hundred Ω/square or less, and the thickness thereof is selected usually within the range of 10 nm to 5 μm, preferably in the range of 50 nm to 200 nm. Note that, in order to transmit the emitted light, if any one of the anode or cathode of the organic EL element is transparent or translucent, it is suitable to enhance the emitting brightness.

In addition, when, after fabricating the cathode having a thickness of 1 to 20 nm from the above metal, the electrically conductive transparent materials exemplified in the explanation of the anode is fabricated thereon, a transparent or translucent cathode can be fabricated, and by utilizing the technique, it is possible to fabricate an element where both of the anode and cathode have transparency.

Note that, in a case where the emitted light h is also extracted from the cathode (counter electrode 7) side of the organic EL element, the cathode (counter electrode 7) is composed of a conductive material having a good light transparency selected from the above described conductive materials.

The cathode can be fabricated by forming a thin film of the electrode material by a method such as vapor deposition or sputtering.

[Auxiliary Electrode]

An auxiliary electrode 9 is provided to lower an electric resistance of the transparent electrode 5 and is preferably provided in contact with the conductive layer 5b of the transparent electrode 5.

As a material to form the auxiliary electrode 9, a metal having a low electric resistance such as gold, platinum, silver, copper or aluminum is preferable. Since these metals have a low light transmittance, a pattern is formed so far as an extent that there is no influence to take-out the emitted light h from a light extraction surface. It is preferable that the line width of the auxiliary electrode 9 is 50 μm or less in view of a light extraction aperture ratio, and the thickness of the auxiliary electrode 9 is 1 μm or more in view of electric conductivity.

Examples of a method to form the auxiliary electrode 9 include the vapor deposition method, the sputtering method, the printing method, the inkjet method, an aerosol jet method, and the like.

[Extraction Electrode]

The extraction electrode 8 is an electrode which electrically connects the transparent electrode 5 to an external power source, and the material is not particularly limited, and known materials may be used, and, for example, a metal film such as an MAM electrode of three-layered structure (Mo/Al·Nd alloy/Mo) may be used.

[Light-Emitting Unit]

The light-emitting unit 6 is a light-emitting body (unit) which contains at least the following various organic compounds and is constituted of organic functional layers such as a light-emitting layer, a positive hole transport layer and an electron transport layer as main elements. The light-emitting body is sandwiched by a pair of electrodes composed of the anode and the cathode, and a positive hole (hole) supplied from the anode and an electron supplied from the cathode are recombined to emit a light in the light-emitting body.

The light-emitting unit 6 has an exemplified construction where a positive hole injection layer 6a/a positive hole transport layer 6b/a light-emitting layer 6c/an electron transport layer 6d/an electron injection layer 6e are laminated in this order from the transparent electrode 5 side of the anode. Hereinafter, each of the layers will be explained.

[Light-Emitting Layer]

The light-emitting layer 6c preferably contains a phosphorescence-emitting compound as a light-emitting material.

The light-emitting layer 6c is a layer that emits light by recombination of electrons injected from an electrode or an electron transport layer 6d, and positive holes from the positive hole transport layer 6b, and a portion that emits light may be either the inside of the light-emitting layer 6c or an interface between the light-emitting layer 6c and its adjacent layer.

The configuration of the light-emitting layer 6c is not particularly limited as long as the light-emitting material contained therein satisfies a light emission requirement. Furthermore, there may be a plurality of light-emitting layers having the same emission spectrum or emission maximum wavelength. In the case, it is preferable that non-luminescent auxiliary layers (not shown) are present between the light-emitting layers 6c.

The total thickness of the light-emitting layers 6c is preferably within a range of 1 to 100 nm and, more preferably within a range of 1 to 30 nm from the viewpoint of being capable of obtaining a lower driving voltage. Note that the total thickness of the light-emitting layers 6c is a thickness including the thickness of the intermediate layers, in a case where non-luminescent intermediate layers are present between the light-emitting layers 6c.

In a case of the light-emitting layer having 6c a configuration obtained by lamination of a plurality of layers, it is preferable to adjust the thickness of individual light-emitting layer to be within a range of 1 to 50 nm and it is more preferable to adjust the thickness thereof to be within a range of 1 to 20 nm. When the plurality of laminated light-emitting layers corresponds to the emission color of blue, green and red, respectively, a relationship between the thicknesses of the respective light-emitting layers of blue, green and red is not particularly limited.

Furthermore, a plurality of light-emitting materials may be mixed in the light-emitting layer 6c, or a phosphorescence-emitting material and a fluorescence-emitting material (fluorescence-emitting dopant, fluorescent compound) may be mixed in the same light-emitting layer 6c, for use.

It is preferable that the light-emitting layer 6c contains a host compound (emission host, or the like) and a light-emitting material (light-emitting dopant compound), and emits light through the light-emitting material.

The above light-emitting layer 6c can be formed through vapor deposition of a light-emitting material and a host compound, which are described below, by a well-known thin film forming method such as a vacuum vapor deposition method, a spin coating method, a casting method, an LB method or an inkjet method.

(1) Host Compound

The preferable host compound contained in the light-emitting layer 6c is preferably a compound having, in phosphorescence emission at room temperature (25° C.), a phosphorescence quantum yield of less than 0.1. More preferable phosphorescence quantum yield is less than 0.01. Furthermore, a compound having a volume ratio of 50% or more in the light-emitting layer is preferable, among the compounds contained in the layer.

A well-known host compound may be used alone or in combination of a plurality of kinds, as the host compound. It is possible to adjust transfer of charges and increase an efficiency of the organic EL element, by the use of a plurality of the host compounds. Furthermore, it becomes possible to mix different colors of light to be emitted, by the use of a plurality of light-emitting materials mentioned below, and thus an arbitrary emission color can be obtained.

A well-known low-molecular compound, a high-molecular compound having a repeating unit or a low-molecular compound having a polymerizable group such as vinyl group or epoxy group (vapor deposition polymerizable emission host) may be adopted as the host compound to be used.

The well-known host compound is preferably a compound which prevents a light emission wavelength from becoming longer and has a high Tg (glass transition temperature), while having a positive hole transport ability and an electron transport ability.

The glass transition temperature (Tg) here is a value measured by a method in accordance with JIS K 7121, by the use of DSC (Differential Scanning Colorimetry).

Specific examples of the well-known host compound include compounds described in the following documents; for example, Japanese Patent Laid-Open Nos. 2010-251675, 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837, and the like.

(2) Light-Emitting Material

A phosphorescence-emitting compound (phosphorescent compound, phosphorescence-emitting material) and fluorescence-emitting compound (fluorescent compound, fluorescence-emitting material) can be used as the light-emitting material to be used in the organic electroluminescence element.

(Phosphorescence-Emitting Compound)

The phosphorescence-emitting compound is defined as a compound in which light emission from an excited triplet state is observed, and, specifically, a compound that emits phosphorescence at room temperature (25° C.), and a phosphorescence quantum yield at 25° C. is 0.01 or more, and preferable phosphorescence quantum yield is 0.1 or more.

The above-described phosphorescence quantum yield can be measured by a method described on page 398 of Bunko II of Dai 4 Han Jikken Kagaku Koza 7 (1992, published by Maruzen Co., Ltd.). The phosphorescence quantum yield in a solution can be measured by the use of various solvents, and when the phosphorescence-emitting compound is used, it is sufficient that the above-described phosphorescence quantum yield (0.01 or more) is achieved in any of arbitrary solvents.

There are two kinds of principles regarding light emission of the phosphorescence-emitting compound.

One is an energy transfer type, in which carrier recombination takes place on a host compound which transfers the carriers to thereby generate an excited state of the host compound, and then light emission from the phosphorescence-emitting compound is obtained by the transfer of the energy to the phosphorescence-emitting compound.

The other is a carrier trap type, in which a phosphorescence-emitting compound serves as a carrier trap, carrier recombination takes place on the phosphorescence-emitting compound, and then light emission from the phosphorescence-emitting compound is obtained.

In either case, the excited state energy of the phosphorescence-emitting compound is required to be lower than that of the host compound.

The phosphorescence-emitting compound can be used by suitable selection from among the well-known phosphorescence-emitting compounds used for light-emitting layers of general organic EL elements. The phosphorescence-emitting compound is preferably a complex-based compound containing a metal of the groups 8 to 10 in the element periodic table, and more preferable is an iridium compound, an osmium compound, a platinum compound (a platinum complex compound) or a rare earth complex, and most preferable is an iridium compound.

At least one light-emitting layer 6c may contain two or more types of phosphorescence-emitting materials, and a ratio of concentration of the phosphorescence-emitting compound in the light-emitting layer 6c may vary in the direction of thickness of the light-emitting layer 6c.

An amount of the phosphorescence-emitting compound is preferably 0.1% or more by volume and less than 30% by volume relative to the total volume of the light-emitting layer 6c.

Furthermore, the phosphorescence-emitting compound can be used by suitable selection from among the well-known phosphorescence-emitting compounds used for light-emitting layers of organic EL elements.

Specific examples of the phosphorescence-emitting compound include the compounds described in Japanese Patent Application Laid-Open No. 2010-251675, but are not limited thereto.

(Fluorescence-Emitting Compound)

Examples of the fluorescence-emitting compound include a coumarin-based dye, a pyran-based dye, a cyanine-based dye, a croconium-based dye, a squarylium-based dye, an oxobenzanthracene-based dye, a fluorescein-based dye, a rhodamine-based dye, a pyrylium-based dye, a perylene-based dye, a stilbene-based dye, a polythiophene-based dye, a rare earth complex-based phosphor, or the like.

[Injection Layer: Positive Hole Injection Layer, Electron Injection Layer]

The injection layer is a layer provided between an electrode and the light-emitting layer in order to decrease a driving voltage and to enhance an emission luminance, and is detailed in Part 2, Chapter 2 "Denkyoku Zairyo" (pp. 123-166) of "Yuki EL Soshi To Sono Kogyoka Saizensen (Organic EL Element and Front of Industrialization thereof) (Nov. 30, 1998, published by N. T. S Co., Ltd.)", and examples thereof include a positive hole injection layer 6a and an electron injection layer 6e.

The injection layer can be provided as necessary. The positive hole injection layer 6a may be present between an anode (positive electrode) and the light-emitting layer 6c or the positive transport layer 6b, and the electron injection layer 6e may be present between a cathode (negative electrode) and the light-emitting layer 6c or the electron transport layer 6d.

The positive hole injection layer 6a is also detailed in documents such as Japanese Patent Laid-Open Nos. 09-45479, 09-260062 and 08-288069, and specific examples include: a phthalocyanine layer represented by copper phthalocyanine, an oxide layer represented by vanadium oxide, an amorphous carbon layer, a polymer layer employing a conductive polymer such as polyaniline (emeraldine) or polythiophene, and the like.

The electron injection layer 6e is also detailed in documents such as Japanese Patent Laid-Open Nos. 06-325871, 09-17574 and 10-74586 and specific examples include: a metal layer represented by strontium or aluminum, an alkali metal halide layer represented by potassium fluoride, an alkali earth metal compound layer represented by magnesium fluoride, an oxide layer represented by molybdenum oxide, and the like. It is desirable that the electron injection layer 6e is a very thin film, and the thickness thereof is within a range of 1 nm to 10 μm although the thickness depends on the material thereof.

[Positive Hole Transport Layer]

The positive hole transport layer 6b is made of a positive hole transport material having a function of transporting positive holes, and the positive hole injection layer 6a and an electron-blocking layer are also included in the positive hole transport layer 6b, in a broad sense.

The positive hole transport layer 6b can be provided as a sole layer or as a plurality of layers.

The positive hole transport material is a material having a capability to inject or transport positive holes or an electron barrier property and may be either organic or inorganic. Examples thereof include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high molecular oligomer, particularly a thiophene oligomer, and the like.

Those described above can be used as the positive hole transport material. However, it is preferable to use a porphyrin compound, an aromatic tertiary amine compound and a styrylamine compound, particularly an aromatic tertiary amine compound.

Typical examples of the aromatic tertiary amine compounds and the styrylamine compounds include N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-metylphenyl)

phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenylether; 4,4'-bis(diphenylamino)quadriphenyl; N,N,N-tri(p-tolyl)amine; 4-(di-p-tolylamino)-4'-[4-(di-p-tolylamino)styryl]stilbene; 4-N, N-diphenylamino-(2-diphenylvinyl)benzene; 3-methoxy-4'-N,N-diphenylaminostilbene; N-phenylcarbazole; those having two condensed aromatic rings in a molecule described in U.S. Pat. No. 5,061,569, for instance, 4,4'-bis[N-(1-naphthyl)-N-phenylamino]biphenyl (NPD), and 4,4',4"-tris[N-(3-methylphenyl)-N-phenylamino]triphenylamine (MTDATA) in which three triphenylamine units are bonded in a star burst form described in Japanese Patent Laid-Open No. 04-308688.

Furthermore, polymer materials in which these materials are introduced into a polymer chain or serves as a main chain of a polymer can also be used. In addition, inorganic compounds such as a p type-Si and a p type-SiC can also be used as the positive hole injection material and the positive hole transport material.

Furthermore, it is also possible to use so-called p type positive hole transport materials as described in Japanese Patent Laid-Open No. 11-251067 and Applied Physics Letters 80 (2002), p. 139 by J. Huang et. al. It is preferable to use these materials in view of obtaining a light-emitting element having higher efficiency.

Moreover, it is also possible to enhance the p property by doping the material of the positive hole transport layer $6b$ with impurities. Examples thereof include those described in Japanese Patent Laid-Open Nos. 04-297076, 2000-196140, 2001-102175 and J. Appl. Phys., 95, 5773 (2004), and the like.

When a p property of the positive hole transport layer $6b$ is enhanced, it is preferable because an element consuming lower electric power can be fabricated.

This positive hole transport layer $6b$ may have a single layer structure constituted of one or two or more of the above described materials.

The thickness of the positive hole transport layer $6b$ is not particularly limited, but the thickness is generally within a range about from 5 nm to 5 μm, preferably within a range from 5 to 200 nm.

The positive hole transport layer $6b$ can be formed by making the above described positive hole transport material a thin film by a well-known method such as the vacuum vapor deposition method, the spin coating method, the casting method, the printing method including the inkjet method or the LB method.

[Electron Transport Layer]

The electron transport layer $6d$ is made of a material having a function of transporting electrons, and the electron injection layer $6e$ and a positive hole-blocking layer (not shown) are also included in the electron transport layer $6d$, in a broad sense.

The electron transport layer $6d$ can be provided as a single layer structure or a laminated layer structure of a plurality of layers.

In the electron transport layer $6d$ having a single layer structure and the electron transport layer $6d$ having a laminated layer structure, the electron transport material (also doubling as the positive hole-blocking layer) constituting a portion of a layer adjacent to the light-emitting layer $6c$ may have a function of transferring electrons injected from the cathode to the light-emitting layer $6c$. An arbitrary compound can be selected for use from among previously well-known compounds, as such a material.

Examples include a nitro-substituted fluorene derivative, a diphenylquinone derivative, a thiopyrandioxide derivative, carbodiimide, a fluorenylidenemethane derivative, anthraquinonedimethane, an anthrone derivative, and an oxadiazole derivative, and the like. Furthermore, in the above described oxadiazole derivative, a thiadiazole derivative formed by substituting the oxygen atom of the above oxadiazole ring by a sulfur atom, and a quinoxaline derivative having a quinoxaline ring which is well-known as an electron withdrawing group can be used as the material of the electron transport layer $6d$. Moreover, polymer materials in which these materials are introduced into a polymer chain or serves as a main chain of a polymer can also be used.

Furthermore, there can also be used, as a material of the electron transport layer $6d$, metal complexes of an 8-quinolinol derivative such as: tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis (8-quinolinol) zinc (Znq), and metal complexes in which the central metal of the these metal complexes is substituted by In, Mg, Cu, Ca, Sn, Ga or Pb.

In addition to that, a metal-free or metalphthalocyanine and compounds in which the terminals thereof are substituted by an alkyl group, a sulfonic acid group or the like can be preferably used as the material of the electron transport layer $6d$. Additionally, the distyrylpyrazine derivative to be used as the material of the light-emitting layer $6c$ can also be used as the material of the electron transport layer $6d$. In a similar way to the positive hole injection layer $6a$ and the positive hole transfer layer $6b$, inorganic semiconductors such as an n type-Si and an n type-SiC can also be used as the material of the electron transport layer $6d$.

Furthermore, it is possible to enhance the n property by doping the material of the electron transport layer $6d$ with impurities. Examples thereof include those described in documents such as Japanese Patent Laid-Open Nos. 04-297076, 10-270172, 2000-196140 and 2001-102175 and J. Appl. Phys., 95, 5773 (2004). Moreover, it is preferable to introduce potassium or a potassium compound into the electron transport layer $6d$. Examples of the potassium compound to be used include, for instance, potassium fluoride, and the like. In such a way, when the n property of the electron transport layer $6d$ is enhanced, an element consuming lower electric power can be fabricated.

Furthermore, a similar material to the material constituting the above-described underlayer $5a$ may be used as the material of the electron transport layer $6d$ (electron transport compound). This also applies to the electron transport layer $6d$ doubling as the electron injection layer $6e$, and a similar material to the material constituting the above-described underlayer $5a$ may be used.

The thickness of the electron transport layer $6d$ is not particularly limited, but the thickness is generally within a range about from 5 nm to 5 μm, preferably within a range from 5 to 200 nm.

The electron transport layer $6d$ may have a single layer structure constituted of one or two or more kinds of the above described materials.

The electron transport layer $6d$ can be formed by making the above-described material a thin film by the use of a well-known method such as the vacuum vapor deposition method, the spin coating method, the casting method, the printing method including the inkjet method or the LB method.

[Blocking Layer: Positive Hole-Blocking Layer, Electron-Blocking Layer]

The blocking layer is provided as necessary in addition to a basic constituent layer of a thin organic compound film as described above. Examples thereof include a positive hole-blocking layer described in documents such as Japanese Patent Laid-Open Nos. 11-204258 and 11-204359, and p. 237 of "Yuki EL Soshi To Sono Kogyoka Saizensen (Organic EL Element and Front of Industrialization thereof) (Nov. 30, 1998, published by N. T. S Co., Ltd.)", and the like.

The positive hole-blocking layer has a function of the electron transport layer 6d, in a broad sense. The positive hole-blocking layer is made of a positive hole-blocking material having remarkably a small capability to transport positive holes while having a function of transporting electrons, and can enhance a recombination probability of electrons and positive holes by blocking positive holes while transporting electrons. In addition, the configuration of an electron transport layer 6d can be used for the positive hole-blocking layer, as necessary. Preferably, the positive hole-blocking layer is provided adjacent to the light-emitting layer 6c.

On the other hand, the electron-blocking layer has a function of the positive hole transport layer 6b, in a broad sense. The electron-blocking layer is made of a material having remarkably a small capability to transport electrons while having a function of transporting positive holes, and can enhance a recombination probability of electrons and positive holes by blocking electrons while transporting positive holes. Furthermore, the configuration of a positive hole transport layer 6b can be used for the electron-blocking layer, as necessary. The thickness of the positive hole-blocking layer is preferably 3 to 100 nm, more preferably 5 to 30 nm.

[Sealing Member]

A sealing member 10 is a material for covering the organic EL element, and may be a plate-like (film-like) sealing member which is fixed to the resin base material 1 side by an adhesive 11, or may be a sealing film. The sealing member 10 is provided in a state where the terminal portions of transparent electrode 5 and the counter electrode 7 of the organic EL element are exposed and at least the light-emitting unit 6 is covered. Alternatively, the sealing member 10 may be configured so that an electrode is provided on the sealing member, and the electrode is electrically conducted with the terminal portions of transparent electrode 5 and the counter electrode 7 of the organic EL element.

Specific examples of the plate-like (film-like) sealing members 10 include, for example, a glass substrate, a polymer substrate, a metal substrate, and the like, and the materials may be used in the form of a thin film. Examples of glass substrate include particularly soda lime glass, barium strontium-containing glass, lead glass, alminosilicate glass, borosilicate glass, barium borosilicate glass, quartz, and the like. In addition, examples of the polymer substrate include polycarbonate, acryl, polyethylene terephthalate, polyethersulfide, polysulfone, and the like. Examples of the metal substrate include one or more of kinds selected from the group consisting of stainless steel, iron, copper, aluminum, magnesium, nickel, zinc, chromium, titanium, molybdenum, silicon, germanium and tantalum or an alloy thereof.

Among them, from the viewpoint of making the element thinner, a thin-film polymer substrate or a thin-film metal substrate is preferably used as the sealing member 10.

Furthermore, the film-like polymer substrate preferably has an oxygen permeability measured by the method in accordance with JIS K 7126-1987 of $1 \times 10^{-3}$ ml/(m$^2 \cdot$24 hr$\cdot$atm) or less and a water vapor permeability (25±0.5° C., relative humidity (90±2) % RH) measured by the method in accordance with JIS K 7129-1992 of $1 \times 10^{-3}$ g/(m$^2 \cdot$24 h) or less.

In addition, the above substrate material may be processed in the form of recess plate to use as the sealing member 10. In such a case, the substrate member is subjected to processing such as sandblast processing or chemical etching processing to form recess portions.

Furthermore, the adhesive 11 to fix the plate-like sealing member 10 to the resin base material 1 side is used as a sealant to seal the organic EL element which is held between the sealing member 10 and the resin base material 1. Examples of the adhesive 11 include a photo curable and thermosetting type adhesive such as an acrylic acid-based oligomer, methacrylic acid-based oligomer having a reactive vinyl group, a moisture curable type adhesive such as 2-cyanoacrylic acid ester, and the like.

Moreover, examples of the adhesive 11 include a thermosetting or chemical curable (two liquids mixing type) adhesive such as epoxy-based adhesive. In addition, there may be used a hot-melt type adhesive such as polyamide, polyester, polyolefin, and the like. Furthermore, there may be used an ultraviolet curable-type epoxy resin adhesive of cationic curable-type.

Note that there is a case that the organic materials constituting the organic EL element degrade through heat treatment. From such a point of view, it is preferable to use an adhesive 11 which is adherable and curable at a temperature of from room temperature (25° C.) to 80° C. In addition, a drying agent may be dispersed in the adhesive 11.

Application of the adhesive 11 to the adhesion portion of the sealing member 10 and the resin base material 1 may be carried out by the use of a commercially available dispenser, or by printing such as screen-printing.

In addition, when a gap is formed among the plate-like sealing member 10 and the resin base material 1 and the adhesive 11, in case of gaseous phase and liquid phase, it is preferable to inject an inert gas such as nitrogen or argon, or an inert liquid such as a fluorinated hydrocarbon or a silicone oil to the gap. It is possible to make vacuum. Furthermore, it is possible to pack a hydroscopic compound into the gap.

Examples of the hydroscopic compound include, for instance, a metal oxide (for example, sodium oxide, potassium oxide, calcium oxide, barium oxide, magnesium oxide, aluminum oxide, etc.), a sulfate (for example, sodium sulfate, calcium sulfate, magnesium sulfate, cobalt sulfate, etc.), a metal halide (for example, calcium chloride, magnesium chloride, cesium fluoride, tantalum fluoride, cerium brominate, magnesium brominate, barium iodide, magnesium iodide, etc.), a perchloric acid (for example, barium perchloric acid salt, magnesium perchloric acid salt, etc.), and the like. In the sulfate, metal halide and the perchloric acid, an anhydrous salt is suitably used.

On the other hand, when using the sealing film as the sealing member 10, the sealing film is formed on the resin base material 1 in such a manner that the light-emitting unit 6 of the organic EL element is completely covered whereas the terminal portions of the transparent electrode 5 and the counter electrode 7 of the organic EL element are exposed.

The sealing film is constituted by the use of an inorganic material or an organic material. Particularly, it should be constituted by a material having function to protect from immersion of a substance which degrades the light-emitting unit 6 in the organic EL element such as moisture and oxygen. Examples of such a material include, for instance, an inorganic material such as silicon oxide, silicon dioxide or silicon nitride. Furthermore, in order to enhance its fragility of the sealing film, in addition to the film made of the inorganic material, a laminated structure may be formed by the use of a film made of an organic material.

The method for forming the films is not particularly limited, and there may be employed, for example, a vacuum vapor deposition method, a sputtering method, a reactive sputtering method, a molecular beam epitaxy method, a cluster ion beam method, an ion plating method, a plasma polymerization method, an atmospheric plasma polymerization method, a plasma CVD method, a laser CVD method, a heat CVD method, a coating method, and the like.

[Protective Layer, Protective Plate]

Note that, although not showing, a protective layer or a protective plate may be provided between the resin base material 1 so as to sandwich the organic EL element and the sealing member 10. The protective layer or the protective plate is to protect the organic EL element mechanically, and particularly when the sealing member 10 is the sealing film, because the mechanical protection of the organic EL element is not sufficient, it is preferable to provide the protective layer or the protective plate.

Examples of the protective layer or the protective plate to be used include a glass plate, a polymer plate, a thinner polymer film, a metal plate, a thinner metal plate, or a membrane of polymer material, a membrane of metal material. Among them, from the viewpoint of light weight and small thickness, the polymer film is preferably used.

[Effects of Organic EL Element]

The organic EL element of the above embodiment is formed by the use of the light extraction substrate on which the in-membrane water content of the layer formed between the gas barrier layer and the cap layer is less than $1.0 \times 10^{15}$/mg as the substrate. By satisfying the above in-membrane water content, since the water contained in the light extraction substrate is previously lowered, it is possible to inhibit the penetration of water from the layers such as the light scattering layer and the smoothing layer which are formed between the gas barrier layers and the cap layer. Furthermore, by the cap layer, it is possible to prevent the water penetration to the light-emitting unit from the layers such as the light scattering layer and the smoothing layer which are formed between the gas barrier layers and the cap layer.

Therefore, it is possible to enhance the reliability and preservability of the organic EL element.

Furthermore, in the light extraction layer including the light scattering layer, since impurities which give adverse influence on the light-emitting unit are yielded little, there is less influence on the preservability of the organic EL element. Accordingly, since there is no adverse influence on the light-emitting unit by the light extraction layer, it is possible to achieve both the enhancement of light extraction efficiency by the light scattering configuration and the enhancement of the preservability of the organic EL element.

[Use of Organic EL Element]

The organic EL elements having the above described various constructions are surface emitting elements, and thus are usable for light-emitting sources of various types. Examples include a lighting device such as a home lighting device or a car lighting device, a backlight for a timepiece or a liquid crystal, a signboard for advertisement, a light source for a signal, a light source for an optical storage medium, a light source for an electrophotographic copier, a light source for an optical communication processor, a light source for an optical sensor, and the like, but are not limited thereto, and particularly, it can be effectively used as a backlight for a liquid crystal display device which is combined with a color filter and as a light source for a lighting device.

Furthermore, the organic EL element may be used as a kind of lamp such as a lighting device or a light source for exposure, or may be used as a projection device of an image projecting type, or a display device (display) of a type that a still image or moving image is directly seen. In this case, a light-emitting surface area may be enlarged by so-called tiling where light-emitting panels with the organic EL element are combined flatly in response to the recent increasing in size of lighting devices and displays.

When using as a display for reproducing a moving image, a driving system is either a simple matrix (passive matrix) system or active matrix system. Furthermore, when using two or more kinds of the organic EL element according to the present invention having a different color emission, it is possible to produce a color or full color display device.

Hereinafter, a lighting device will be explained as one example of the uses, and next, a lighting device having an emission area enlarged by tiling will be explained.

[Lighting Device]

The organic EL element can be used as a lighting device.

The lighting device having the organic EL element may be designed to endow each organic EL element of the above described configuration with a resonator structure. The objects to be used of the organic EL element having the resonator structure include a light source for an optical storage medium, a light source for an electrophotographic copier, a light source for an optical communication processor, a light source for an optical sensor, and the like, but is not limited thereto. Alternately, the organic electroluminescence element may be used in the above-described use by achieving laser oscillation.

Note that the material used for the organic EL element can be applied to an organic EL element which emits substantial white light (also referred to as white light organic EL element). For example, a plurality of emission colors is emitted at the same time from a plurality of light-emitting materials to prepare a white color emission by color mixing. Examples of the combination of a plurality of emission colors may include a combination containing three maximum emission wavelengths of three primary colors of red, green and blue, or a combination containing two maximum emission wavelengths which are in complementary color relation such as blue and yellow, bluish green and orange, or the like.

In addition, combinations of light-emitting materials to obtain a plurality of emission colors may be a combination of light-emitting materials which emit a plurality of phosphorescence or fluorescence, or a combination of a light-emitting material which emit a plurality of phosphorescence or fluorescence and a material of dye which emits an excitation light from a light-emitting material, and in the white color organic EL element, a plurality of luminous dopants may be combined.

The white color organic EL element can emit a white color light from the organic EL element itself, which is different from a construction where a white color emission is obtained by arranging organic EL elements each of which emits an individual color light in parallel array. Therefore, it is not necessary to use a mask to prepare almost of all layers constituting the element. Thus, for example, the deposition can be carried out over one surface by a vapor deposition method, a casting method, a spin coating method, an inkjet method, a printing method, and the like, which enhances productivity.

Furthermore, the materials to be used for the light-emitting layers of the white color organic EL element are not particularly limited, and, for example, for a backlight in a liquid crystal display element, materials selected from the above metal complexes or well-known light-emitting materials are combined so as to satisfy a wavelength range corresponding to a CF (color filter) property to prepare a white color light.

When using the white color organic EL element explained above, it is possible to produce a lighting device which emits a substantial white light.

<2. Method for Manufacturing Light Extraction Substrate and Organic Electroluminescence Element>

Next, the method for manufacturing the light extraction substrate, and the method for manufacturing the organic electroluminescence element (organic EL element) will be explained. Here, as one example, the processes for producing the light extraction substrate shown in FIG. 1 and the organic EL element where the light extraction substrate is used are explained. Since the embodiments as to the configurations of the light extraction substrate and the organic EL element, and the methods for forming each constituent and conditions are the same as the above embodiment, the detailed explanation is omitted in the following manufacturing method.

[Step of Forming Gas Barrier Layer]

At first, the first gas barrier layer 2a which contains silicon, oxygen and carbon as the structural elements is formed on the resin base material 1 which is selected from the above described resin films and the like through the plasma enhanced chemical vapor deposition method by the use of the plasma CVD apparatus shown in FIG. 3. The deposition conditions of the first gas barrier layer 2a by the use of the plasma CVD apparatus are according to the above described embodiment.

Furthermore, a coating solution which contains the polysilazane represented by the above general formula (A) is applied on the first gas barrier layer 2a. Then, the coating film containing the polysilazane is irradiated with a vacuum ultraviolet ray having a wavelength of 200 nm or less (VUV light) to thereby be modified, and a second gas barrier layer 2b is formed.

[Step of Forming Light Scattering Layer-Smoothing Layer]

Next, on the gas barrier layer 2, the light scattering layer 3 and the smoothing layer 4 are formed as the layer formed between the gas barrier layer 2 and the cap layer 12.

At first, a resin base material solution where the light scattering particle having an average particle size of 0.2 μm or more is dispersed in the binder is applied on the gas barrier layer 2. Furthermore, the modification treatment is conducted by radiation of an ultraviolet ray to form the light scattering layer 3.

Next, after preparing a solution for fabrication of the smoothing layer by mixing a dispersion solution where a nano $TiO_2$ particle is dispersed and a resin solution, and filtrating with a filter, the smoothing layer 4 is formed on the light scattering layer 3 by applying the solution for fabrication of the smoothing layer to the light scattering layer 3, drying, and then radiating an ultraviolet ray.

[Step of Reducing in-Membrane Water Content]

Next, before forming the cap layer 12, the layer formed between the gas barrier layer 2 and the cap layer 12 is subjected to the treatment for reducing in-membrane water content. The treatment for reducing in-membrane water content is conducted under the conditions and method where the in-membrane water content can be reduced more in comparison with the usual drying condition for forming the light scattering layer 3 and the smoothing layer 4 through the wet process.

The treatment for reducing in-membrane water content is carried out, for example, by a vacuum drying, a drying treatment in non-oxygen atmosphere with an inert oven, or the like. Particularly, it is preferable to dry by a vacuum drying which can reduce the in-membrane water content to a lower value.

Preferable vacuum drying is, for example, a vacuum infrared ray (IR) drying or a vacuum heat drying. In the drying in vacuum, it is necessary to give an energy by direct contact heat transferring or by a microwave (light). When the direct contact heat transferring, it is preferable to contact a heating member to the backside surface of the light extraction substrate (surface where the scattering layer is not applied). The heating temperature in the contact heating is preferably high, but the temperature is restricted according to the heat resistance of the substrate, and a long period of time is required for the heating at a low temperature.

Specifically, in order to make the in-membrane water content of the layer formed between the gas barrier layer 2 and the cap layer 12 being less than $1.0 \times 10^{15}$/mg, it is necessary to heat at 80° C. for 40 minutes or more, at 100° C. for 20 minutes or more, or at 120° C. for 10 minutes or more.

In addition, it is preferable that the degree of vacuum is lower, and preferably less than $1.0 \times 10^{-3}$ Pa, more preferably less than $1.0 \times 10^{-4}$ Pa, particularly preferably less than $1.0 \times 10^{-5}$ Pa.

Particularly, considering the productivity of the organic EL element, it is preferable to use the vacuum infrared ray drying by the use of a wavelength controllable IR, where a wavelength which does not give a damage to the configuration of the low heat resistive resin base material 1, and the like. As the wavelength controllable IR, there is employed an IR unit where a filter which cut a longer wavelength region is combined with a halogen heater, and an infrared ray which has a ratio of a spectral radiance at a wavelength of 5.8 μm to a spectral radiance at a wavelength of 3.0 μm of 5% or less is radiated. When radiating the light like this under vacuum or an inert atmosphere, the desired in-membrane water content can be achieved for a short period of time.

Figure 7:
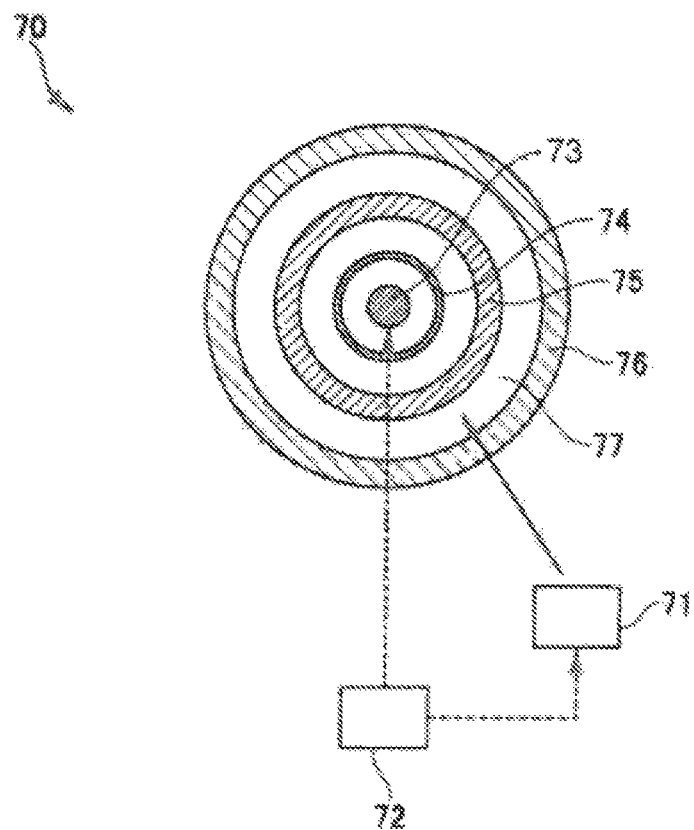
FIG. 7 is a schematic view showing the configuration of the infrared ray heater.

FIG. 7 shows a schematic configuration of an infrared ray heater which is used for the infrared drying by the wavelength controllable IR.

As shown in FIG. 7, the infrared ray heater 70 has a cylindrical appearance, and has a configuration in which a filament 73, a protective tube 74 and filters 75 and 76 are provided in this order in the concentric arrangement. Between the filters 75 and 76, a hollow portion 77 is provided for passing (circulating) a cooling medium.

Furthermore, as shown in FIG. 7, a cooling mechanism 71 which supplies the cooling medium to the hollow part 77 is connected to the infrared ray heater 70. Furthermore, a controlling device 72 is connected to the cooling mechanism 71 and the filament 73. The controlling device 72 controls a flow rate of the cooling medium from the cooling mechanism 71 to the hollow part 77, and an exothermic temperature of the filament 73, and the like.

The filters 75, 76 of the infrared ray heater 70 have a function that can absorb an infrared ray having a wavelength of 3.5 μm or more. In detail, the filters 75 and 76 are heated by the filament 73 for absorbing the infrared ray having a wavelength of 3.5 μm or more. Therefore, when the temperature of the filters 75 and 76 becomes high, the filters 75 and 76 themselves become bodies which radiate infrared rays, and the filters 75 and 76 themselves radiate an infrared ray having a longer wavelength than the infrared ray which is radiated from the filament 73 (secondary radiation).

However, in the infrared ray heater 70, since the cooling medium (for example, cooling air) passes through the hollow part 77 between the filters 75 and 76, due to the cooling function, the surface temperature of the filters 75 and 76 can be lowered. Therefore, the secondary radiation from the filters 75, 76 can be inhibited. As a result, in the infrared ray heater 70, it is possible to lower an infrared ray radiation of the wavelength of 3.5 μm or more, and to lower remarkably a far infrared ray radiation of the wavelength of 5.8 μm or more which is a main absorption range of the resin base material. Then, when the dried material is selectively irradiated with the infrared ray having a wavelength of 3.0 μm which is an absorption range of the solvent, the in-membrane water content of a layer formed between the gas barrier layer and the cap layer, such as the light scattering layer and the smoothing layer can be made to be at a level of less than $1.0 \times 10^{15}$/mg without deformation of the resin base material.

A material of the filters 75 and 76 is a quartz glass, borosilicate crown glass, and the like. From the viewpoint of heat resistance and impact resistance, the filters 75 and 76 are preferably composed of the quartz glass.

Note that, in the infrared ray heater, the thickness and number of filters are optionally selected and changed depending to the necessary infrared ray spectrum. In the cooling function of the infrared ray heater, it is preferable that the filters are laminated in the manner of double or multi-play to provide the hollow part between the filters, and then an air flows through the hollow part. Note that, when the filters are disposed as three or more layers to provide two or more hollow parts, it is preferable to flow the cooling air through each of the hollow parts between the filters in reverse manner from the viewpoint of good cooling efficiency. Furthermore, the cooling air may be discharged to the outside of the system, or may be used as a part of a hot air to be used in the drying step.

Figure 8:
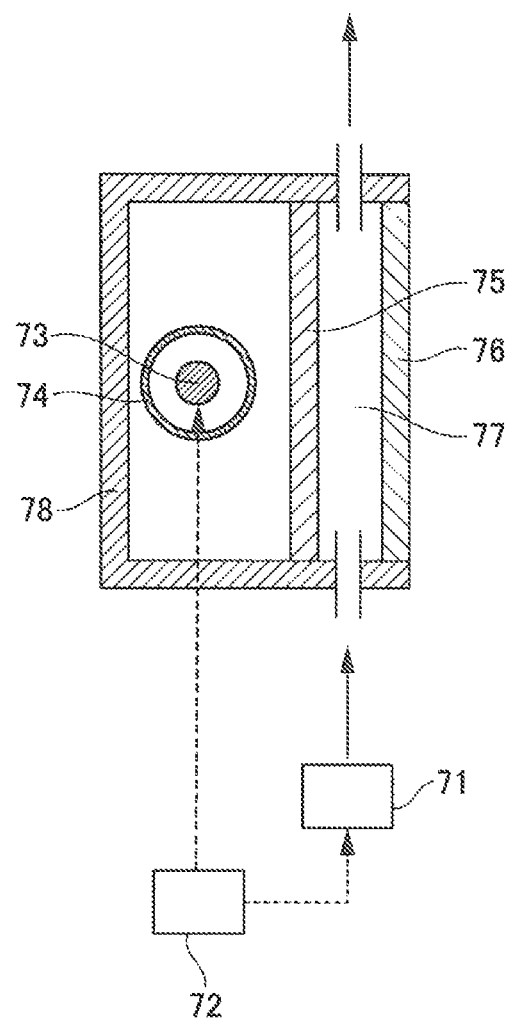
FIG. 8 is a schematic view showing the configuration of the infrared ray heater.

The infrared ray heater may have the configuration, for example, shown in FIG. 8 other than the above configuration. The infrared ray heater shown in FIG. 8 has square (rectangular) appearance, three faces of a filament 73 and a protective tube 74 are covered by reflective plates 78, and the filters 75 and 76 are arranged in the parallel manner in the remaining direction. Then, between the parallel filters 75 and 76, the hollow part 77 is provided for passing (circulating) the cooling medium. In addition, the cooling mechanism 71 which supplies the cooling medium to the hollow part 77 is connected to the infrared ray heater, and the controlling device 72 is connected to the cooling mechanism 71 and the filament 73.

A filament temperature of the infrared ray heater is preferably, from the viewpoint of both the reduced water content of the coating film and the protection from deformation, 600° C. or more, and is, from the viewpoint of heat resistance, 3000° C. or less. The filament temperature may be optionally selected and changed depending to the desired drying conditions. The filament temperature can be measured by the use of, for example, a radiation thermometer.

The surface temperature of the outermost filter which is arranged to the article to be dried (filter 76 in the example shown in FIG. 7 and FIG. 8) is preferably, form the viewpoint of inhibiting the secondary radiation due to the infrared ray absorption itself, 200° C. or less, furthermore preferably 150° C. or less. The surface temperature of the outermost filter can be regulated by passing the air through the space between filters laminated double or more.

Furthermore, in the vacuum drying apparatus or the inert oven, when a drying zone thereof is composed of (covered with) a material having a high infrared ray reflection, the infrared ray which is not absorbed to the article to be dried can be utilized efficiently.

According to the above treatment for reducing the in-membrane water content, the in-membrane water content of the layer formed between the gas barrier layer 2 and the cap layer 12 is made to be at a level of less than $1.0 \times 10^{15}$/mg. After carrying out the treatment for reducing the in-membrane water content, the in-membrane water content of the layer formed between the gas barrier layer 2 and the cap layer 12, it is necessary to reduce at a level of less than $1.0 \times 10^{15}$/mg until the formation of the cap layer 12.

In order to maintain the in-membrane water content at a level of less than $1.0 \times 10^{15}$/mg, it is necessary to restore the light extraction substrate under a drying inert gas atmosphere or vacuum.

Note that the treatment for reducing the in-membrane water content may be utilized as the drying step or the curing treating step of the layer finally formed in the above layer formed between the gas barrier layer 2 and the cap layer 12.

In the present embodiment, when a thermosetting resin is used for the smoothing layer 4, by carrying out the vacuum drying in the curing treatment of the thermosetting resin, it is also possible to carry out both the curing treatment of the smoothing layer 4 and the treatment for reducing the in-membrane water content of the layer formed between the gas barrier layer 2 and the cap layer 12.

[Step of Forming Cap Layer]

Next, while maintaining the in-membrane water content at a level of less than $1.0 \times 10^{15}$/mg, the cap layer 12 which is composed of the silicon nitride as a principal component on the smoothing layer 4 through the dry process such as the plasma CVD method.

[Step of Forming Transparent Electrode]

Next, on the cap layer 12, for example, the underlayer 5a composed of a compound containing nitrogen atom is formed so as to have a thickness of 1 μm or less, preferably 10 to 100 nm by an appropriate method such as a deposition method.

Next, on the underlayer 5a, the conductive layer 5b composed of silver (or the alloy containing silver as a principal component) is formed so as to have a thickness of 12 nm or less, preferably 4 to 9 nm by an appropriate method such as a deposition method to produce the transparent electrode 5 as an anode. At the same time, at the end of the transparent electrode 5, the extraction electrode 8 which is connected to the external power source is formed by an appropriate method such as a deposition method.

[Step of Forming Light-Emitting Unit]

Next, the positive hole injection layer 6a, the positive hole transport layer 6b, the light-emitting layer 6c, the electron transport layer 6d, and the electron injection layer 6e are deposited in the order to form the light-emitting unit 6 on the transparent electrode. In the formation of the respective layers, there may be employed a spin coating method, a casting method, an inkjet printing method, a vapor deposition method, a sputtering method, a printing method, and the like, and from the viewpoints that a homogeneous layer can easily be obtained and a pinhole is difficult to be generated, the vacuum vapor deposition method or the spin coating method is particularly preferable. In addition, a different deposition method may be employed to each layer. When employing the vapor deposition method for the deposition of each layer, though the vapor deposition conditions are varied according to the kind of the compound to be used, it is desirable to select each condition optionally from the ranges of a heating temperature of boat to house a compound of 50 to 450° C., a degree of vacuum $1\times10^{-6}$ to $1\times10^{-2}$ Pa, a deposition rate of 0.01 to 50 nm/sec, a temperature of substrate of −50 to 300° C., and a thickness of membrane of 0.1 to 5 µm.

[Step of Forming Counter Electrode]

After forming the light-emitting unit 6 in the above, a counter electrode 7 which constructs a cathode is formed thereon by an appropriate method such as a deposition method or a spattering method. At this time, pattern is formed from upper side of the light-emitting unit 6 so that a terminal portion of the counter electrode 7 is pulled out from the peripheral of the resin base material 1, while keeping insulation state against the transparent electrode 5 by the light-emitting unit 6. As a result, the organic EL element is obtained.

[Step of Sealing]

In addition, after that, the sealing member 10 is provided so as to cover at least area from the light-emitting unit 6 to the light scattering layer 3 in the manner that the terminal portions of the transparent electrode 5 (extraction electrode 8) and the counter electrode 7 of the organic EL element are exposed.

A desired organic EL element is obtained on the resin base material 1 by the above procedures. In the production of the organic EL element, although it is preferable to produce the light-emitting unit 6 to the counter electrode 7 throughout by one time vacuum suction, it may be possible that the resin base material 1 is extracted from the vacuum atmosphere to be subjected to other different deposition method. At that time, it is necessary to maintain the in-membrane water content from the step of treatment for reducing the in-membrane water content to the step of forming the cap layer 12. Furthermore, when the resin base material 1 is extracted from the vacuum atmosphere, it is necessary to consider that the procedures are carried out under a dry inert gas atmosphere.

EXAMPLE

Hereinafter, the present invention will be explained specifically with reference to examples, the present invention is not limited thereto. Besides, the word "%" used in the following working examples means "% by mass", otherwise noted.

[Fabrication of Organic EL Element 101]

(1) Fabrication of Substrate (1-1) Resin Base Material

A biaxially oriented polyethylene naphthalate film was used (PEN film, thickness: 100 µm, width: 350 mm, manufactured by Teijin DuPont Films Co., Ltd., trade name "Teonex Q65FA") as the resin base material.

(1-2) Fabrication of Primer Layer

OPSTAR 27501 being a UV curable organic/inorganic hybrid hard coating material manufactured by JSR Co., Ltd. was applied to an easily-adhering surface of the resin base material so that the thickness after coating and drying was 4 µm by the use of a wire bar, and after drying under the drying condition: 80° C., 3 minutes, a primer layer was formed by curing under the curing condition: 1.0 J/cm$^2$ by the use of a high-pressure mercury lamp, in the atmospheric circumstance.

(1-3) Fabrication of First Gas Barrier Layer

The resin base material was mounted on a CVD apparatus, and then a first gas barrier layer having a thickness of 300 nm was fabricated on the resin base material under the following deposition conditions (plasma CVD conditions) so as to have each element profile shown in FIG. 6.

<Deposition Conditions>

Feeding rate of raw material gas (hexamethyldisiloxane (HMDSO, $(CH_3)_6SiO$)): 50 sccm (Standard Cubic Centimeter per Minute)

Feeding rate of oxygen gas ($O_2$): 500 sccm

Degree of vacuum in vacuum chamber: 3 Pa

Applied power from plasma generation power source: 0.8 kW

Frequency of plasma generation power source: 80 kHz

Transporting speed of film: 0.5 to 1.66 m/min (1-4) Fabrication of Second Gas Barrier Layer A 10% by mass solution of perhydropolysilazane (PHPS) (AQUAMICANN120-10, non-catalyst type, manufactured by AZ made Electronic Materials Co., Ltd.) in dibutyl ether was used as a coating solution.

The above coating solution was applied by the use of a wire bar so that a dry (average) thickness was 300 nm, and was dried by treatment under an atmosphere of a temperature of 85° C., a humidity of 55% RH for 1 minute, and was further subjected to dehydration treatment under an atmosphere of a temperature of 25° C., a humidity of 10% RH (dew point −8° C.) for 10 minutes, thereby forming a polysilazane layer.

Next, the thus formed polysilazane layer was subjected to silica conversion processing under atmospheric pressure by the use of the following ultraviolet irradiation apparatus.

<Ultraviolet Irradiation Apparatus>

Apparatus: Excimer irradiation apparatus MODEL MECL-M-1-200 manufactured by M D COM Co., Ltd.

Irradiation wavelength: 172 nm

Lamp filler gas: Xe

<Modification Treatment Conditions>

The substrate on which the polysilazane layer was formed was fixed to the working stage was subjected to the modification treatment under the following conditions, and thus a second gas barrier layer was formed.

Excimer lamp light intensity: 130 mW/cm$^2$ (172 nm)

Distance between sample and light source: 1 mm Heating temperature of stage: 70° C.

Oxygen concentration within irradiation apparatus: 1.0%

Irradiation time of excimer lamp: 5 seconds

The thus fabricated substrate had a water vapor permeability of less than $1\times10^{-4}$ g/(m$^2$·24 h) below, and exhibited very good water vapor barrier property.

Note that, in the embodiment, the water content and the water vapor permeability were values measured by the method in accordance with JIS K 7129-1992 at a temperature of 25±0.5° C., a relative humidity of 90±2% RH.

(2) Fabrication of Transparent Electrode

The fabricated substrate on which the gas barrier layer was formed was cut to a size of 5 cm×5 cm, and was fixed to a substrate holder of the commercially available vacuum vapor deposition apparatus, and the exemplified compound (1-6) was put in a resistive heating boat of tungsten. Then, these substrate holder and resistive heating boat were mounted in a first vacuum tank. In addition, silver (Ag) was put in a resistive heating boat of tungsten, and was mounted in a second vacuum tank.

[Chemical formula 2]

(1) Exemplified compound (1-6)

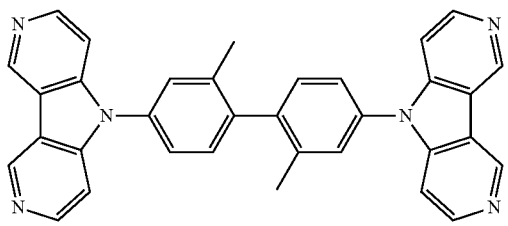

Next, after reduction of a pressure of the first vacuum tank to 4×10⁻⁴ Pa, the heating boat in which the exemplified compound (1-6) was placed was heated by applying an electric current, and then, the underlayer composed of the exemplified compound (1-6) for the transparent electrode was formed on the substrate at a deposition rate of 0.1 to 0.2 nm/sec. A thickness of the underlayer was 50 nm.

Next, the substrate on which the underlayer was formed was transferred to the second vacuum tank under vacuum, and after reduction of a pressure of the second vacuum tank to 4×10⁻⁴ Pa, the heating boat containing silver was heated by applying an electric current, and then there was formed a conductive layer made of silver having a thickness of 8 nm at a deposition rate within the range of 0.1 to 0.2 nm/sec on the underlayer, and thus there was formed a transparent electrode (anode) having a laminated structure of the underlayer and the conductive layer.

(3) Fabrication of Organic Functional Layer

Crucibles for vapor deposition in the vacuum vapor deposition apparatus were charged with a constituent material for each layer of the organic functional layer in an optimum amount being suitable for fabricating the respective organic EL elements. The crucible for vapor deposition was made of a resistive heating material such as molybdenum or tungsten.

There were used, as the constituent material for each layer of the organic functional layers, the following compounds α-NPD, BD-1, GD-1, RD-1, H-1, H-2 and E-1.

[Chemical formula 3]

α-NPD

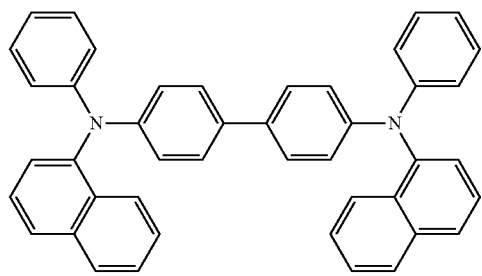

BD-1

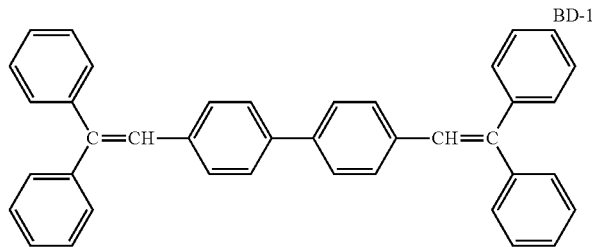

GD-1

RD-1

H-1

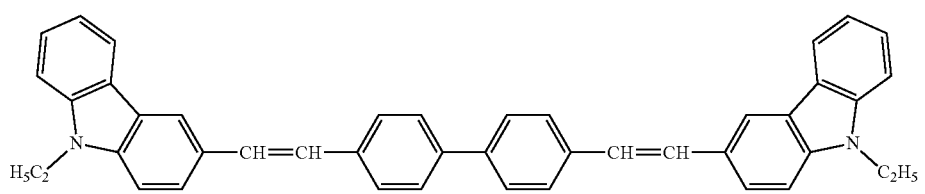

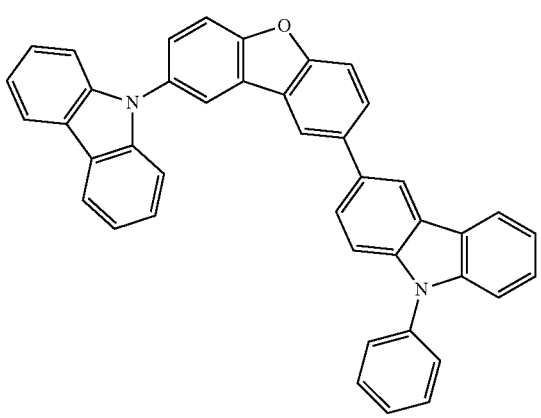

H-2

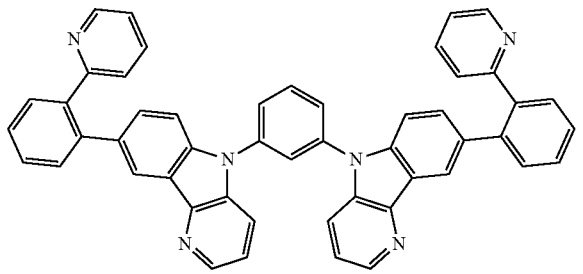

E-1

First, after reduction of to a degree of vacuum of $1\times10^{-4}$ Pa, the crucible for vapor deposition containing α-NPD was heated by passing a current, and the α-NPD was deposited at a deposition rate of 0.1 nm/sec, with the result that a positive hole injection transport layer having a thickness of 40 nm was formed on the transparent electrode.

Similarly, the compound BD-1 and H-1 were co-deposited at a deposition rate of 0.1 nm/sec so that a concentration of the compound BD-1 was 5%, and thereby a fluorescent light-emitting layer exhibiting a blue color and having a thickness of 15 nm was formed.

Next, the compound GD-1, RD-1 and H-2 were co-deposited at a deposition rate of 0.1 nm/sec so that a concentration of the compound GD-1 was 17% and a concentration of the compound RD-1 was 0.8%, and thereby a phosphorescent light-emitting layer exhibiting a yellow color and having a thickness of 15 nm was formed.

After that, the compound E-1 was deposited at a deposition rate of 0.1 nm/sec, and thereby an electron transport layer having a thickness of 30 nm was formed.

(4) Fabrication of Counter Electrode

Furthermore, a lithium fluoride (LiF) layer having a thickness of 1.5 nm was formed, and then a transparent electrode (cathode) was formed by deposition of an aluminum layer having a thickness of 110 nm. The transparent electrode was formed, in a state of being electrically insulated by the organic functional layer from the positive hole injection layer to the electron injection layer and in the form of the terminal portion being laid out from a peripheral edge of the substrate.

Note that, a vapor deposition mask was used for formation of each layer, there was set, as a light-emitting region, the region of 4.5 cm×4.5 cm positioned at the center of the 5 cm×5 cm substrate, and there was provided a non-light-emitting region having a width of 0.25 cm around the whole of the light-emitting region.

(5) Sealing (5-1) Preparation of Pressure Sensitive Adhesive Composition

A pressure sensitive adhesive composition having a solid content of 25% by mass was prepared by dissolving 100 parts by mass of Oppanol B50 (manufactured by BASF made, Mw: 340000) as a polyisobutylene-based resin, 30 parts by mass of Nisseki Polybutene Grade HV-1900 (manufactured by JX Nippon Oil & Energy Corporation, Mw: 1900) as a polybutene resin, 0.5 part by mass of TINUVIN 765 (Ciba Japan KK, having a tertiary hindered amine group) as a hindered amine-based photostabilizer, 0.5 part by mass of IRGANOX 1010 (manufactured by Chiba Japan KK, the β-positions of the hindered phenol group being both tertiary butyl groups) as a hindered phenol-based antioxidant, and 50 parts by mass of Eastotac H-100L Resin (manufactured by Eastman Chemical Co., Ltd.) as a cyclic olefin-based polymer in toluene.

(5-2) Fabrication of Adhesive Sheet for Sealing

As a gas barrier layer, the solution of the adhesive composition prepared above was applied to an aluminum (Al) side (gas barrier layer side) of an aluminum-deposited polyethylene terephthalate film Alpet 12/34 (manufactured by Asia-Alumi Co., Ltd.) so that a dry thickness of the pressure sensitive adhesive layer was 20 μm, and dried at 120° C. for 2 minutes to form an adhesive layer. Next, a peeling-off treated surface of a peeling-off treated polyethylene terephthalate film having a thickness of 38 μm as a peeling-off sheet adhered to the pressure adhesive layer surface to form a pressure sensitive adhesive sheet for sealing.

(5-3) Sealing

Next, the peeling-off sheet of the adhesive sheet for sealing fabricated by the above method was removed under a nitrogen atmosphere, and the adhesive sheet for sealing was dried on a hot plate heated at 120° C. for 10 minutes, and after confirming that the sheet was cooled to room temperature (25° C.), the cathode was completely laminated in a state of being completely covered, and then heated at 90° C. for 10 minutes. The organic EL element 101 was fabricated in such a way.

[Fabrication of Organic EL Element 102]

In the above organic EL element 101, the following light extraction layer composed of the light scattering layer and the smoothing layer was formed on the second gas barrier layer of the substrate and thus an organic EL element 102 was fabricated.

(6) Fabrication of Light Extraction Layer (6-1) Fabrication of Light Scattering Layer $TiO_2$ particles having a refractive index of 2.4 and an average particle size of 0.25 μm (JR600A manufactured by TEICA CORPORATION) and a resin solution (ED230AL (organic inorganic hybrid resin manufactured by APM Corporation)) were mixed in a solid content ratio of 20% by volume/80% by volume, which was then prepared so as to have a solid content of 15% by mass in propylene glycol monomethyl ether (PGME).

An additive (Disperbyk-2096 manufactured by Byk Chemi Japan Co., Ltd.) of 0.4% by mass was added to the above solid component (effective mass component), which was subjected to formulation design in a ratio of 10 ml amount.

Specifically, the above $TiO_2$ particles, the above solvent and the additives were mixed in a mass ratio of 10% relative to the $TiO_2$ particles, and dispersed while being cooled at normal temperature (25° C.) for 10 minutes by the use of an ultrasonic dispersing machine (UH-50 manufactured by SMT Co., Ltd.) under the standard conditions of microchip step (MS-3 3 mmφ manufactured by SMT Co., Ltd.), with the result that a $TiO_2$ dispersion was fabricated.

Next, the resin solution was added to and mixed little by little with the $TiO_2$ dispersion while being stirred at 100 rpm, and after the completion of the addition, the stirring speed was raised to 500 rpm and then the resultant substance was stirred for 10 minutes, filtered by a hydrophobic PVDF 0.45 μm filter (manufactured by Whatman Co., Ltd.), with the result that a desired coating solution for the light scattering layer was obtained.

The above coating solution was applied by the inkjet coating method onto the second gas barrier layer of the substrate, which was then subjected to simple drying (80° C. for 2 minutes), and furthermore, the resultant coating layer was subjected to drying treatment for 5 minutes under the output condition of less than 80° C. of a base material temperature by the use of a wavelength controllable IR to be described below.

Then, the curing reaction was accelerated under the following modification treatment conditions to thereby give the light scattering layer having a thickness of 0.3 μm. The light scattering layer having a refractive index n of 1.66 was fabricated in such a way.

<Modification Treatment Conditions>
Excimer lamp light intensity: 130 mW/cm$^2$ (172 nm)
Distance between sample and light source: 1 mm
Heating temperature of stage: 70° C.
Oxygen concentration in irradiation apparatus: 20.0%
Irradiation time of excimer lamp: 5 seconds (6-2) Fabrication of Smoothing Layer Next, a coating solution for a smoothing layer was prepared by addition of a UV curable resin having a high refractive index (Lioduras TYT82-01 manufactured by TOYO INK CO., LTD., nanosol particle: $TiO_2$) to a mixed organic solvent of propylene glycol monomethyl ether (PGME) and 2-methyl-2,4-pentanediol (PD) in a solvent ratio of 90% by mass/10% by mass, so as to be 12% by mass of a solid concentration, which was subjected to formulation design in a ratio of 10 ml amount.

Specifically, the above UV curable resin having a high refractive index was mixed with the solvent, and after stirring at 500 rpm for 1 minute, filtered by a hydrophobic PVDF 0.2 μm filter (manufactured by Whatman Co., Ltd.) to obtain the desired coating solution for a smoothing layer.

The above coating solution was applied according to the inkjet coating method on the scattering layer, and then, dried according to ready drying (80° C. for 2 minutes), and furthermore, the coating layer was subjected to drying treatment for 5 minutes under the output condition of less than 80° C. of the substrate temperature by the use of wavelength controllable IR.

The drying treatment was carried out by attaching two quartz glass plates which can absorb an infrared ray having a wavelength of 3.5 μm or more to a radiant heat transmission machine with a wavelength controllable infeed ray heater (IR radiation machine, Ultimate heater/carbon, manufactured by MEI MEI INDUSTRIES INC.), and a cooling air was flowed between the glass plates.

At this time, the cooling air was flowed at 200 L/min, and a temperature of the quartz glass on the tube surface was lowered at less than 120° C. The temperature of the substrate was measured by arranging the k thermocouples on the both surfaces of the substrate and above the substrate by 5 mm, and connecting to a NR2000 (manufactured by KEYENCE CORPORATION INC.).

Next, the curing reaction was accelerated under the following modification treatment conditions to obtain the smoothing layer having a thickness of 0.5 μm, and a light extraction layer having two-layered structure of the light scattering layer and the smoothing layer.

<Modification Treatment Conditions>
Excimer lamp light intensity: 130 mW/cm$^2$ (172 nm)
Distance between sample and light source: 1 mm
Heating temperature of stage: 70° C.
Oxygen concentration in irradiation apparatus: 20.0% (atmospheric)
Irradiation time of excimer lamp: 0.5 seconds According to the above procedures, an organic EL element 102 was fabricated.

[Fabrication of Organic EL Element 103]

On the smoothing layer of the substrate in the above organic EL element 102, a light extraction layer was formed by providing the following cap layer to fabricate an organic EL element 103.

(7) Fabrication of Cap Layer

By the use of a parallel plate-type plasma CVD apparatus (PED-401 manufactured by Anelva), a substrate on which the smoothing layer was formed thereon was set to the lower electrode side of a chamber of the plasma CVD apparatus. Next, the camber of the plasma CVD apparatus was reduced to a reached degree of vacuum of $1.0 \times 10^{-2}$ Pa by an oil rotary pump and a turbo molecular pump. After that, via a material supplying nozzle, $SiH_4$ gas, $NH_3$ gas, $H_2$ gas and $N_2$ gas were introduced into the chamber. By controlling a valve for regulating pressure which is provided between the chamber and a vacuum discharge pump, the inside pressure of the chamber was adjusted to 20 Pa. Next, by applying an electric power (charged power: 200 W) having a frequency of 90 kHz to the lower electrode, a glow discharge plasma was generated between the lower electrode and an upper electrode (near an opening of the material supplying nozzle of the chamber (gas inlet)). A cap layer composed of a silicon nitride with a nitrogen ratio of 41% and having a thickness of 300 nm was formed by carrying out the plasma treatment for 3 minutes. The obtained film had a refractive index n of 1.92. According to these procedures, an organic EL element 103 was fabricated.

[Fabrication of Organic EL Elements 104 to 107]

Organic EL elements 104 to 107 were fabricated in a similar way to that in the organic EL element 103 except that the following drying treatment (just-before-drying) was carried out before forming the cap layer. The drying conditions for the organic EL elements 104 to 107 will be shown below.

<Drying Condition>
Element 104: 100° C. for 5 minutes on heating stage in vacuum
Element 105: 100° C. for 10 minutes on heating stage in vacuum
Element 106: 100° C. for 20 minutes on heating stage in vacuum
Element 107: 100° C. for 60 minutes on heating stage in vacuum The drying treatment was carried out under the above drying condition, by directly contacting a heating part of the heating stage to the back surface (surface where no element was formed) of the resin base material under vacuum. Then, while maintaining the vacuum circumstance, the substrate was moved to the plasma CVD apparatus to provide the cap layer. The degree of the drying treatment was $1.0 \times 10^{-4}$ Pa.

[Fabrication of Organic EL Elements 108 to 111]

Organic EL elements 108 to 111 were fabricated in a similar way to that in the organic EL element 103 except that the following drying treatment (just-before-drying) was carried out before forming the cap layer. The drying conditions for the organic EL elements 108 to 111 will be shown below.

<Drying Condition>

Element 108: under vacuum, subjecting to wavelength controllable IR for 0.5 minute Element 109: under vacuum, subjecting to wavelength controllable IR for 2 minutes Element 110: under vacuum, subjecting to wavelength controllable IR for 10 minutes Element 111: under vacuum, subjecting to wavelength controllable IR for 60 minutes The drying treatment was carried out by radiant heat transmission drying with the wavelength controllable IR heater under the above drying condition. Specifically, by attaching two quartz glass plates which can absorb an infrared ray having a wavelength of 3.5 μm or more to the IR radiation machine (Ultimate heater/carbon, manufactured by MEI MEI INDUSTRIES INC.), and a tube surface of the infrared ray heater where a cooling air was flowed between the glass plates (referring to FIG. 7) was arranged at 100 mm above the sample. Then, while maintaining the vacuum circumstance, the substrate was moved to the plasma CVD apparatus to provide the cap layer. The degree of the drying treatment was $1.0 \times 10^{-4}$ Pa.

The above drying treatment was carried out at a filament temperature (° C.) of the infrared ray heater of 1500° C., and at a surface temperature of the quartz glass filter of 140° C.

Note that the filament temperature (° C.) of the infrared ray heater was measured by the use of a non-contact type thermometer (IR-AHS manufactured by Chino) on the basis that the radiation ratio of tungsten filter was 0.39. In addition, as to the filter temperature (° C.), the surface temperature of the quartz glass filter was measured by the use of a contact type thermometer (HFT-60 manufactured by Anritsu Meter Co., Ltd.) and the flow rate of the cooling air was controlled so that the surface temperature was regulated to be the above temperature.

[Fabrication of Organic EL Elements 112 to 115]

Organic EL elements 112 to 115 were fabricated in a similar way to that in the organic EL element 103 except that, in the fabrication of the light extraction layer, after fabricating only the light scattering layer without fabricating the smoothing layer, the following drying treatment (just-before-drying) was carried out, and then fabricating the cap layer on the light scattering layer. Hereinafter, the drying conditions for the organic EL elements 112 to 115 will be shown.

<Drying Condition>

Element 112: under vacuum, subjecting to wavelength controllable IR for 0.5 minute Element 113: under vacuum, subjecting to wavelength controllable IR for 2 minutes Element 114: under vacuum, subjecting to wavelength controllable IR for 10 minutes Element 115: under vacuum, subjecting to wavelength controllable IR for 60 minutes The drying treatment was carried out by radiant heat transmission drying with the wavelength controllable IR heater under the above drying condition in a similar way to that in the above organic EL elements 108 to 111. The degree of the drying treatment was $1.0 \times 10^{-4}$ Pa.

[Amount of Water]

The configuration of each organic EL elements 101 to 115 fabricated in the above process will be shown in Table 1. An amount of water (/mg) discharged from the light scattering layer and the smoothing layer was quantitatively measured. Specifically, the light scattering layer and/or the smoothing layer were provided on a glass substrate of 1 cm square according to the same manner as in the above organic EL elements 101 to 115. At this time, samples corresponding to the organic EL element 104 to 115 were subjected to the same drying treatment.

Consequently, the above sample of 1 cm square was heated from 20° C. to 200° C. at an elevating temperature of 60° C./min. by the use of a thermal desorption analytical device (TDS1200; manufactured by ESCO Ltd.), thereafter kept for one hour, and then the discharged amount of water was measured quantitatively.

Note that, since the organic EL element 101 had no light scattering layer and smoothing layer, with respect to this sample, the amount of water discharged from the glass substrate was measured quantitatively. Furthermore, with respect to the organic EL elements 112 to 115 had only the light scattering layer, the amount of water discharged from the sample where only the scattering layer was formed was measured quantitatively.

The water content (amount of water) is a value of a sample that is regulated its moisture sufficiently at a temperature of 25±0.5° C., and at a relative humidity of 90±2% RH.

TABLE 1

| Element | Scattering layer | Smoothing layer | Cap layer | Just-before-drying | Amount of water | |
|---|---|---|---|---|---|---|
| 101 | None | None | None | None | $6.0 \times 10^{13}$ | Comparison |
| 102 | Provided | Provided | None | None | $8.0 \times 10^{17}$ | Comparison |
| 103 | Provided | Provided | Provided | None | $5.0 \times 10^{16}$ | Comparison |
| 104 | Provided | Provided | Provided | 100° C. for 5 minutes | $5.0 \times 10^{15}$ | Comparison |
| 105 | Provided | Provided | Provided | 100° C. for 10 minutes | $2.0 \times 10^{15}$ | Comparison |
| 106 | Provided | Provided | Provided | 100° C. for 20 minutes | $9.0 \times 10^{14}$ | Present invention |
| 107 | Provided | Provided | Provided | 100° C. for 60 minutes | $7.0 \times 10^{14}$ | Present invention |
| 108 | Provided | Provided | Provided | IR for 0.5 minute | $5.0 \times 10^{15}$ | Comparison |
| 109 | Provided | Provided | Provided | IR for 2 minutes | $5.0 \times 10^{14}$ | Present invention |
| 110 | Provided | Provided | Provided | IR for 10 minutes | $1.0 \times 10^{14}$ | Present invention |
| 111 | Provided | Provided | Provided | IR for 60 minutes | $9.0 \times 10^{13}$ | Present invention |
| 112 | Provided | None | Provided | IR for 0.5 minute | $5.0 \times 10^{15}$ | Comparison |

TABLE 1-continued

| Element | Scattering layer | Smoothing layer | Cap layer | Just-before-drying | Amount of water | |
|---|---|---|---|---|---|---|
| 113 | Provided | None | Provided | IR for 2 minutes | $2.0 \times 10^{14}$ | Present invention |
| 114 | Provided | None | Provided | IR for 10 minutes | $8.0 \times 10^{13}$ | Present invention |
| 115 | Provided | None | Provided | IR for 60 minutes | $7.0 \times 10^{13}$ | Present invention |

[Evaluation Methods]
(Light Emission Efficiency)

With respect to the respective organic EL element of the fabricated sample, the light emission test was conducted by lighting at room temperature (25° C.) under the constant current density condition of 2.5 mA/cm$^2$, measuring the light emission luminance of each organic EL element with a spectroscopic radiant luminance meter CS-2000 (manufactured by Konica Minolta, Inc.), and then calculating the light emission efficiency (electric power efficiency) at the current value.

Note that the light emission efficiency is expressed as a relative value that the light emission efficiency of the organic EL element 101 is 100. An element having a relative value of light emission efficiency of 120 or more is preferable.
(Preservability)

Each organic EL element was entered in to a thermostat oven at 85° C. (dry), and the elevation ratio of voltage before and after the preservation under the constant current density condition which was the same as in the above light emission efficiency evaluation was evaluated every 24 hours. When the voltage elevation from the start of evaluation is beyond 1.0 V, the result was evaluated as bad, and the period of time (h) until the result is bad is determined as the preservability.
(Light Emission Reliability)

In the conditions of the above preservability, the increasing ratio (%) of dark spot at the light emission under the constant current before and after preserving 500 hours was compared. The area % was calculated by binarizing on the basis of a certain threshold value with an image treating software such as Light Area Measure Version 1.0.0.0 (Digital Hands Co., Ltd.).
(Flexible Reliability)

The element which was solid-sealed was subjected to winding test on a cylinder of 20 mmφ repeatedly before the preservation under the above preservability condition (before preservation) and after preserving for 500 hours, and the state of peeling off and bad light emission were confirmed after winding 100 times.

The results of evaluation as to the respective organic EL elements 101 to 115 will be shown in Table 2.

TABLE 2

| Element | Light emission efficiency | Preservability | Light emission reliability | Flexible reliability Before preservation | Flexible reliability After preservation | |
|---|---|---|---|---|---|---|
| 101 | 100 | 500 or more | 0.4% | OK | OK | Comparison |
| 102 | 133 | 24 | 10% or more | OK | NG | Comparison |
| 103 | 146 | 500 or more | 3% | OK | NG | Comparison |
| 104 | 146 | 500 or more | 3% | OK | NG | Comparison |
| 105 | 146 | 500 or more | 3% | OK | NG | Comparison |
| 106 | 146 | 500 or more | 1% | OK | OK | Present invention |
| 107 | 146 | 500 or more | 1% | OK | OK | Present invention |
| 108 | 146 | 500 or more | 3% | OK | NG | Comparison |
| 109 | 146 | 500 or more | 1% | OK | OK | Present invention |
| 110 | 146 | 500 or more | 0.7% | OK | OK | Present invention |
| 111 | 146 | 500 or more | 0.6% | OK | OK | Present invention |
| 112 | 146 | 500 or more | 3% | OK | NG | Comparison |
| 113 | 146 | 500 or more | 1% | OK | OK | Present invention |
| 114 | 146 | 500 or more | 0.7% | OK | OK | Present invention |
| 115 | 146 | 500 or more | 0.5% | OK | OK | Present invention |

As shown in Table 1, with respect to the sample corresponding to the organic EL element 101, the amount of water discharged from the glass substrate alone was $6.0 \times 10^{13}$/mg. This is the sample having the lowest amount of water because no element was provided on the glass substrate.

On the other hand, the amounts of water discharged from the samples corresponding to the organic EL elements 102, 103 where the light extraction layer (light scattering layer, smoothing layer) was provided but the drying treatment was not carried out were $5.0 \times 10^{16}$/mg or more. These are the samples having the largest amount of water.

Furthermore, the discharged amount of water of all the samples corresponding to the organic EL elements 104 to 115 which were subjected to the drying treatment had the amount of water were lower than the amount of water of the samples corresponding to the organic EL elements 102 and 103.

Furthermore, the discharged amounts of water of the samples corresponding to the organic EL elements 104 and 105 which were dried at 100° C. for 5 minutes or 10 minutes were more than $1.0 \times 10^{15}$/mg, and were $5.0 \times 10^{15}$/mg and $2.0 \times 10^{15}$/mg.

On the other hand, the discharged amounts of water of the samples corresponding to the organic EL elements 106 and 107 which were dried at 100° C. for 20 minutes or 60 minutes were less than $1.0 \times 10^{15}$/mg, and were $9.0 \times 10^{14}$/mg and $7.0 \times 10^{14}$/mg.

Accordingly, in order that the in-membrane water content is less than $1.0\times10^{15}$/mg, the drying treatment is not enough at 100° C. for 10 minutes, but it is necessary to dry at 100° C. for 20 minutes or more.

Furthermore, the discharged amounts of water of the samples corresponding to the organic EL elements 108 and 112 which were dried by the wavelength controllable infrared ray heater for 0.5 minute were more than $1.0\times10^{15}$/mg, and were $5.0\times10^{15}$/mg unless the presence of the smoothing layer.

On the other hand, the discharged amounts of water of the samples corresponding to the organic EL elements 109 to 111, and 113 to 115 which were dried by the wavelength controllable infrared ray heater for 2 minutes or more were less than $1.0\times10^{15}$/mg, and were $5.0\times10^{14}$/mg, $1.0\times10^{14}$/mg, $9.0\times10^{13}$/mg, $2.0\times10^{14}$/mg, $8.0\times10^{13}$/mg, and $7.0\times10^{13}$/mg.

Accordingly, in order that the in-membrane water content is less than $1.0\times10^{15}$/mg, it is preferable to dry for 2 minutes or more by the use of wavelength controllable infrared ray heater.

Furthermore, as shown in Table 2, although the organic EL elements 102 to 115 having the light extraction layer were enhanced in the light emission efficiency, the organic EL element 102 which did not have the cap layer was remarkably worse in the preservability.

Furthermore, the organic EL elements 103 to 115 having the cap layer were good in the preservability, but the organic EL elements 103 to 105, the organic EL element 108 and the organic EL element 112 which had the in-membrane water contents of more than $1.0\times10^{15}$/mg had a high generation ratio of the dark spot after the preservation, which results in low light emission reliability. Furthermore, the organic EL elements 103 to 105, the organic EL element 108 and the organic EL element 112 were bad also in the flexible reliability after the preservation.

In contrast, the organic EL elements 106 and 107, the organic EL elements 109 to 111 and the organic EL elements 113 to 115 which had the in-membrane water contents of less than $1.0\times10^{15}$/mg had good results in the light emission reliability and the light emission reliability after the preservation. Particularly, the organic EL element having a lower in-membrane water content had a lower generation ratio of the dark spot after the preservation, which results in good light emission reliability.

From the above results, when the layer formed between the gas barrier layer and the cap layer has the in-membrane water content of less than $1.0\times10^{15}$/mg, it is possible to obtain the organic EL element having a high reliability. Furthermore, as the in-membrane water content is lower, the reliability of the organic EL element is enhanced.

Note that the present invention is not limited to the configurations in the above described embodiments, various modifications and changes can be made within the scope of the present invention.

REFERENCE SIGNS LIST

1 Resin base material
2 Gas barrier layer
2*a* First gas barrier layer
2*b* Second gas barrier layer
3 Light scattering layer
4 Smoothing layer
5 Transparent electrode
5*a* Underlayer
5*b* Conductive layer
6 Light-emitting unit
6*a* Positive hole injection layer
6*b* Positive hole transport layer
6*c* Light-emitting layer
6*d* Electron transport layer
6*e* Electron injection layer
7 Counter electrode
8 Extraction electrode
9 Auxiliary electrode
10 Sealing member
11 Adhesive
12 Cap layer
20 Delivery roller
21, 22, 23, 24 Conveyer roller
25 Reeling roller
31, 32 Deposition roller
41 Gas inlet
51 Power source for plasma generation
61, 62 Magnetic-field generator
70 Infrared ray heater
71 Cooling mechanism
72 Controlling device
73 Filament
74 Protective tube
75, 76 Filter
77 Hollow part
78 Reflective plate

The invention claimed is:

1. A method for manufacturing a light extraction substrate having at least a gas barrier layer, a light scattering layer, and a cap layer formed in this order on a resin base material, the method comprising the steps of:
   reducing an in-membrane water content in which the in-membrane water content of all layers formed between the gas barrier layer and the cap layer is made to be less than $1.0\times10^{15}$/mg, before forming the cap layer;
   maintaining the in-membrane water content of less than $1.0\times10^{15}$/mg at least until the step of forming the cap layer, after the step of reducing the in-membrane water content; and
   forming the cap layer through a dry process.

2. The method for manufacturing the light extraction substrate according to claim 1, wherein the step of reducing the in-membrane water content performs vacuum drying.

3. The method for manufacturing the light extraction substrate according to claim 1, wherein the dry process is a plasma CVD method.

4. The method for manufacturing the light extraction substrate according to claim 1, wherein the cap layer containing a silicon nitride as a principal component is formed.

5. The method for manufacturing the light extraction substrate according to claim 4, wherein the cap layer having a refractive index of 1.8 or more is formed.

6. The method for manufacturing the light extraction substrate according to claim 1, the method comprising a step of forming a smoothing layer on the light scattering layer.

7. The method for manufacturing the light extraction substrate according to claim 1, wherein the cap layer is formed by a multi-deposition method.

8. The method for manufacturing the light extraction substrate according to claim 1, wherein the step of reducing in-membrane water content performs vacuum drying after curing the light scattering layer.

9. A light extraction substrate comprising:
   a resin base material;
   a gas barrier layer provided on the resin base material;

a light scattering layer provided on the gas barrier layer; and a cap layer formed on the light scattering layer by a dry process, wherein an in-membrane water content of all layers formed between the gas barrier layer and the cap layer is less than $1.0 \times 10^{15}$/mg.

10. A method for manufacturing an organic electroluminescence element comprising: a step of forming a light extraction substrate having at least a gas barrier layer, a light scattering layer, and a cap layer formed in this order on a resin base material; and a step of forming electrodes and a light-emitting unit on the light extraction substrate, wherein the step of forming the light extraction substrate includes the steps of:

reducing an in-membrane water content in which the in-membrane water content of all layers formed between the gas barrier layer and the cap layer is made to be less than $1.0 \times 10^{15}$/mg, before forming the cap layer;

maintaining the in-membrane water content of less than $1.0 \times 10^{15}$/mg at least until the step of forming the cap layer, after the step of reducing the in-membrane water content; and forming the cap layer through a dry process.

11. An organic electroluminescence element comprising:

a light extraction substrate, and a light-emitting unit including an organic functional layer sandwiched by a pair of electrodes, wherein the light extraction substrate includes:

a resin base material;

a gas barrier layer provided on the resin base material;

a light scattering layer provided on the gas barrier layer; and a cap layer formed on the light scattering layer by a dry process; wherein an in-membrane water content of all layers formed between the gas barrier layer and the cap layer is less than $1.0 \times 10^{15}$/mg.

* * * * *